(12) United States Patent
Raimondi et al.

(10) Patent No.: US 9,555,206 B1
(45) Date of Patent: Jan. 31, 2017

(54) DILATOR DEVICE

(71) Applicant: Mark Edward Tellam, Orlando, FL (US)

(72) Inventors: Nestor Omar Raimondi, Buenos Aires (AR); Edgar Jose Jimenez, Orlando, FL (US); Mark Edward Tellam, Orlando, FL (US); Eduardo Alejandro Divo, Orlando, FL (US); Alain Jacques Kassab, Oviedo, FL (US)

( * ) Notice: Subject to any disclaimer, the term of this patent is extended or adjusted under 35 U.S.C. 154(b) by 878 days.

(21) Appl. No.: 13/900,500

(22) Filed: May 22, 2013

(51) Int. Cl.
*A61M 16/04* (2006.01)

(52) U.S. Cl.
CPC ................................ *A61M 16/0472* (2013.01)

(58) Field of Classification Search
CPC . A61B 17/02; A61B 17/0206; A61B 17/0218; A61B 17/0293; A61B 17/2804; A61B 17/29; A61B 17/3403; A61B 17/3415; A61B 17/3423; A61B 17/3439; A61B 17/44; A61B 2017/2902; A61B 2017/2919; A61B 2017/2924; A61B 2017/293; A61B 1/32; A61M 16/0472; A61M 16/0488; A61M 29/00
See application file for complete search history.

(56) References Cited

U.S. PATENT DOCUMENTS

| | | | | |
|---|---|---|---|---|
| 3,817,250 A | * | 6/1974 | Weiss | A61M 16/0472 128/207.29 |
| 4,520,810 A | * | 6/1985 | Weiss | A61B 17/3415 128/200.26 |
| 4,889,112 A | * | 12/1989 | Schachner | A61B 17/2812 128/200.26 |
| 5,217,005 A | * | 6/1993 | Weinstein | A61M 16/0472 128/200.26 |
| 6,109,264 A | * | 8/2000 | Sauer | A61M 16/0472 128/200.26 |
| 6,849,064 B2 | * | 2/2005 | Hamada | A61B 17/02 604/164.01 |
| 8,356,598 B2 | * | 1/2013 | Rumsey | 128/207.29 |

* cited by examiner

*Primary Examiner* — Sarah W Aleman
(74) *Attorney, Agent, or Firm* — The Patent Guild; Paul Royal

(57) ABSTRACT

A dilator device for performing a percutaneous tracheotomy which is inserted into a trachea opening and then actuated to enlarge the opening by single handed actuation.

20 Claims, 48 Drawing Sheets

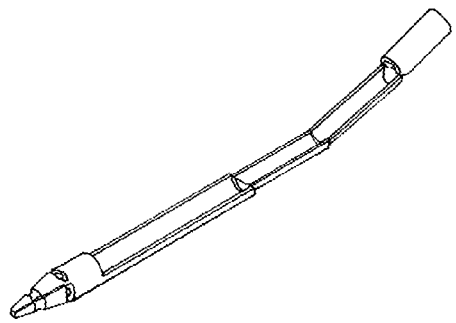
Fig. 34A
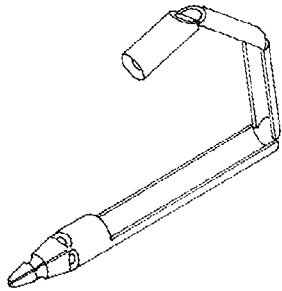 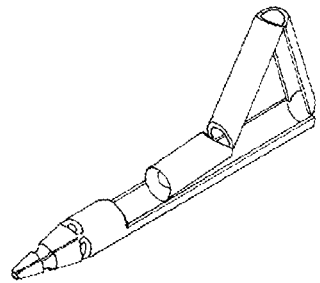
Fig. 34B  Fig. 34C
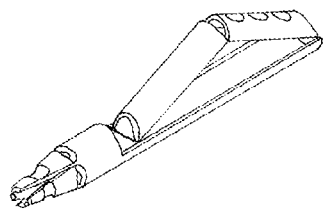 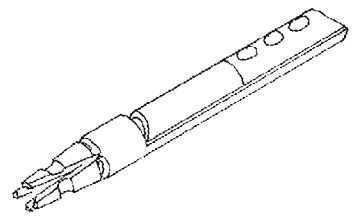
Fig. 34D  Fig. 34E

DILATOR DEVICE

FIELD OF INVENTION

The present invention relates to a dilator device which is inserted an opening and then actuated to enlarge the opening. The workpiece is preferably an object having a wall with isotropic or anisotropic structure. The workpiece could be composite tissue having skin, muscle, ligaments and cartilage elements. Specifically the workpiece could be animal or human tissue. In the present patent application a human trachea is used to illustrate the use of the dilator in performing a percutaneous tracheotomy.

BACKGROUND OF INVENTION

The background of dilation inventions for percutaneous tracheotomy discussed here include a number of devices which are selected for use depending on physician preference and factors such as the physical characteristics of the patient.

Devices in medical use for tracheotomies or tracheostomies are preceded in use by identifying the area for the opening to be created puncturing the area, between sterna notch and cricoid (tracheal) cartilage rings, with a syringe and needle removing the syringe from the needle, which remains in place passing a 'flexible (j-wire) guide', through the needle This 'flexible (j-wire) guide' remains in place for the duration of a' typical percutaneous tracheotomy procedure.

Once this 'flexible (j-wire) guide' is in place in the opening, a monolithic semi-rigid dilator is passed over the 'flexible (j-wire) guide' (threading the available end of the 'flexible (j-wire) guide' through the dilator) and used to begin increasing the size of opening between cartilage rings to be bigger than the syringe needle which was previously removed passing another, larger dilator device, or series of progressively larger devices over the 'flexible (j-wire) guide', to create the final opening A percutaneous tracheotomy is used for example, as the tracheal wall has anisotropic properties which illustrate the advantages and versatility of the dilator.

Griggs Forceps

Griggs forceps are a scissor-like tool which includes a partial passage created by recess channels on each of the mating surfaces of the grasping ends of the forceps. These partial passages form a complete passage when the forceps are closed, allowing the forceps to be guided by the 'flexible (j-wire) guide'. The closed forceps are passed into the opening created by the syringe/needle/dilator and then opened and closed, rotated, opened and closed, rotated, etc. . . . until such time as the opening created is of sufficient size and shape.

Drawbacks of the forceps are that they act in a single plane at any one time; they do not have a stop (limit of travel); and their orientation and range of motion is dependent on the strength and skill of the surgeon.

Blue Rhino Trach

The 'Blue Rhino Trach (BRT)' is a tapered plastic tool with an angled tip, which includes an internal passage to be guided by the 'flexible (j-wire) guide'. The 'BRT' is passed into the opening created by the syringe/needle/dilator and then pushed and released, pushed and released, pushed and released, etc. . . . until such time as the opening created is of sufficient size.

Drawbacks of the 'BRT' are that the lateral spread is achieved through a high insertion force, by the tapered outer diameter of the device; and this high insertion force and resultant deflection takes the tip of the device dangerously close the anterior (far) wall of the trachea, where damage which can lead to fatal infection can occur to the patient.

Blue Dolphin Trach

The 'Blue Dolphin Trach (BDT)' is an un-deployed reinforced plastic balloon in a delivery tube, which includes an internal passage to be guided by the 'flexible (j-wire) guide'. The 'BDT' is passed into the opening created by the syringe/needle/dilator and then inflated, to create an opening of sufficient size.

Drawbacks of the 'BDT' are the 'explosive force involved in deployment within the patient; the danger of certain accompanying equipment in the operating arena; and the risk of the balloon bursting or becoming loose inside the patient.

Percu-Twist

The 'Percu-Twist' is a screw-like tool which includes a partial passage to be guided by the 'flexible (j-wire) guide'. The Percu-Twist' is passed into the opening created by the syringe/needle/dilator and then, rotated, rotated, rotated, rotated, etc. . . . until such time as the opening created is of sufficient size.

The chief drawback of the Percu-Twist' is the excessive torsional load placed on the tissue of the patient's trachea during application of rotary motion, causing the tissue to 'wind up' around the tool during its use. It also takes as much time to remove as to deploy.

Trocar

A 'Trocar' can be an un-deployed reinforced stent in a delivery tube, which includes an internal passage to be guided by the 'flexible (j-wire) guide'. The 'Trocar' is 'shot' into the opening created by the syringe/needle/dilator whereupon it expands and stabilizes, to create an opening of sufficient size.

Drawbacks of the 'trocar' are the 'violent force involved in a deployment within the patient; the danger of range of motion in use; the risk of the non-deterministic and incorrect location in the patient. It is also subject to removal difficulties.

In the previous examples, some of the dilators will always retain the 'flexible (j-wire) guide', since they are effectively cylinders into which the flexible (j-wire) guide' is threaded, during the first stage of dilation.

The Griggs Forceps can 'lose' the 'flexible (j-wire) guide' when they are opened. If, for some reason, it is desired to re-engage the 'flexible (j-wire) guide', the forceps may be removed from the orifice, closed, re-threaded, and re-inserted.

The background discussed here is limited to particular application of dilators in percutaneous tracheotomies and tracheostomies. Similar dilators are used to create other types of openings in other medical and veterinary applications, as well as industrial applications.

It is not meant for the invention described herein to be limited in its application to percutaneous tracheotomies and tracheostomies, based on the background information provided here.

BRIEF DESCRIPTION OF THE DRAWINGS

FIG. 34A through E are progressive views of a dilator constructed from a single piece, flexible housing, with an end mounted handle partially folded to prepare to actuate. (100)

LISTING OF ELEMENTS PRESENTED IN THE DETAILED DESCRIPTION

Figure 1:
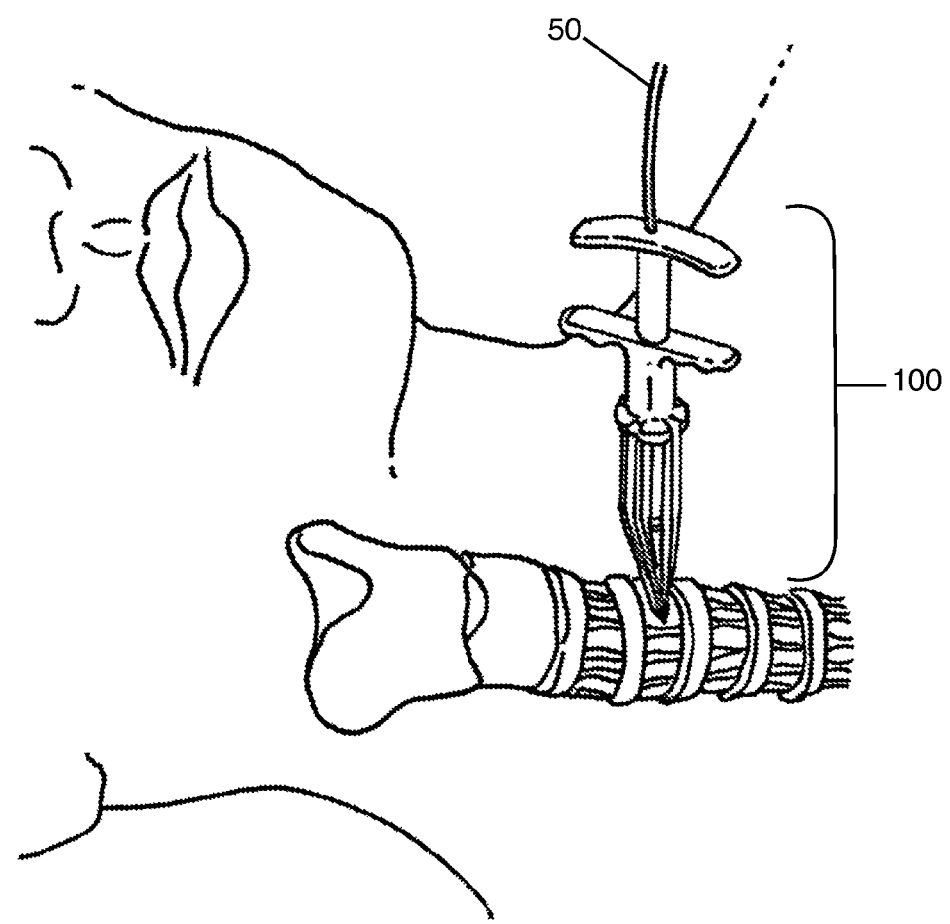
FIG. 1 is a diagram of a dilator inserted between cartilage rings, of a human trachea. (50,100)

50 Threadable 'flexible (j-wire) guide' (1,2,6,7,20,21,22, 24, 25a 28,29,30a,30b,30c,31,32, 37,41ab,42ab)
100 Dilator device (1,2,5,13c,19a,19b, 20,23,34,)
200 ACTUATION MEANS (Translating Inner Rod) (2,13c,19a,19b, 20,21,22,23,)
300 Inner Slider Rod (2,3,5,6,9,10b,12,13a,13b,19a,19b, 22,23,27,)
310 First End, Inner Slider Rod (3,21,)
320 Handle, Inner Slider Rod (3,4,6,13a,)
322 Handle Gripping Surfaces, Inner Slider Rod (2, 4,)
330 Mechanical Linkage Assembly for Handle (20)
340 First Link/Handle (19a,19b, 20,21,)
342 Textured Outer Surface, First Link/Handle (19b,21, 27,)
345 Pivot Point, Handle (19a)
350 Second (Intermediate) Link/Handle (19a, 20, 21,)
360 Second End, Inner Slider Rod (3,14a,22,)
370 End Face, Inner Slider Rod (3,9,)
372 Perimeter Edge, Interfaces with Spreader Means (9,10a,14a,15c,16,)
374 Tapered surfaces to Inner Passage Way, Inner Slider Rod (10a,13a,16,23,)
376 Passage Way, Inner Slider Rod (10a,13a,15c,16,21, 23,)
378 Exit, Inner Slider Rod Passage Way, Offset from a Center (6,13a,)
380 Key on Inner Rod, for Outer tube keyway (KM1a) (3,9,12,)
382 Tactile Feature, Raised bump on Inner Rod (9,12)
383 Visual Feature, on Inner Rod (w.r.t. Outer Tube) (14b,)
384 Key on Inner Rod External to Slider Arm/Spreader Arm Assembly/Spreader Means (9,10c,)
386 Key on Inner Rod Internal to Slider Arm/Spreader Arm Assembly/Spreader Means (10b,)
390 LED Unit, in Inner Slider Rod (2,7,9,24)
400 Intermediate Sleeve (for threadable 'metal guide') (7,20, 21,22,23,24, 25a 26,28,29,30a,30b,30c, 37,41a, 42a)
410 First End, Intermediate Sleeve (26)
412 Bulb Feature, Intermediate Sleeve (23)
414 Conical Feature, Intermediate Sleeve (28)
416 Overlapping Conical Features (Overlaps Spreader) (29)
418 Bridging Tab Features, Intermediate Sleeve (25a 30a, 30b,30c,37)

440 Integral Retainer Ring Element, Intermediate Sleeve (26)
445 Integral Retainer Ring Element, Slider Arm Openings (26)
450 Internal Passage, Coaxial (26a)
460 Second End, Intermediate Sleeve (26a)
470 Curved Tip on Intermediate Sleeve (25A, 25C)
500 Outer Slider Tube (2,3,5,6,8a,8b,13a,13b,14b,19a, 20, 21,22,23,24, 27,)
505 Key Element, Outer Slider Tube to Slider Ring (11,)
510 First End, Outer Slider Tube (2, 3,19a,21,22,)
511 Handle Mount Position, near Outer Slider Tube first end (21,)
514 Key Element in Attachment Feature, for Slider Ring (14b,19a,19b,)
520 Tactile Detent Feature, w.r.t. Inner Rod (8a, 8b,11, 12,)
532 Handle Element, Outer Slider Tube (2,4,6,8a,12,13a,)
533 Textured Surface, Outer Slider Tube Handle Element (4)
550 Key for Inner Rod, in Outer Slider Tube (KM1b) (8a,8b,12,)
560 Textured Surface, on Outer Slider Tube (19b,)
570 Second End, Outer Slider Tube (19a,21)
580 End Cap (19a,20,)
582 Extension of Outer Slider Tube (19a,)
585 Pivot Point, End Cap (19a,)
600 Slider Ring (3,5,8a,12,13a,13b,14b,16,19a,19b,20, 21,22,25a,31,32,)
606 Key Element, Slider Ring to Outer Tube (11,14b,19a, 19b,)
610 Pins, Slider Ring to Slider Arms/Spreader Means (8a,12,15c,)
700 SPREADER MEANS (2,13c,19a,19b,20, 21,22,23,)
781 RFID Chip (in Spreader) (2,7,24,)
782 RFID Chip in Actuator Means (2,4,7,19b,24,)
783 Dissolvable Identification Marking Barcode/Glyph (4,7,19b,24,)
800 Slider Arm (2,3,4,5,10b,10c,13a,13b,14a,15b,15c,16, 18a,18b)
810 First End, Slider Arm (3, 4, 21,22,)
820 Pivotally Attached, Reverse Hooking Feature (2,)
822 Keyed features mate with threadable guide sleeve (25B)
840 Tactile Detent Contact Surface (14a,)
842 Arcuate Contacting Surfaces (3,)
844 Constant Slope contacting surfaces (4,)
846 Maximum Predetermined Position (Non-Equidistant) (17)
850 Visual markings (14a,)
860 Arrest Shoulder (3,)
865 Retaining ring feature (13a,)
870 Tactile Retaining Circumferential Detent Depression (2, 3, 4, 15a,15b,18a,18b,)
880 Inner Passage relief for 'metal guide' & sleeve (18a)
890 Straight Tip, Slider Arm (15b,15c,)
892 Curved Tip, Slider Arm (15a,15b,15c,16,18a,18b,)
895 Keying Features on Slider Arm surface, w. IS Rod (10b)
896 Florescent colored tips of spreader arm limbs (13b, 15a,15b,18a,18b,)
1201 Retaining Ring (2,5,6,22,23,)
1230 Molded on retainer material (31, 32)
1300 Return Spring
1800 Spreader Arm Assembly (20,22,24, 25a)
1820 Pivotally Attached, Reverse Hooking Feature (20)
1824 Plurality of Spreader Arm Limbs
1830 Spreader Arm Limb (20, 25a)
1842 Arcuate Contacting Surfaces (22,)
1844 Constant Slope Contact surfaces (21,)
1860 Arrest Shoulder (21,22,)
1865 Retaining ring feature (21,)
1870 Tactile Retaining Circumferential Detent Depression (20,22, 25a,27,28,29,30c,31.32,)
1894 Keying Features on Spreader Arm Limb Tip, w. Intermediate Sleeve (30a, 30b,)
1896 Florescent colored tips of spreader arm limbs (20, 23,24,)
4240 FEEDBACK MEANS (Actuator Segment to Spreader Segment, Unit Housing)
4300 Inner Slider Rod Segment (34,37,38abc,39,41ab, 42ab)
4340 First Handle Link Segment (34,3839)
4350 Second Handle Link Segment (34,3839)
4360 Markings, Position, Visual Feedback, Inner Slider Rod Segment to Outer Slider Tube Segment (38abc,39 (34,))
4370 End Face, Inner Slider Rod Segment (34,)
4374 Tapered Lead In, Inner Slider Rod Segment (39)
4376 Inner Passageway, Inner Slider Rod Segment (34 39)
4384 Keyway for Spreader Element, Inner Slider Rod Segment (34 38abc)
4390 Light Source, Inner Slider Rod Segment (39)
4500 Outer Slider Tube Segment (36b,37,38abc,39,41ab, 42ab)
4550 Key, Outer Slider Tube Segment to Inner Slider Rod Segment (36b)
4782 RFID Chip, Communications Means (39)
4783 Marking on Component, Feedback Means (39)
4800 Slider Arm Limb Segment (37)
4830 Slider Arm Limbs (26ab,37,38abc)
4842 Arcuate Contacting Surfaces wKey on SAL Element w. I
4844 Constant Slope Cntct Surfaces wKey on SAL Elmnt w. ISR
4870 Tactile Retaining Circumferential Detent Depression (34,3839,41ab,42ab)
4886 Slider Arm Limb Key, for Inner Rod Segment Interface (36b)
4894 Slider Arm Limb Key, for Intermediate Sleeve Interface (36ab,37)

BRIEF DESCRIPTION OF THE INVENTION

The present invention is a dilator which allows an operator to create an opening of desired size and shape, in a workpiece such as a human trachea. By example, referring to FIG. 1 the dilator is used to create a percutaneous opening in a human trachea. The invention features one handed actuation and includes several alternate handle and tip types.

Figure 2:
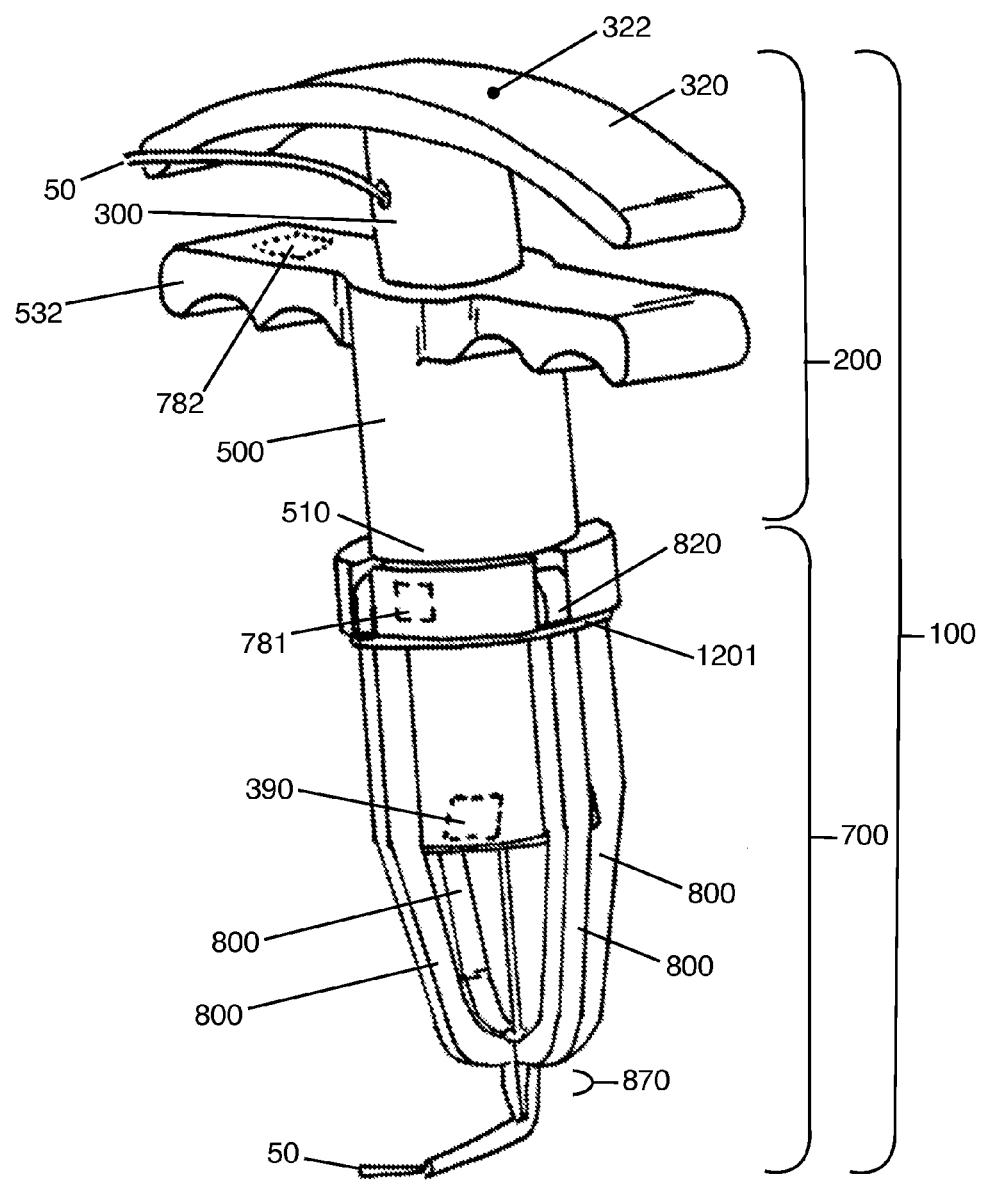
FIG. 2 is an isometric view of an 'un-actuated' dilator assembly with plunger style handle, showing an inner slider rod, an outer slider tube and a constrained 'metal guide' exiting off center. (50, 100, 200, 300, 700, 800,1201)

The preferred embodiment of the present invention, shown in FIG. 2, presents a dilator device which dilates an orifice. The dilator device includes at least an outer slider tube (500) containing an inner slider rod (300) with an affixed handle (320) and a keying element between the inner rod and outer tube. The outer tube, inner rod and handle are an integrated mechanical linkage sub-assembly (700) in this preferred embodiment, which creates an ergonomic advantage for the operator. This slider tube, handle, linkage sub-assembly is attached to a cluster of slider arms (800) commonly extending from a slider ring (600).

In summary, there are actuation means with different holding and handle configurations, some providing mechanical advantage. There are keying means, which keep all the respective elements in the device in proper relationship during operation and obviate the effects of manufacturing tolerances. There are spreading means, with alternate slider arm arrangements. There are gripping means, allowing the operator to hold and operate the device reliably. There are retaining means, wherein the mechanism is prevented from prematurely exiting the opening during dilation. There are feedback means, which provide redundant signals to the operator as the device is in use, to improve reliability.

Figure 3:
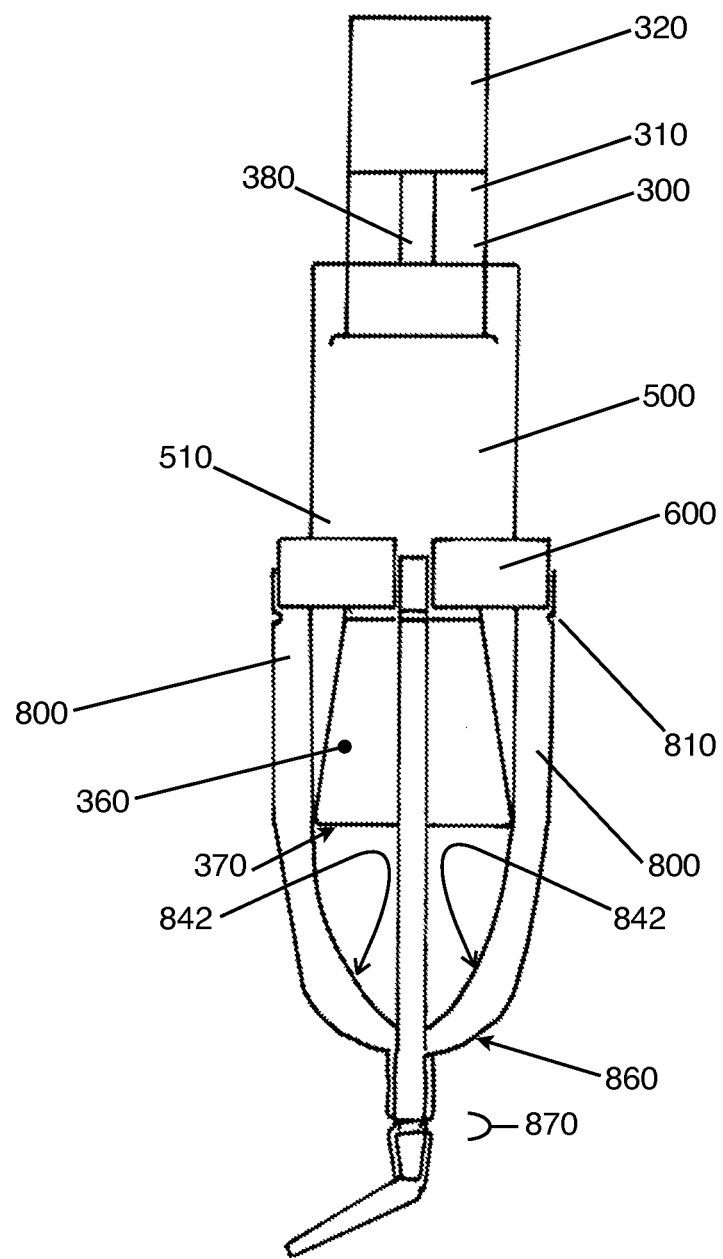
FIG. 3 is a side view of a dilator, showing variable arcuate surfaces inside one slider arm pair. (300,500,600,800)
Figure 4:
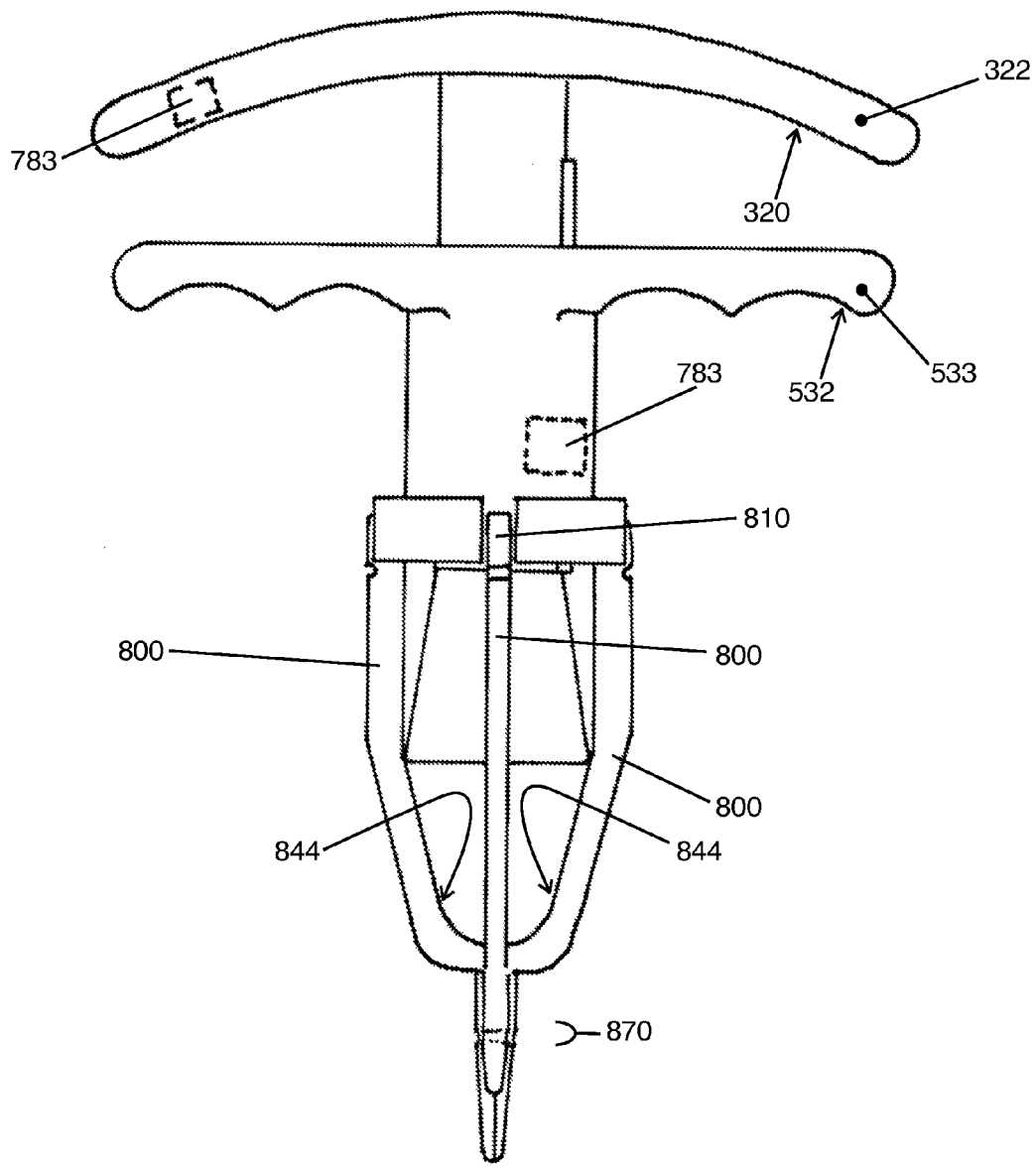
FIG. 4 is a front view of a dilator, showing constant slope surfaces inside another slider arm pair. (800)
Figure 5:
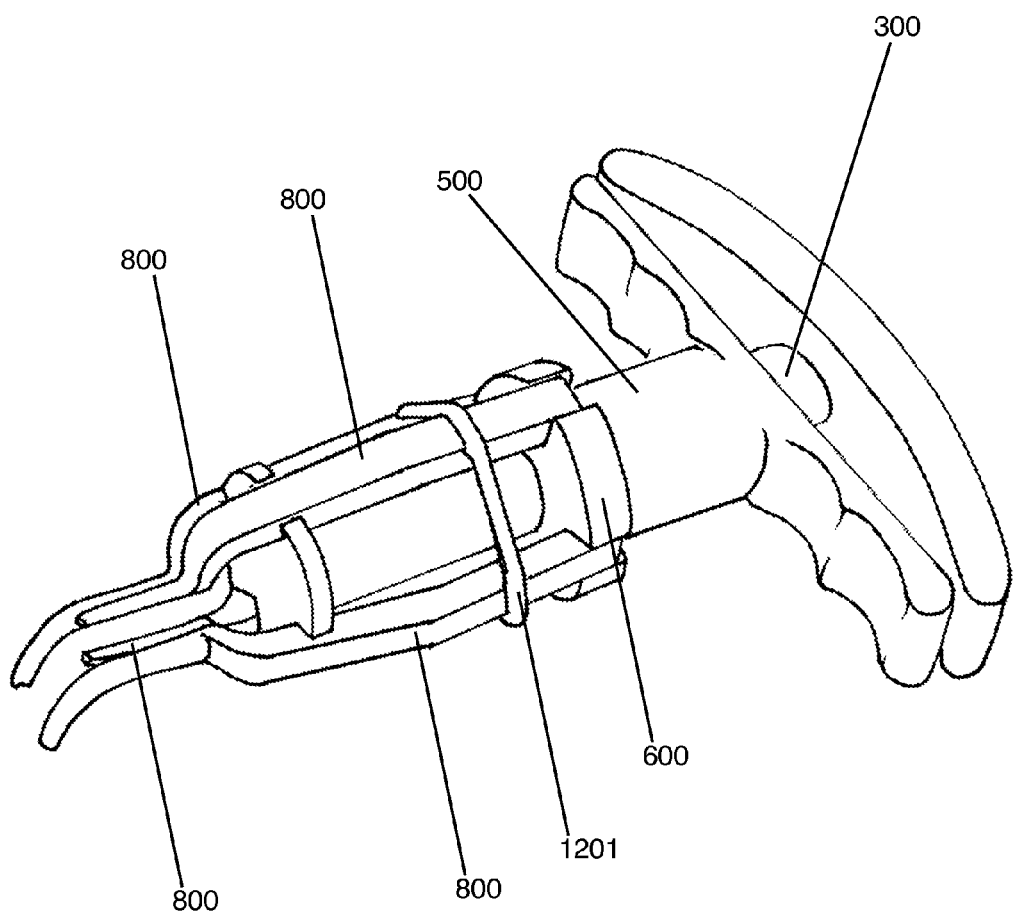
FIG. 5 is a photo of an 'actuated' dilator with plunger style handle at its end. (100,300,500,600,800,1201)
Figure 6:
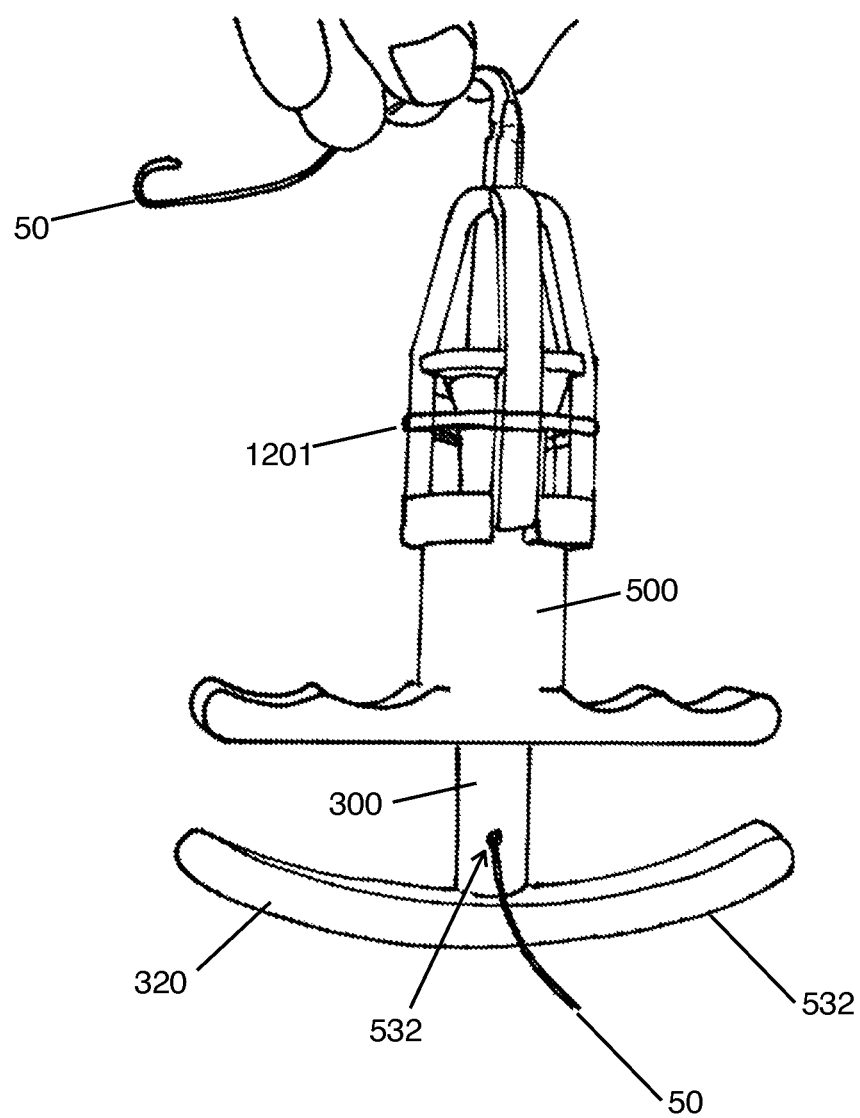
FIG. 6 is a photo of an 'un-actuated' dilator with plunger style handle at its end, and with a 'metal guide' passing entirely through it. (50,300,500,1201)

Alternate embodiments provide actuation means including but not limited to: a configuration without mechanical advantage, as shown in FIG. 3; a configuration with mechanical advantage at an end, as shown in FIG. 4A; and a configuration with mechanical advantage in the middle, as shown in FIG. 2. Furthermore, in some embodiments the device is formed as a single integrated component, as shown in FIGS. 5A through 5C, and FIGS. 6A through 6C.

Keying means are incorporated into these actuator embodiments, and extend from the actuator means to the spreading means. In other embodiments, the keying can extend still further from the spreading means, to an intermediate sleeve, which carries a threadable 'flexible j-wire guide'. Keying means extending from element to element through the entire assembly obviate the effects of manufacturing tolerances.

Figure 7:
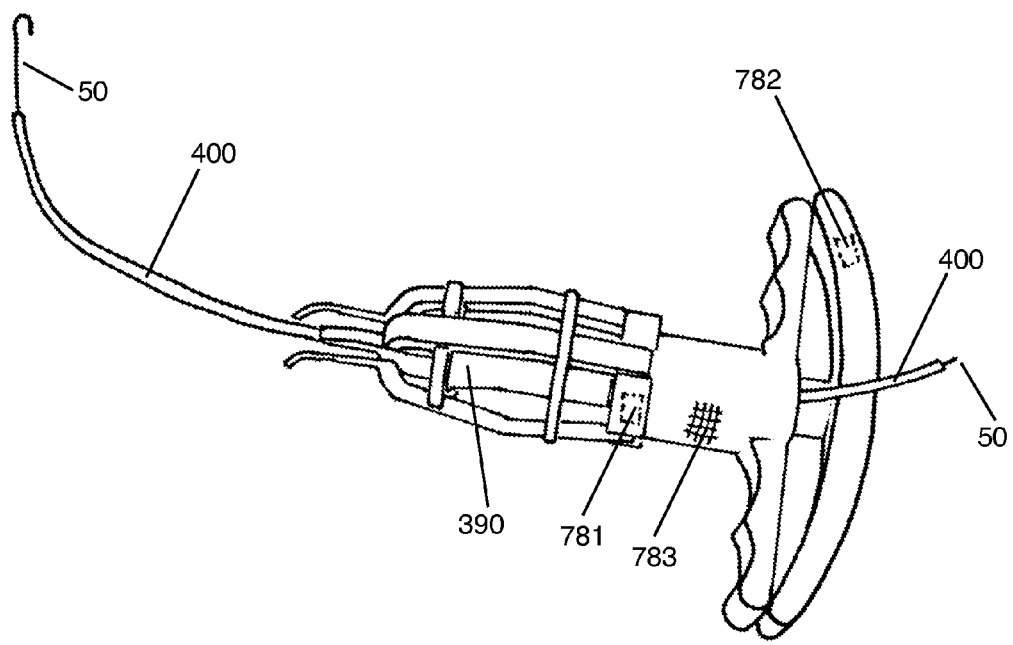
FIG. 7 is a photo of an 'actuated' dilator with plunger style handle at its end; and with a flexible sleeve carrying a 'flexible metal guide', passing entirely through it. (50,400)
Figure 8A:
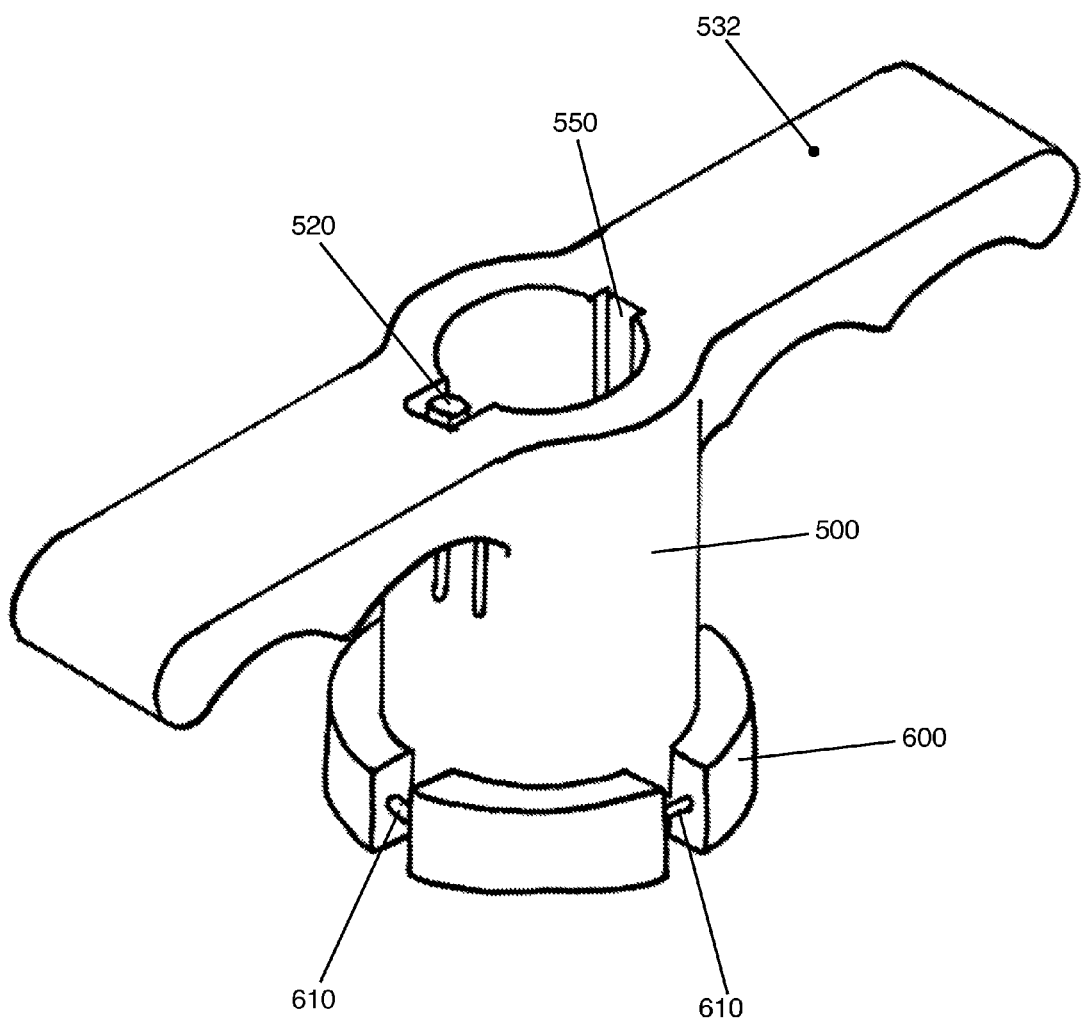
FIG. 8A is an isometric view of an outer tube with handle element, keying, tactile feedback and slider ring attachment features. (500,600)
Figure 8B:
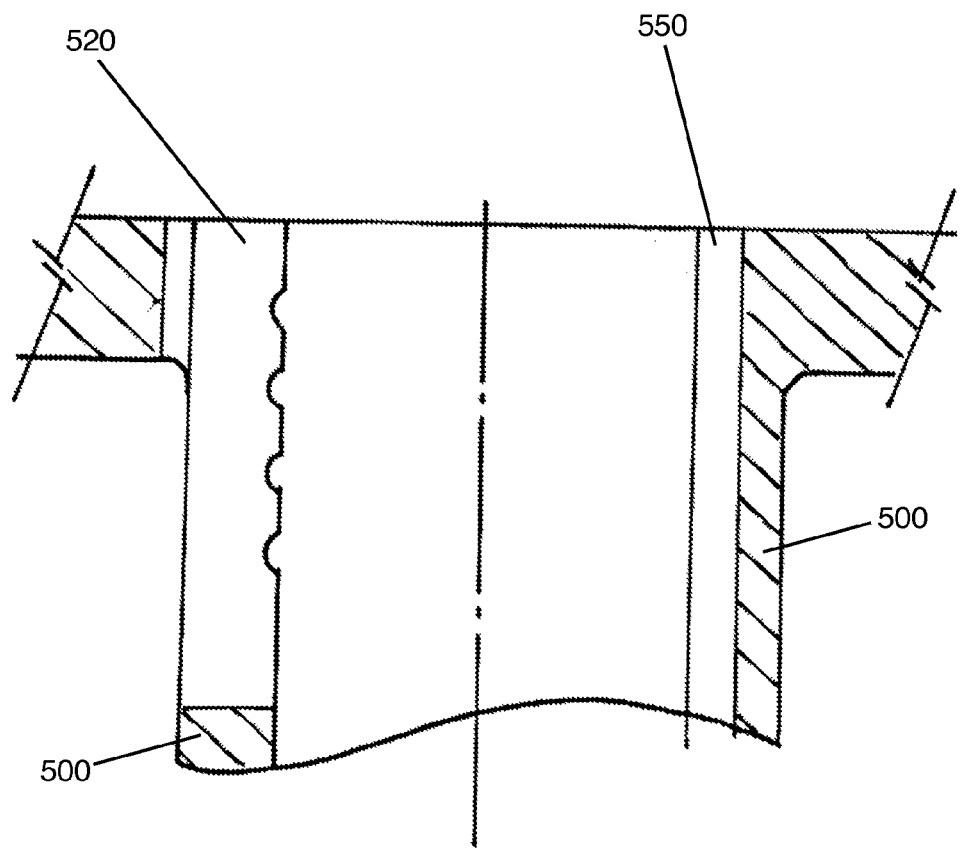
FIG. 8B is a partial section view of an outer tube with handle element, keying, tactile feedback and slider ring attachment features (500)

Various embodiments provide spreading means including but not limited to: grouped pairs of individual slider arms which are attached to a slider ring mounted to the outer slider tube as shown in FIG. 2; spreader arm assemblies which are to be attached to the outer slider tube as shown in FIGS. 7 & 8; and in some embodiments, the spreader arm assembly is formed as a single integrated component with the actuator elements, as shown in FIGS. 5A through 5C, and FIGS. 6A through 6C.

Figure 9:
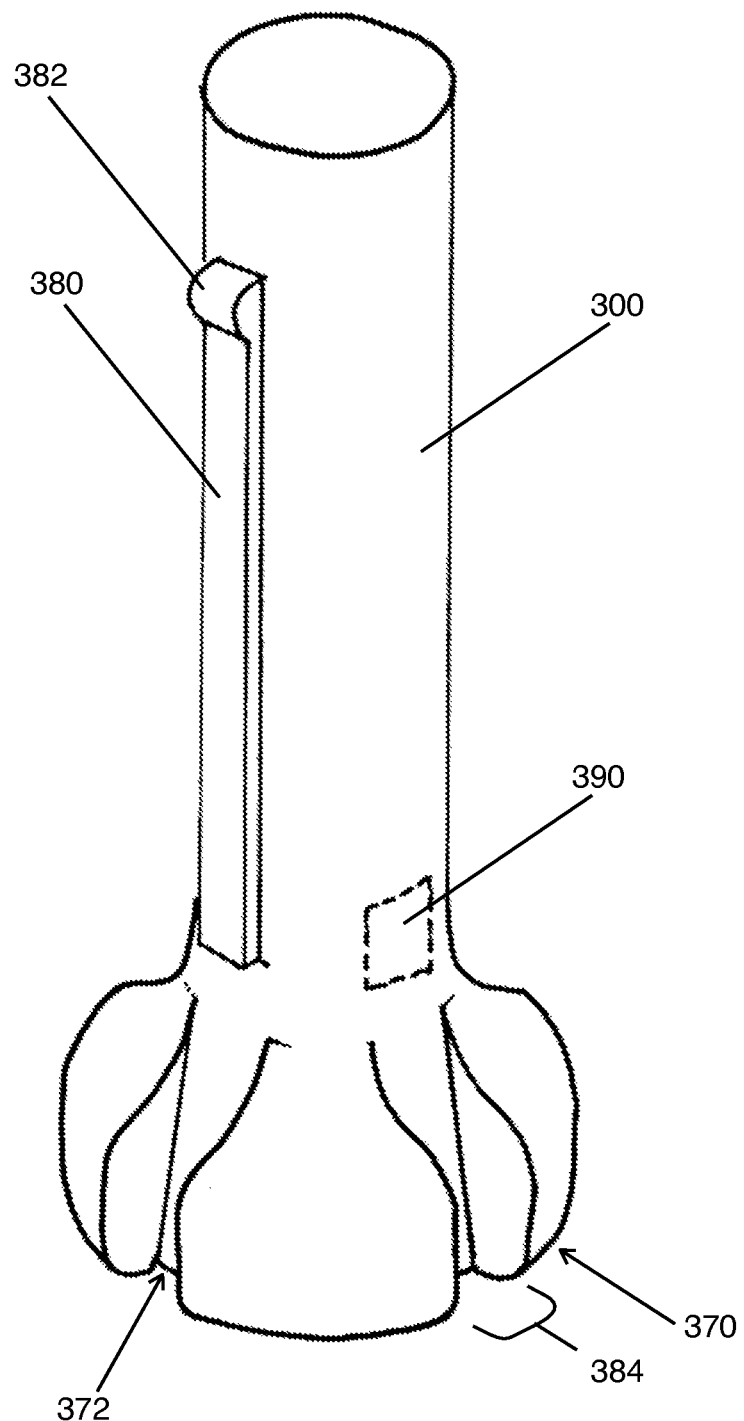
FIG. 9 is an isometric view of an inner slider rod showing keys for positioning in an outer tube and for slider arms, as well as tactile feedback. (300)

When using the preferred embodiment of the present invention for a percutaneous tracheotomy, a threadable 'flexible (j-wire) guide' is passed into a sleeve, held in and exposed from the slider arm assembly's tip and proceeds freely through an internal passageway in the dilator device, exiting a portal offset from the assembly's center as shown in FIG. 9.

Figure 10A:
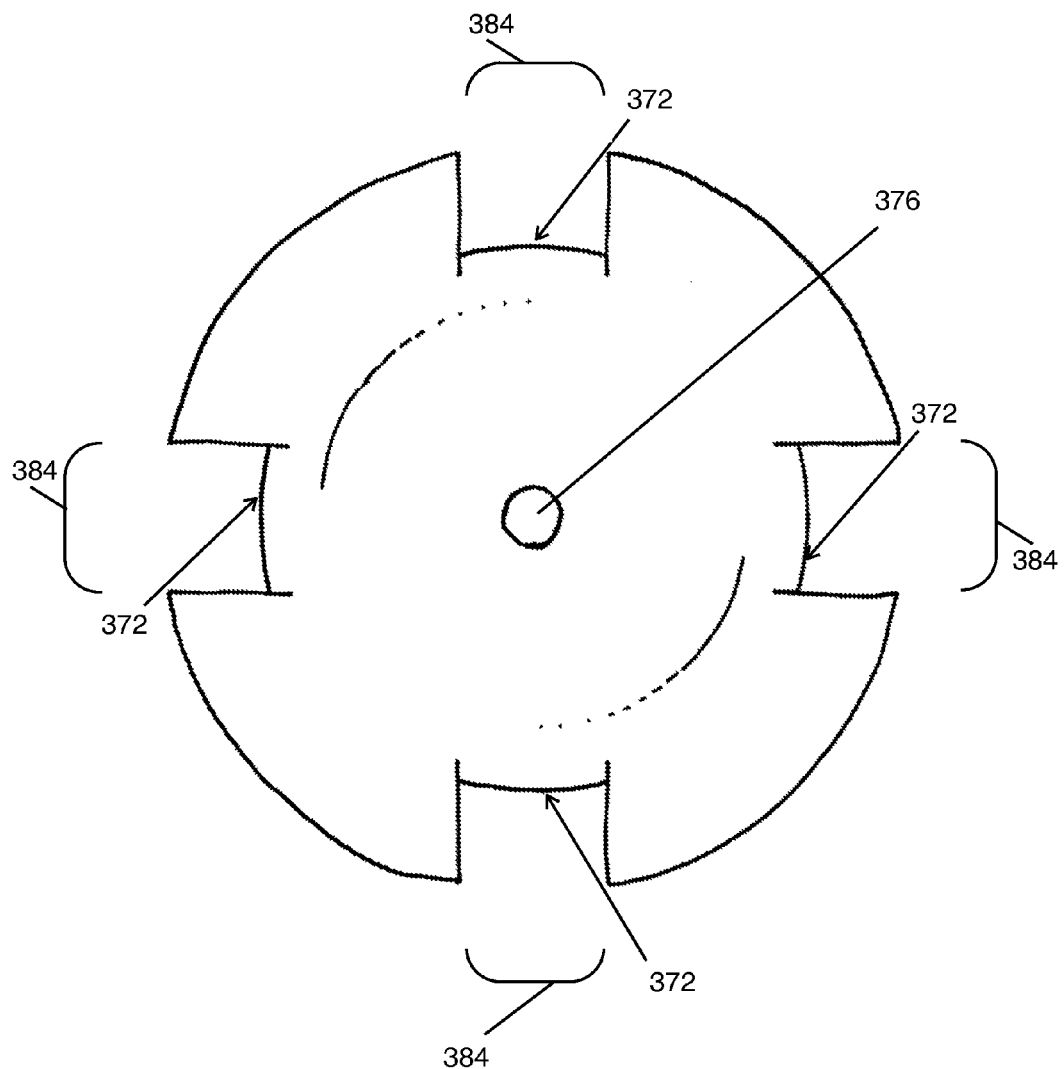
FIG. 10A is an end view of an inner slider rod showing keys for slider arm positioning, and a tapered entrance for collecting a 'metal guide'(and sleeve). (300)
Figure 10B:
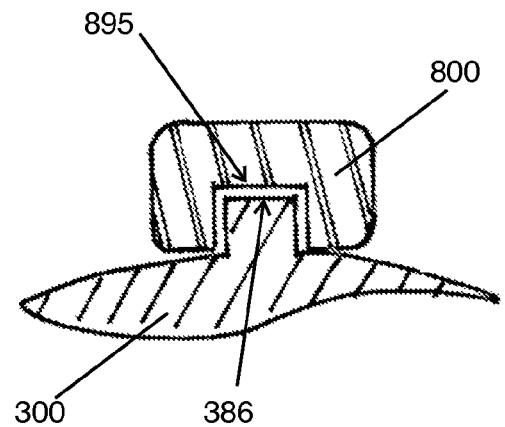
FIG. 10B is a partial section view of an inner slider rod showing a raised key for slider arm positioning. (300)
Figure 10C:
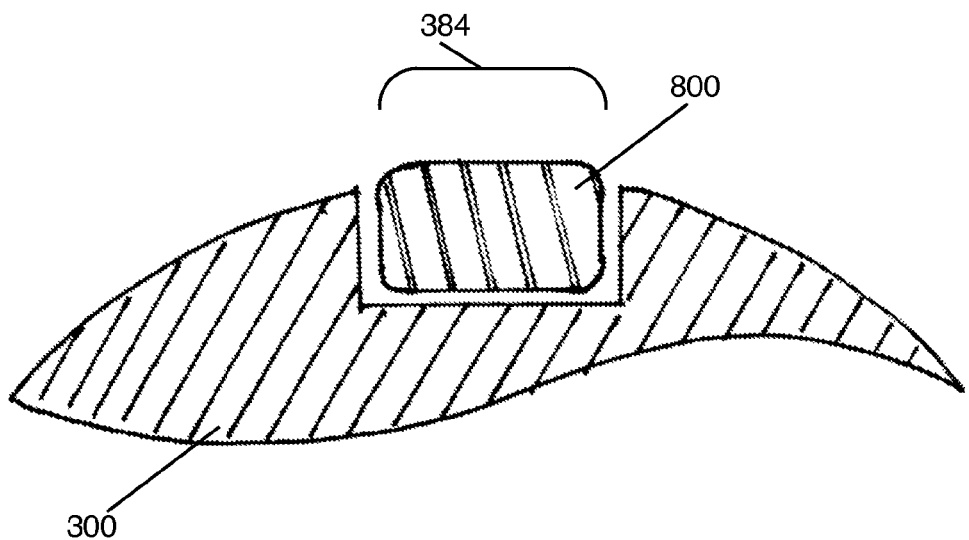
FIG. 10C is a partial section view of an inner slider rod showing a lowered key for slider arm positioning. (300)
Figure 11:
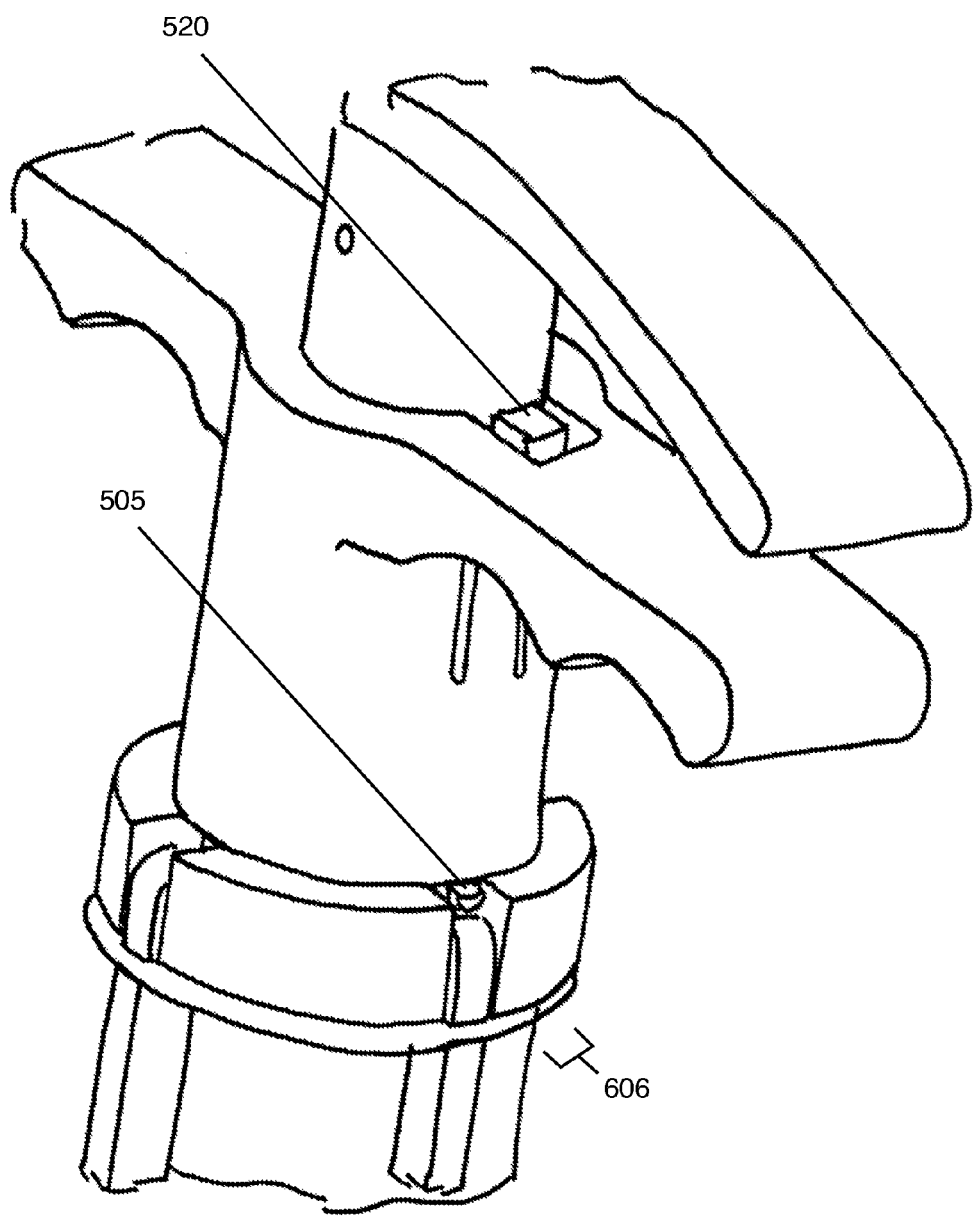
FIG. 11 is a partial isometric view of a dilator assembly showing an inner slider rod, an outer slider tube and the pivoting slider arms on a slider ring with retainer. (505,606)
Figure 12:
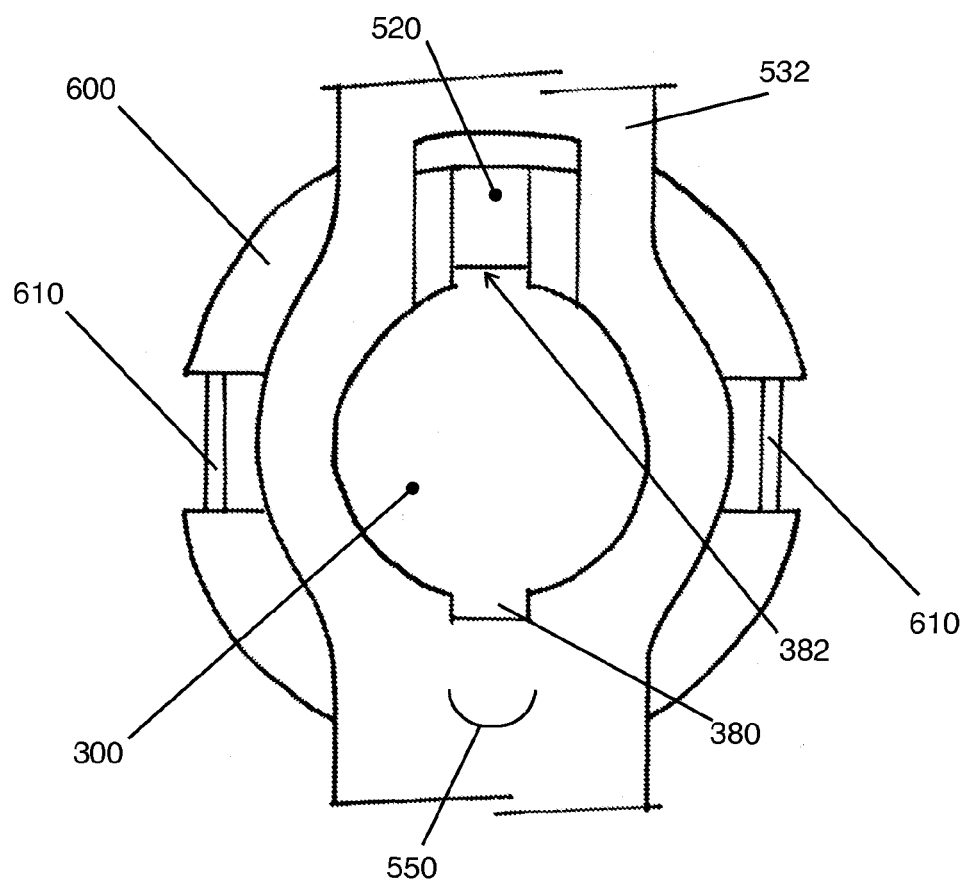
FIG. 12 is a cross section view of a dilator assembly showing an inner slider rod keyed to an outer slider tube to rotational alignment elements. (300, 500, 600)

In FIG. 1 the dilator device is guided on the 'flexible (j-wire) guide' (50), toward a pre-existing opening. The slider arms on the dilator device include feedback means wherein the dilator device is inserted into the opening until a circumferential tactile detent depression feeds back to the operator that the device is in the desired axial position for deployment. This circumferential detent feature (900) shown in FIG. 2 is gripped between cartilage rings. Additional feedback means include but are not limited to tactile and visual signals generated during the relative motion of the inner slider rod against the inside of slider arms as shown in FIG. 10.

When the dilator is detected to be in position, as tactile signals indicate the circumferential groove (900) is aligned with the cartilage rings, referring to FIG. 2; the operator first squeezes the handle (320) attached by linkage to the inner slider rod (300). This in turn pushes on the slider arms (800), driving them outward, to retain the dilator assembly in the orifice. The operator continues to squeeze the handle attached to the inner slider rod which in turn pushes the slider arms outward, until they reach their maximum predetermined positions.

During the time the inner slider rod (300) is travelling, tactile and visual feedback is provided to the operator as regards the degree of dilation which has been achieved.

The entire assembly can be biased with a return spring, or elastic retaining ring or elastic retaining ring with integral 'flexible (j-wire) guide' tube, to provide closure upon release of actuation force by the operator.

There are communication means, to allow the device to interact with other elements of an environment in which the device is used. RFID chips or other elements such as barcodes are integrated into the assembly in certain embodiments, for traceability and interaction with information systems in an operating arena. Materials which degrade after exposure to tissue are used in certain embodiments, to prevent unauthorized reuse.

There are illumination means, to improve visibility as a form of feedback. Point of use lighting is integrated into the assembly in certain embodiments, to improve accurate use.

It is possible to create the entire device from a single piece of polymer material, with flexible areas where respective device elements hinge relative to one another ('living hinges').

DETAILED DESCRIPTION OF THE INVENTION

The present invention is a dilator (100) which allows an operator to create an orifice of desired size and shape in a workpiece. For example, the dilator can be used to create a percutaneous opening in a human trachea. The invention features one handed actuation and includes several alternate handle and tip combinations. Several variations of the instant inventions actuation means, keying means, spreader means, gripping means, retaining means, and feedback means are presented herein.

When the dilator is used to perform a percutaneous tracheotomy operation for embodiments of the invention described herein is preceded by identifying the area for the opening to be created; puncturing the area between sterna notch and cricoid (tracheal) cartilage rings with a syringe and needle; removing the syringe from the needle, where the needle remains in place; and passing a 'flexible metal guide' into and through the needle.

This 'flexible metal guide' (also known as the 'metal guide') then remains in place for the duration of a typical percutaneous tracheotomy procedure.

Once this 'metal guide' is in place in the orifice, the needle is removed from the guide and the guide's free end is threaded into a passageway of the dilator device.

Figure 20:
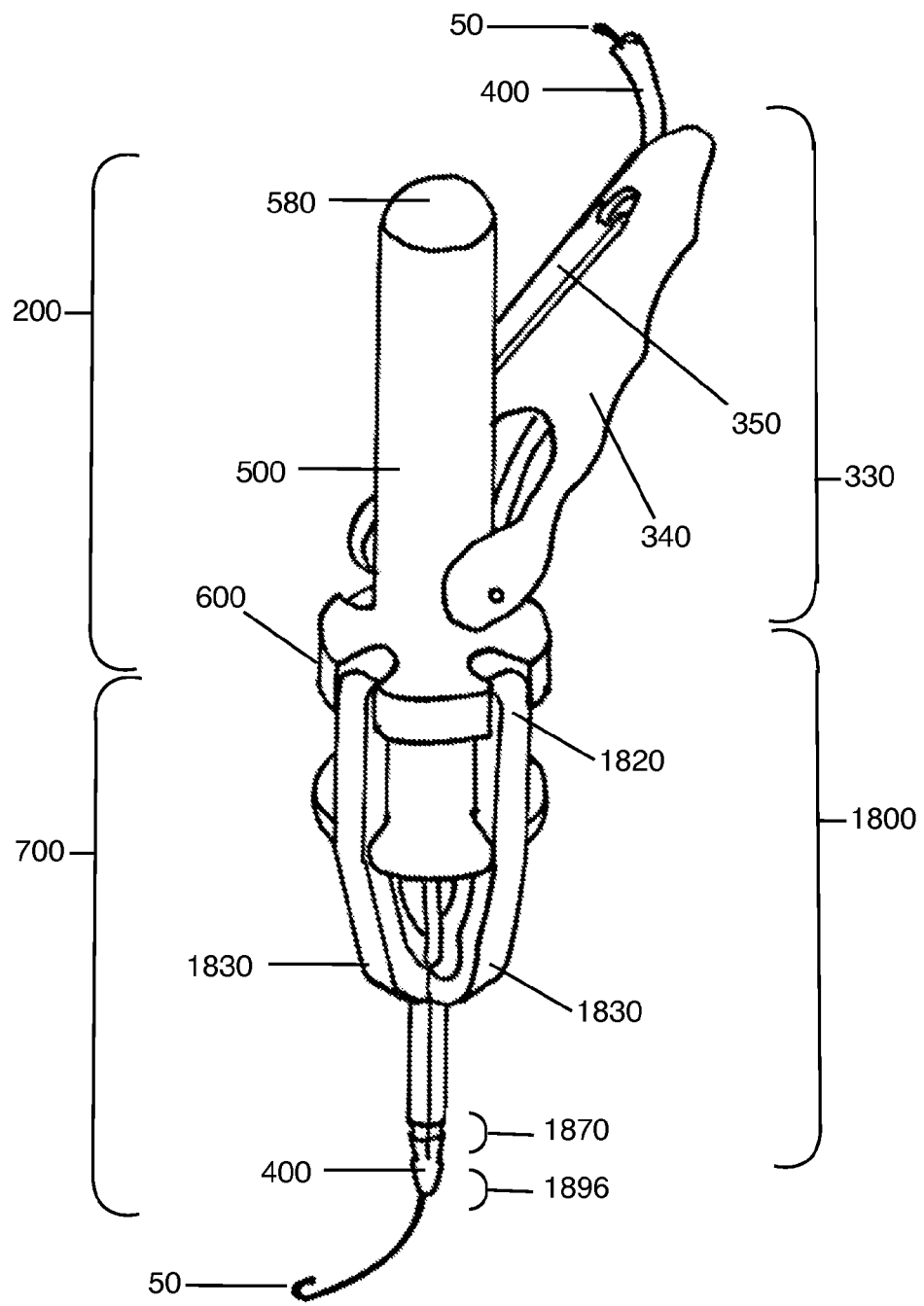
FIG. 20 is an isometric view of an 'un-actuated' mechanical linkage connected to an inner slider rod within an outer slider tube, with a mid-section mounted first link handle and a second link, with a full complement of slider arms containing an intermediate sleeve and metal guide. (100,200, 400,500,700,1800)

The preferred embodiment of the dilator (100), shown in at least FIG. 20, has actuation means (200) including at least an actuator sub-assembly with a mechanical linkage (330) mounted near the middle of the dilator (100) and spreader means (700)) including at least a spreader arm assembly (1800).

An alternate embodiment of the present invention is shown in FIG. 2, and has actuation means (200) including at least an actuator sub-assembly operated from an end of the dilator. This alternate embodiment further includes spreader means (700) which includes at least pairs of slider arms mounted on a slider ring. The metal guide (50) is threaded through the spreader means (700) and actuation means (200).

Figure 19A:
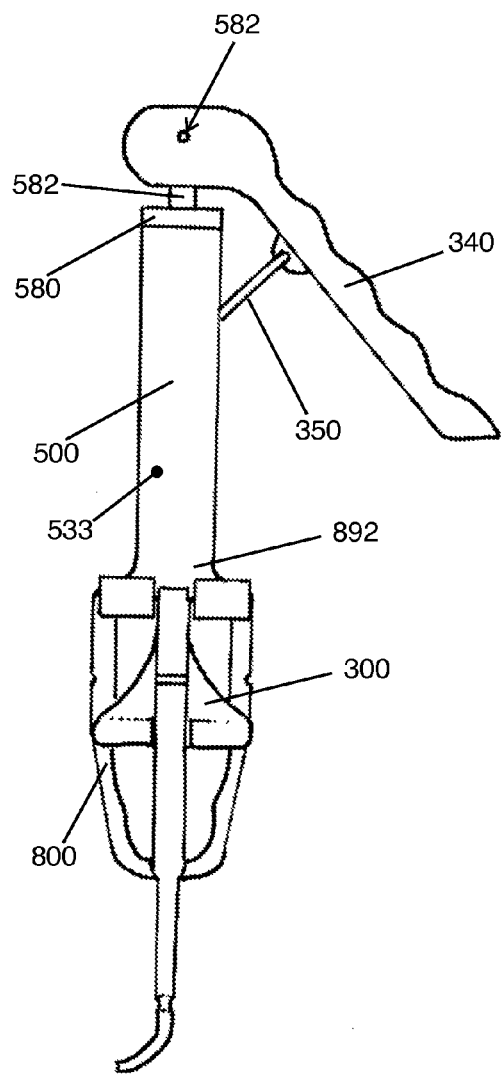
FIG. 19A is a side view of an 'un-actuated' mechanical linkage actuating an inner slider rod within an outer slider tube, with an end mounted first link handle and a second link. (100,200,300,500,700)
Figure 19B:
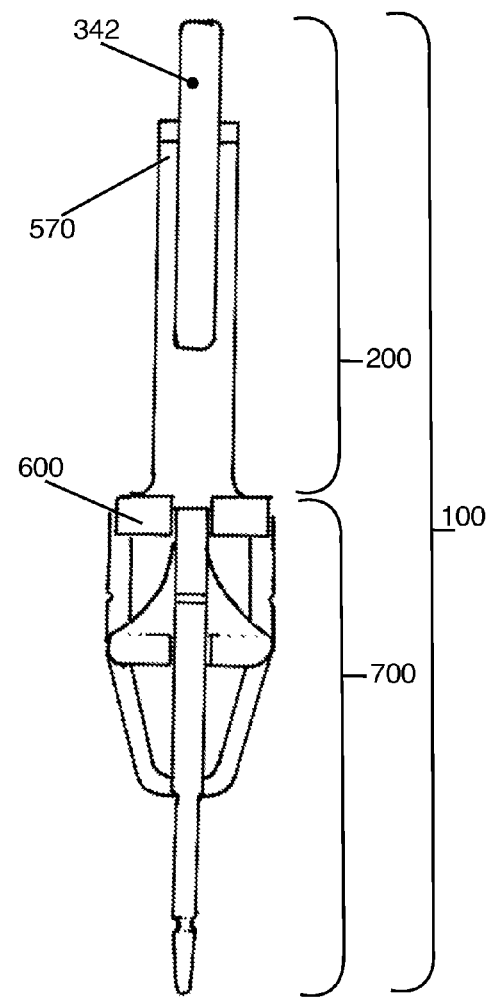
FIG. 19B is a front view of an 'un-actuated' mechanical linkage actuating an inner slider rod within an outer slider tube, with an end mounted first link handle and a second link. (100,200,300,500,700)
Figure 19C:
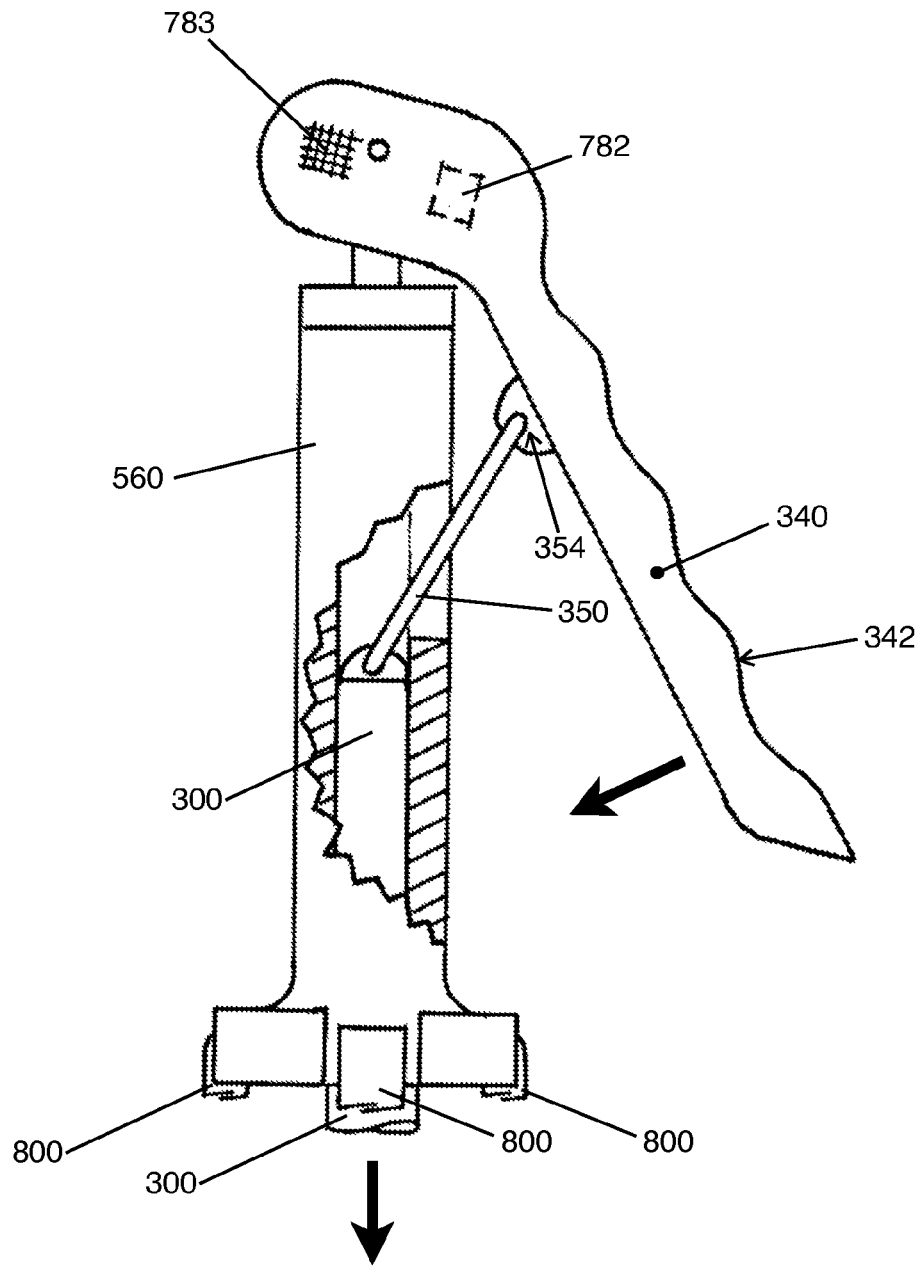
FIG. 19C is a side view of an 'actuated' mechanical linkage actuating an inner slider rod within an outer slider tube, with an end mounted first link handle and a second link. (100,200,300,500,600,700)

Yet another alternate embodiment of the present invention is illustrated in FIGS. 19A and 19B, where actuation means (200) includes at least an actuator sub-assembly operated from the end of the dilator (100). This alternate embodiment makes use of a variety of slider ring (600) attachment options as disclosed herein including where the slider ring is connected to slider arm pairs, as in the first alternate embodiment, or where the slider ring is a part of a spreader arm assembly, as in the preferred embodiment. This second alternate embodiment illustrates the incorporation of a unique mechanical advantage in the actuation means through the use of a handle linkage attached near an end of the dilator. This unique mechanical advantage can be applied to various permutations of the present invention.

Still another alternate embodiment, shown in FIG. 34, has end mounted handle segments of fixed length.

Figure 38A:
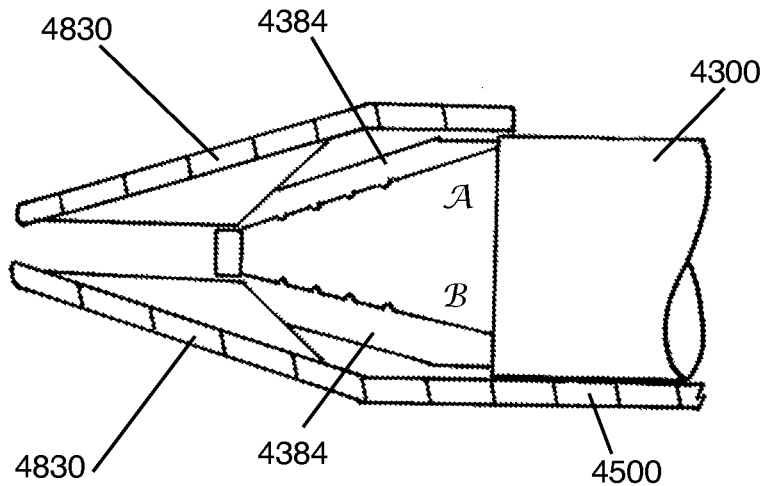
FIG. 38A is a section view of inner slider rod segment inserted into a spreader arm segment in an unactuated position (4300, 4800)
Figure 38B:
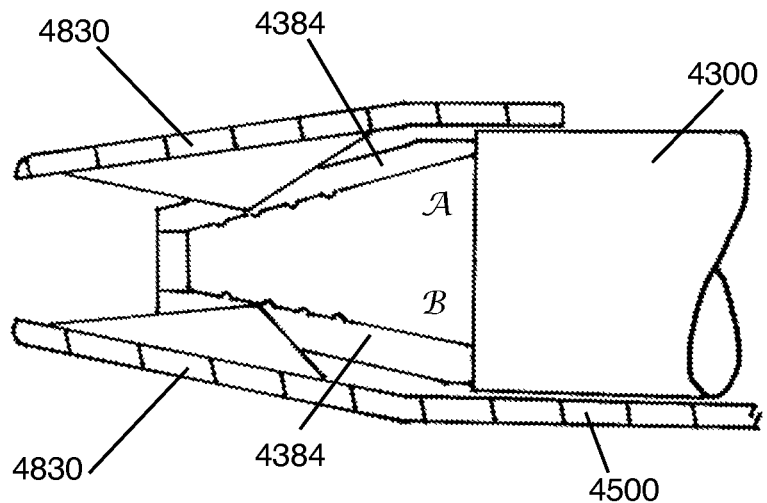
FIG. 38B is a section view of inner slider rod segment inserted and slid partly into spreader arm segment in a mid-actuated position (4300, 4800)
Figure 38C:
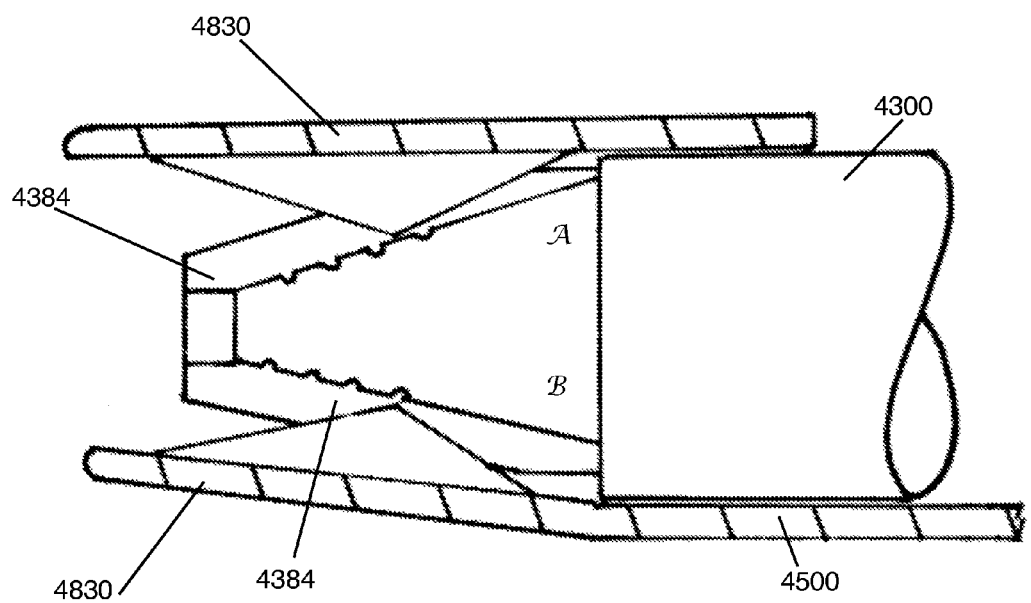
FIG. 38C is a section view of inner slider rod segment inserted into and slid fully spreader arm segment in an actuated position (4300, 4800)
Figure 39:
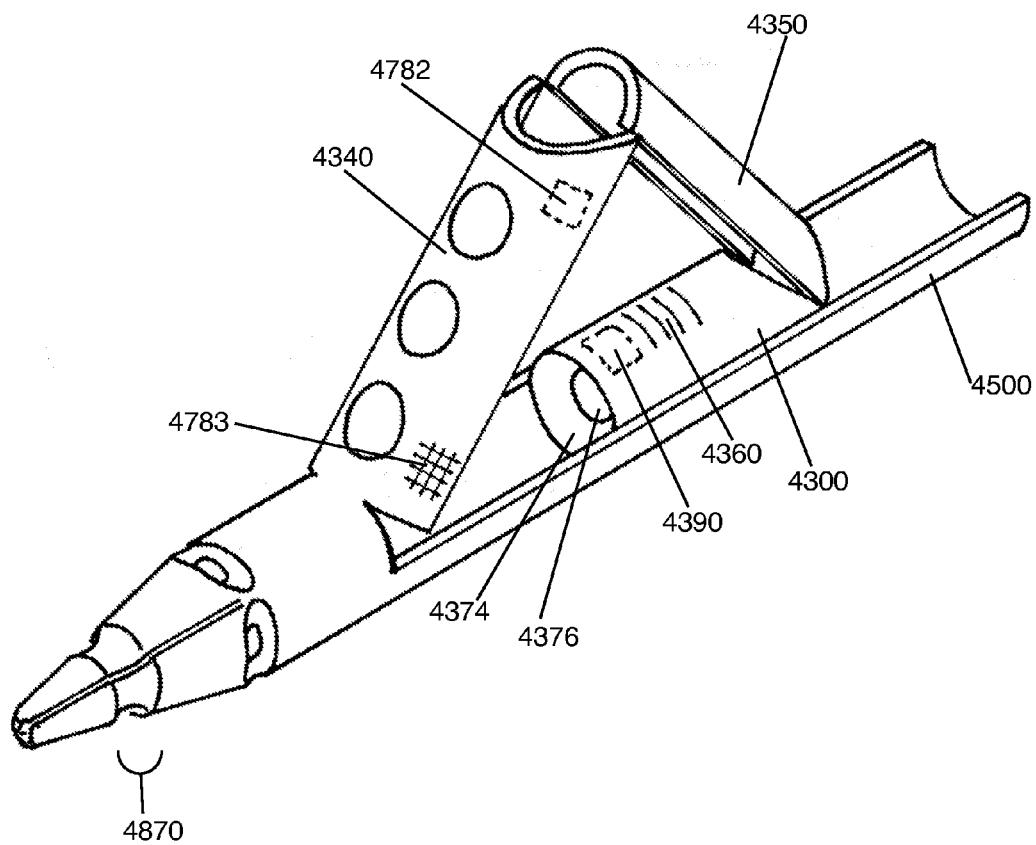
FIG. 39 is an isometric side view of major elements for a dilator constructed from a single piece, flexible housing, with a mid mounted handle. (100,4300,4500,4800)
Figure 40A:
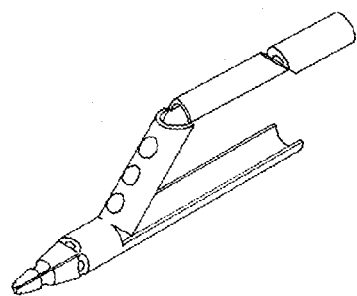
FIG. 40A through E are progressive views of a dilator constructed from a single piece, flexible housing, with a mid mounted handle partially folded to prepare to actuate.
Figure 40B:
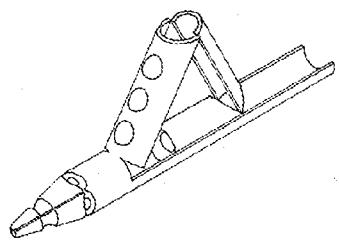
Figure 40C:
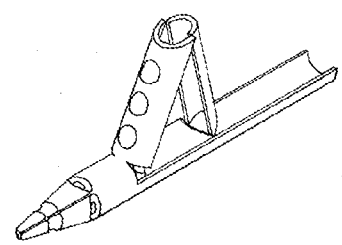
Figure 40D:
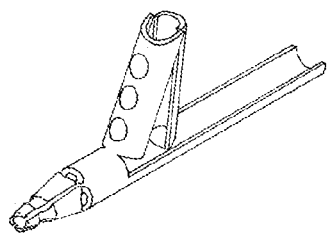
Figure 40E:
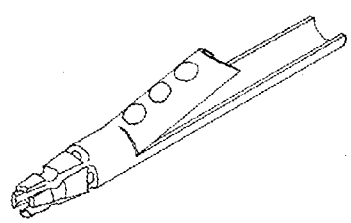
Figure 41A:
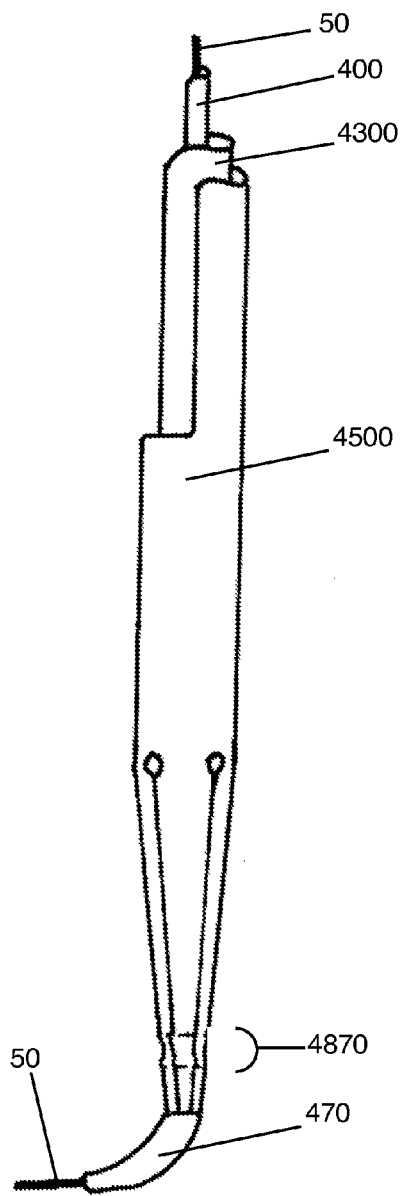
FIG. 41A is a side view of straight tipped spreader arm limbs holding a curve tipped intermediate sleeve contained a metal guide. (4800)
Figure 41B:
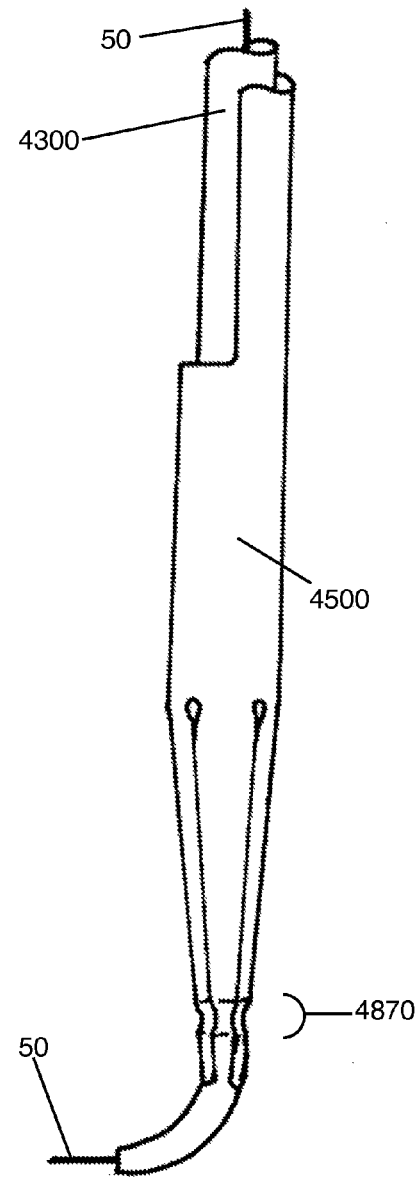
FIG. 41B is a side view of straight, and curve tipped spreader arm limbs holding a metal guide (4800)
Figure 42A:
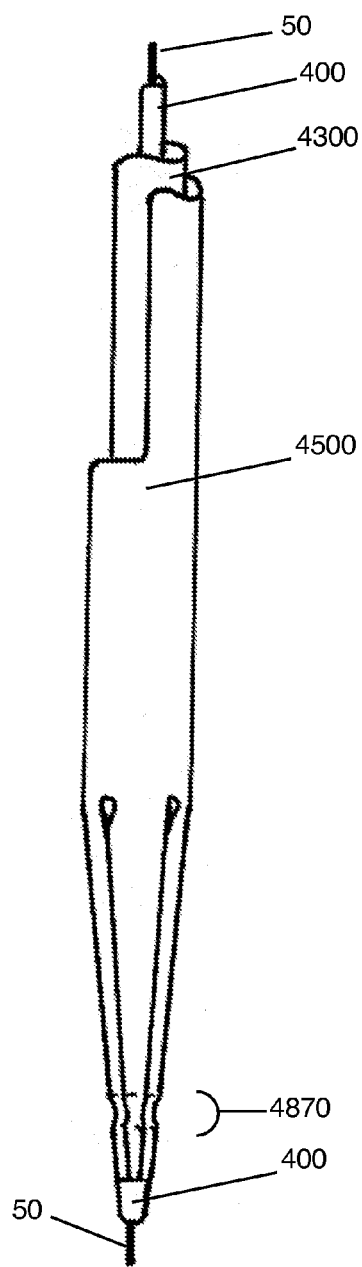
FIG. 42A is a side view of straight tipped spreader arm limbs holding a straight tipped intermediate sleeve contained a metal guide. (4800)
Figure 42B:
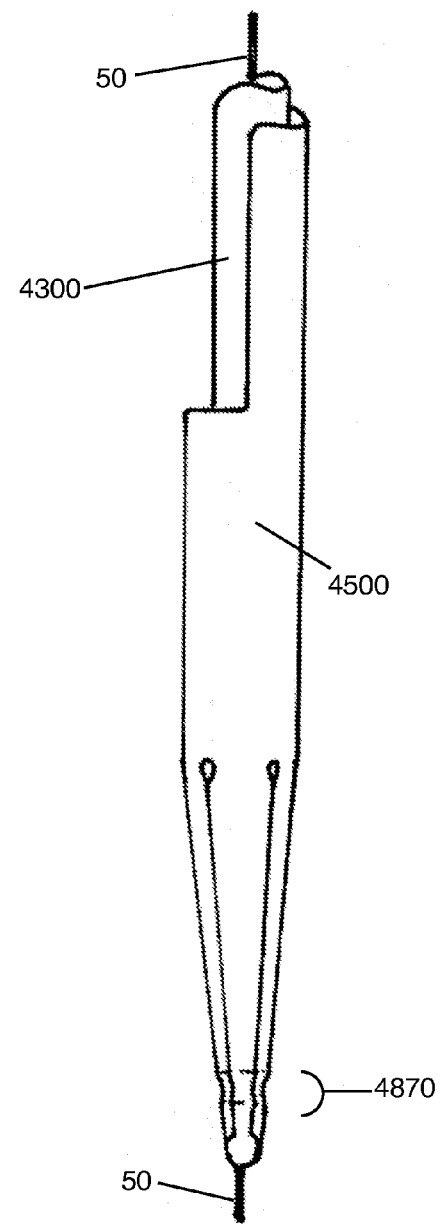
FIG. 42B is a side view of straight tipped spreader arm limbs holding a metal guide (4800)

Yet still another alternate embodiment, shown in FIG. 38, has mid mounted handle segments of fixed length. The various spreader means for the alternate embodiments shown at least in FIG. 34 and FIG. 38 are formed from a single piece housing, incorporate flexible areas, can be used with and without an intermediate sleeve, all have a unique mechanical advantage incorporated into their actuation means, and wherein respective device actuation means are provided by segments which hinge, pivot, fold and/or slide relative to one another. The spreader means of these embodiments are shown substantially integrated with the actuator means since the dilators are constructed from single piece housing. The actuator means of these embodiments can be formed from a single piece housing having a keyed interface for attaching a spreader arm assembly as further disclosed herein.

For the embodiments of the present invention presented herein, additional features and combinations of features of the dilator device are hereby further described including the actuation means, spreader means, retaining means, keying means, feedback means, gripping means, illumination means and communication means.

Preferred Embodiment

The preferred embodiment of the present invention includes actuation means (200), gripping means, spreader means (700), retaining means (1870), slider rod to slider tube keying means, slider tube to spreader arm keying means, slider rod to spreader arm keying means, spreader arm to intermediate sleeve keying means, feedback means, illumination means, and communication means.

Figure 21:
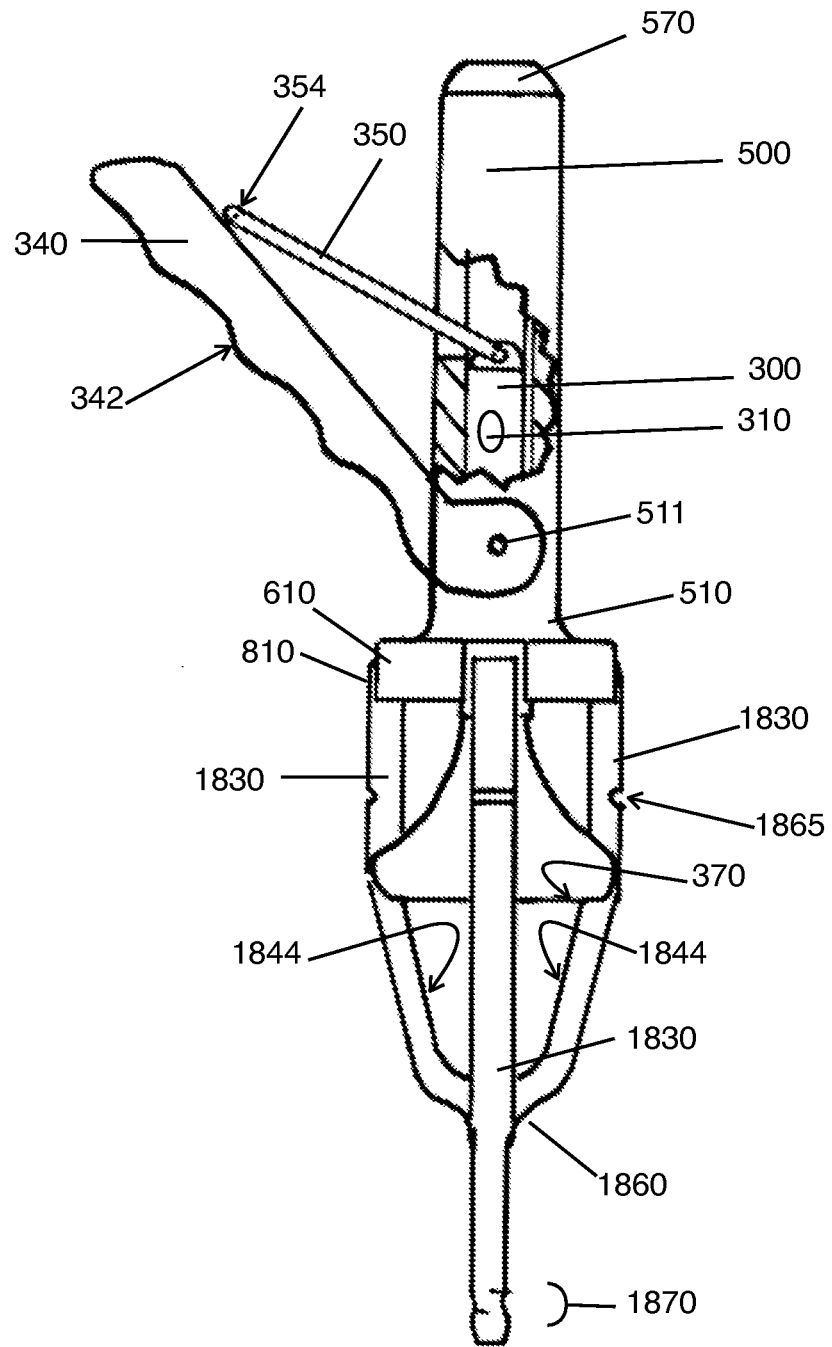
FIG. 21 is a side view of an 'un-actuated' mechanical linkage connected to an inner slider rod within an outer slider tube, with a mid-section mounted first link handle and a second link, with a full complement of slider arms containing an intermediate sleeve and metal guide. (100,200, 400,500,700,1800)
Figure 22:
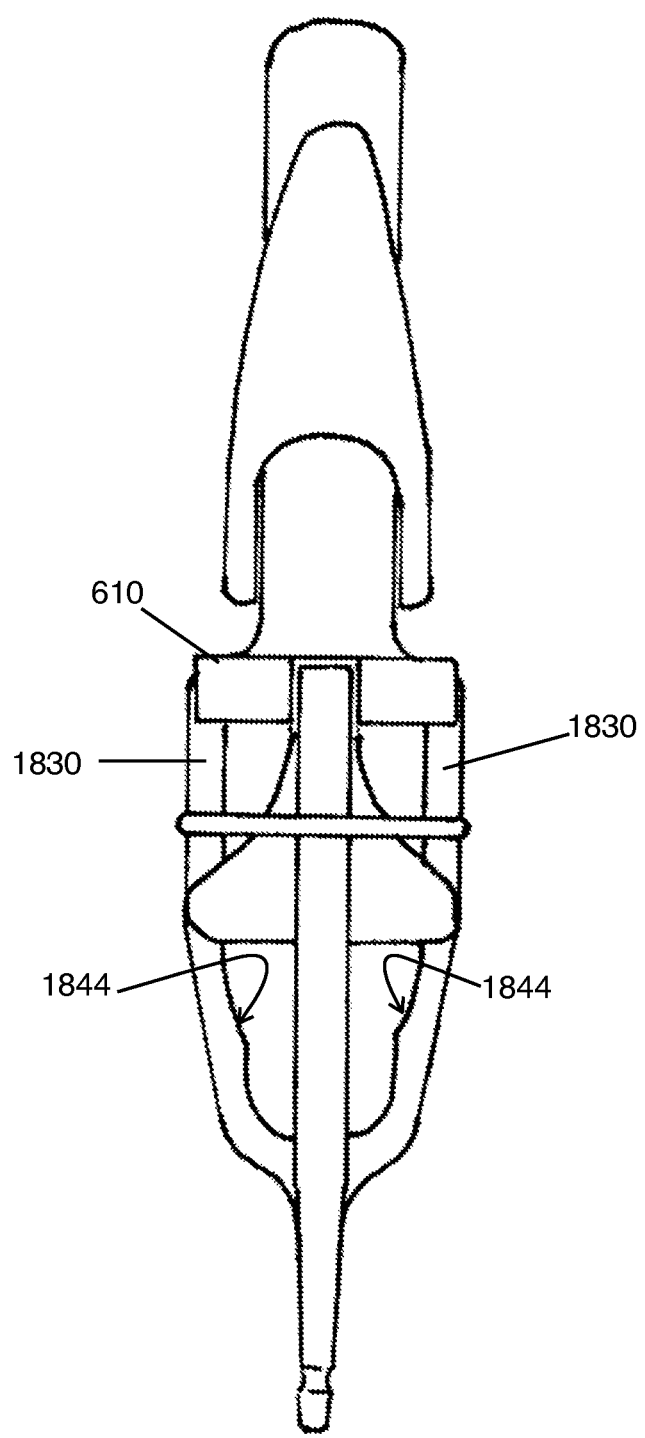
FIG. 22 is a front view of an 'un-actuated' mechanical linkage connected to an inner slider rod within an outer slider tube, with a mid-section mounted first link handle and a second link, with a full complement of slider arms containing an intermediate sleeve and metal guide. (200,300, 400,500,700,1800)

Specifically, the preferred embodiment of the present invention, as shown in at least FIG. 20-FIG. 32, (need to annotate) presents a dilator device (100, FIG. 23) consisting at least of an outer slider tube (500, FIG. 23) having a spreader arm assembly (1800, FIG. 24) attached to an outer slider tube first end (510, FIG. 21); an inner slider rod (300, FIG. 21) concentrically disposed within the outer slider tube (500, FIG. 21), the inner slider rod (300) including at least one keying element (380, PE3) preventing the inner slider rod (300) from rotating within the outer slider tube (500); the outer slider tube (500) including a keying element (550, PE3) (FIGS. P3, P6A, P6B need to annotate, KM1A, KM1B, KM2A, KM2B)) preventing the inner slider rod (300) from rotating within it; and the dilator device (100) further including wherein one end of a first link/inner slider rod handle (340) is pivotally linked to a first end (310, FIG. 21) of the inner slider rod (300) by a second link (350, FIG. 21) with the other end of the first link/inner slider rod handle (340, FIG. 21) being pivotally connected to the outer slider tube first end (510, FIG. 21).

The inner slider rod (300) includes an inner slider rod end face (370, FIG. 21) disposed at a second end (360, add to, FIG. 21) of opposite the first end (310) of the inner slider rod (300).

The inner slider rod (300) at least one keying element (380, PE3) aligns and mates with the keying element (550, PE3) in the outer slider tube (500, PE3) when the inner slider rod (300, PE3) is properly inserted into the outer slider tube (500, PE3).

The inner slider rod second end (360, PE4) includes keying features (384, PE4) which align spreader arm limbs (1830).

An inner slider rod passage way (376, PE6C) is provided within the inner slider rod (300). The inner slider rod passage way (376) extends from the inner slider rod end face (370, PE6B) towards the inner slider rod first end (310, PE6B), wherein the inner slider rod passage way (376) exits the inner slider rod (300) at a location (378, PE6B) (P6B need to cross section) off-set from a center (376). The inner slider rod end face (370) further includes tapered surfaces (374 PE6A) extending into the inner slider rod passage way (376).

While in the preferred embodiment an intermediate sleeve (400, FIG. 23), is threaded from the inner slider rod end face (370) through the inner slider rod passage way (376) and out the inner slider rod passage way exit (378). In alternate embodiments the intermediate sleeve (400) may not be used.

The spreader arm assembly (1800, FIG. 24) includes at least a plurality of spreader arm limbs (1830, FIG. 21) pivotally attached to a slider ring (600) at a slider arm first end (810, FIG. 21), a retaining ring (1201, FIG. 23) is positioned to constrain the plurality of spreader arm limbs (1830) against the inner slider rod second end (360). When applicable, the plurality of spreader arm limbs (1830) also hold intermediate sleeve (400, FIG. 23), through which metal guide (50, FIG. 24) can be threaded.

Figure 23:
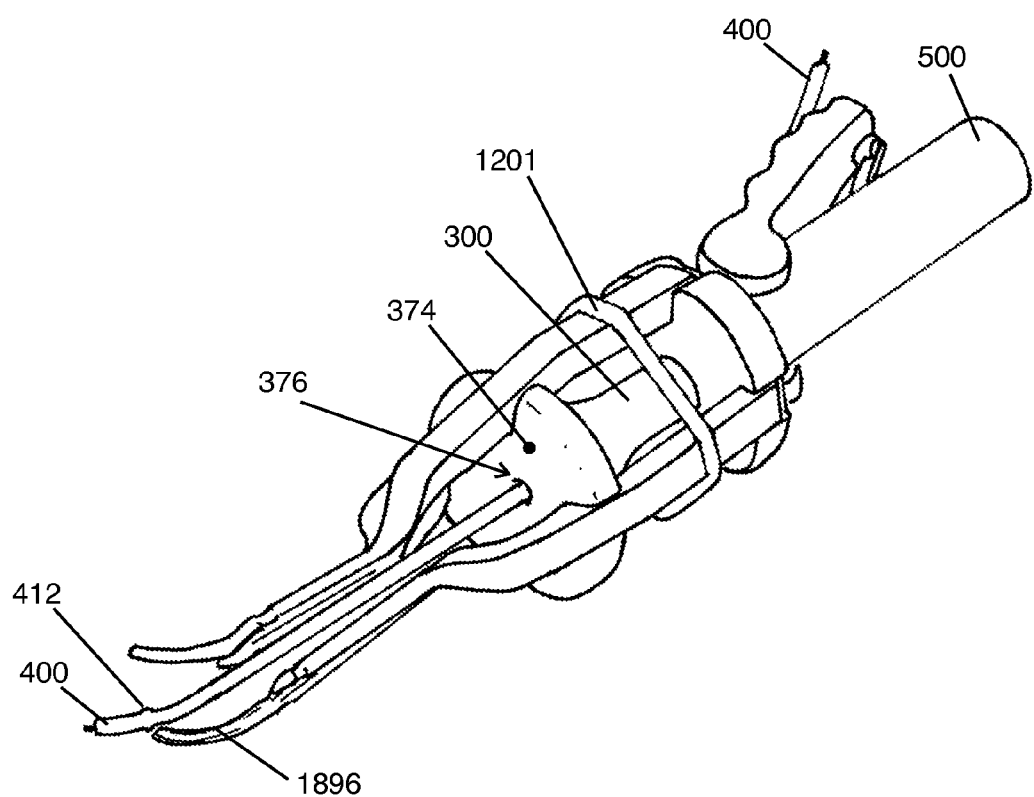
FIG. 23 is a photo of an 'actuated' dilator with linked handle near its mid-section; and with a flexible intermediate sleeve carrying a 'flexible metal guide', passing entirely through it. (100,200,400,700, 1201)
Figure 24:
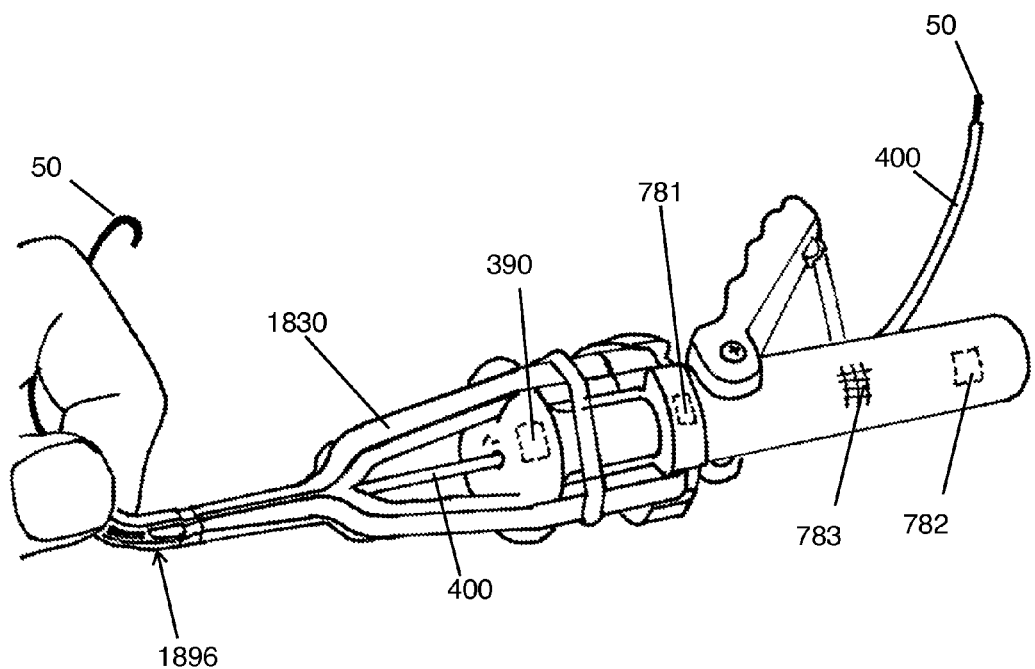
FIG. 24 is a photo of an un-actuated dilator with linked handle near its mid-section, with an intermediate sleeve containing a 'metal guide' passing entirely through it. (400, 500,1800)
Figure 25A:
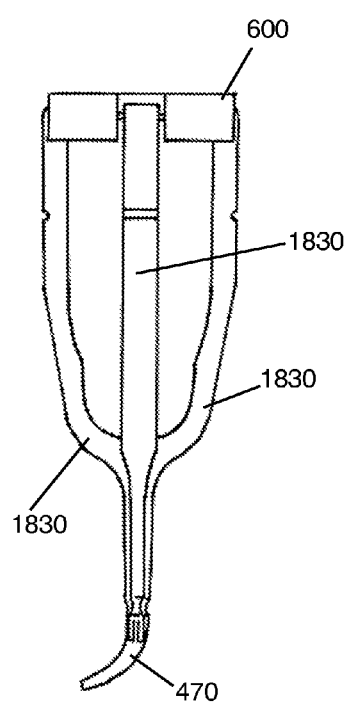
FIG. 25A is a side view of a spreader arm assembly, with straight slider arm tips, carrying a curved tip intermediate sleeve, which is keyed to the slider arms tips. (400,600,800)
Figure 25B:
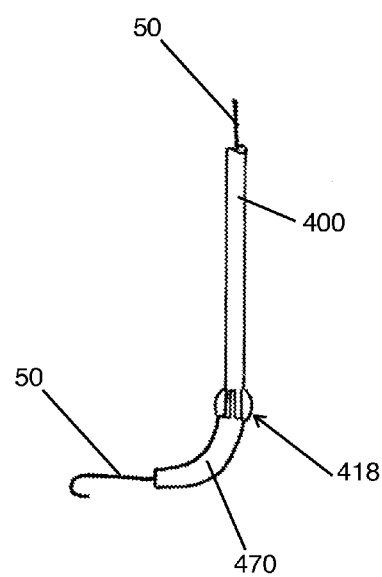
FIG. 25B is a side view of an intermediate sleeve with curved tip with keys to interface with slider arm tip keys. (400)
Figure 25C:
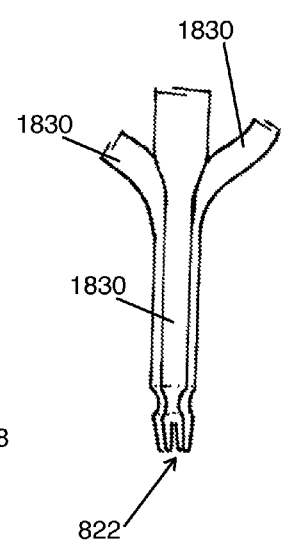
FIG. 25C is a side view of straight slider arm tips, which are keyed to interface with an intermediate sleeve. (800)
Figures 26A, 26B:
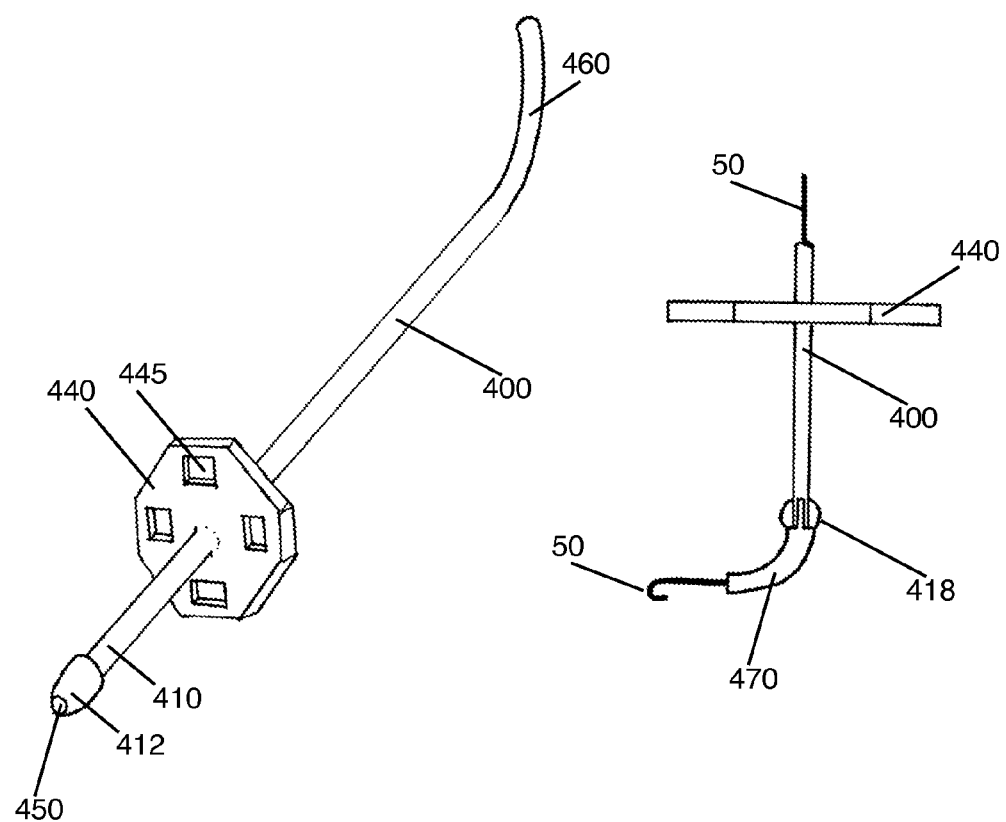
FIG. 26A is an isometric view of an intermediate sleeve for the metal guide, with integral retainer ring element and a straight tip. (400)
FIG. 26B is a side view of an intermediate sleeve for the metal guide, with integral retainer ring element and a curved tip. (400)
Figure 27:
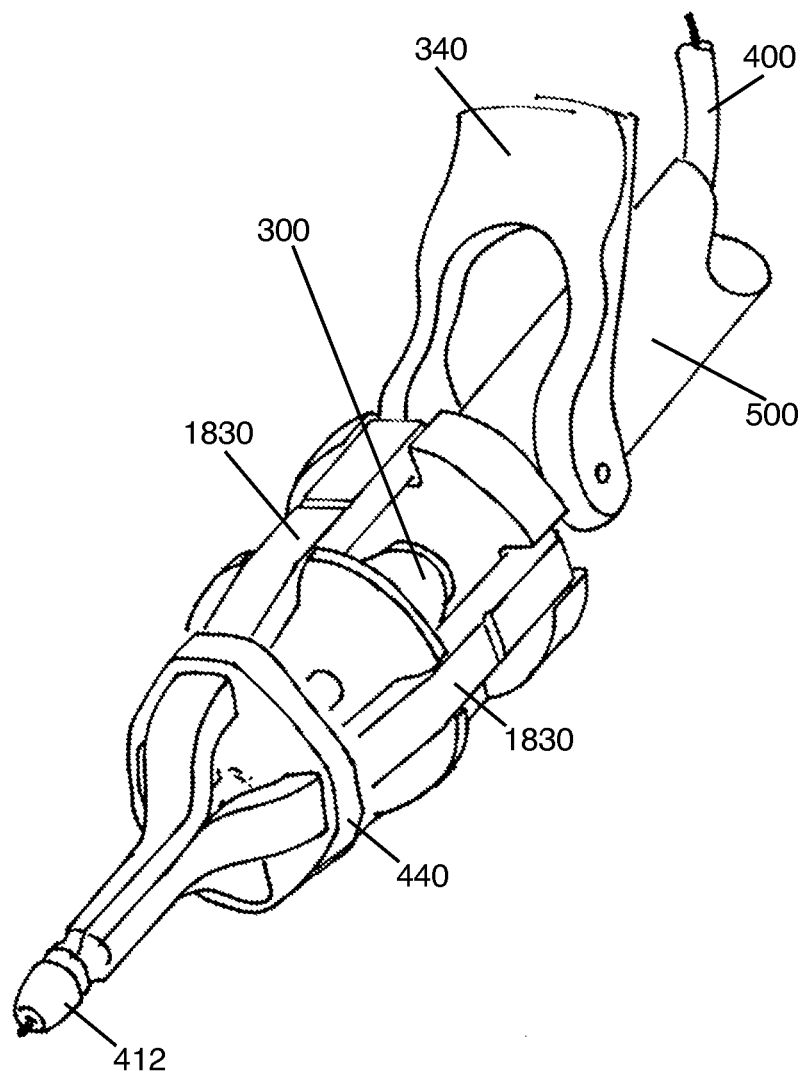
FIG. 27 is an isometric view, showing two pairs of slider arms inserted into the intermediate sleeve with integral retainer ring element which is carrying a 'flexible metal guide', where the sleeve with 'metal guide' passes freely through the passage in the inner slider rod. (300, 400, 500, 1800)
Figure 28:
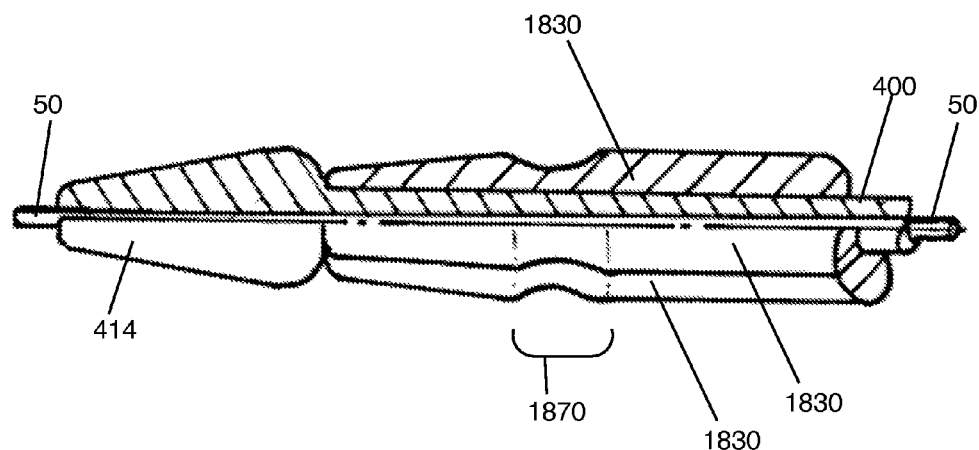
FIG. 28 is side view/partial section, showing a pair of slider arms holding a 'metal guide' in an intermediate sleeve, where the sleeve has an 'over-travel bulb' feature prior to the arms, near the circumferential tactile detent feature. (400, 1830)
Figure 29:
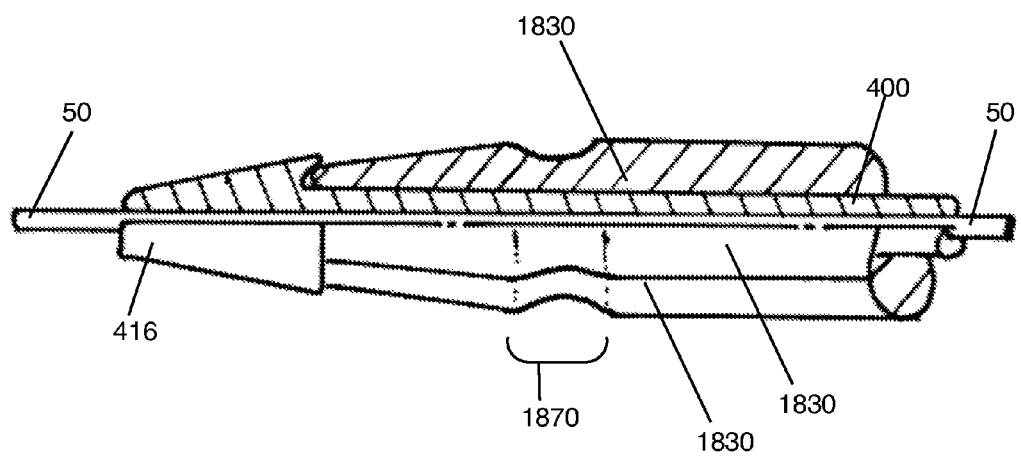
FIG. 29 is side view/partial section, showing a spreader arm assembly holding a 'metal guide' in an intermediate sleeve, where the sleeve has an 'shroud' feature overlapping with the spreader arms, near the circumferential tactile detent feature. (400, 1830)
Figure 30A:
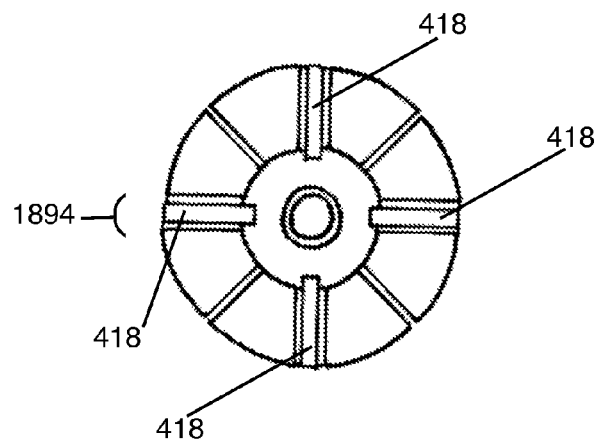
FIG. 30A is an end view, showing spreader arm limbs holding an intermediate sleeve which is carrying a 'flexible metal guide', where the intermediate sleeve with 'metal guide' passes into the passage in the inner slider rod. The spreader arm limbs and the intermediate sleeve have 'interlocking/over lapping' features. (418, 1894)
Figure 30B:
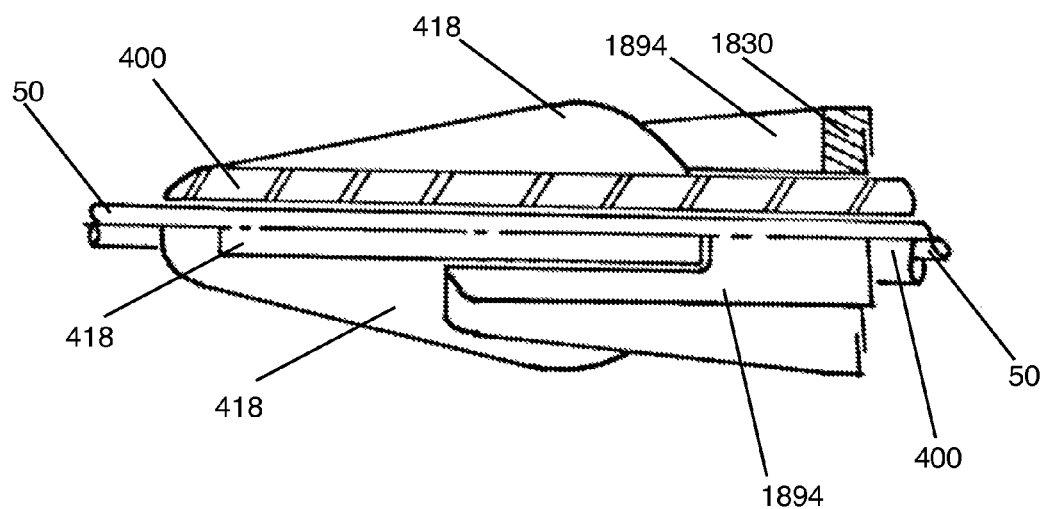
FIG. 30B is a partial section side view, showing spreader arm limbs holding an intermediate sleeve which is carrying a 'flexible metal guide', where the intermediate sleeve with 'metal guide' passes freely into the passage in the inner slider rod. The spreader arm limbs and the intermediate sleeve have 'interlocking/over lapping' features. (418, 1894)
Figure 30C:
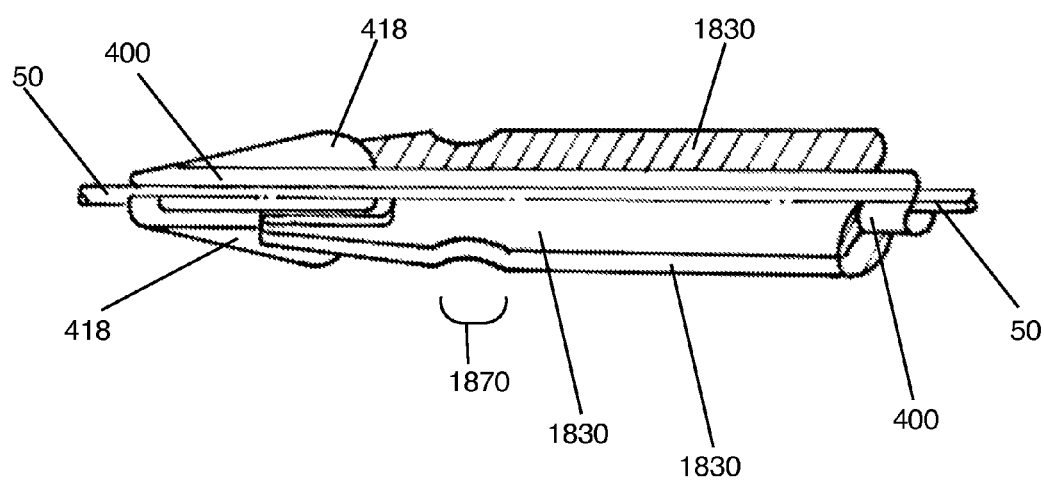
FIG. 30C is a partial cross section view, showing spreader arm limbs holding an intermediate sleeve which is carrying a 'flexible metal guide', where the intermediate sleeve with 'metal guide' passes freely into the passage in the inner slider rod. The spreader arm limbs and the sleeve have 'interlocking/over lapping' features. (400, 1830)
Figure 31:
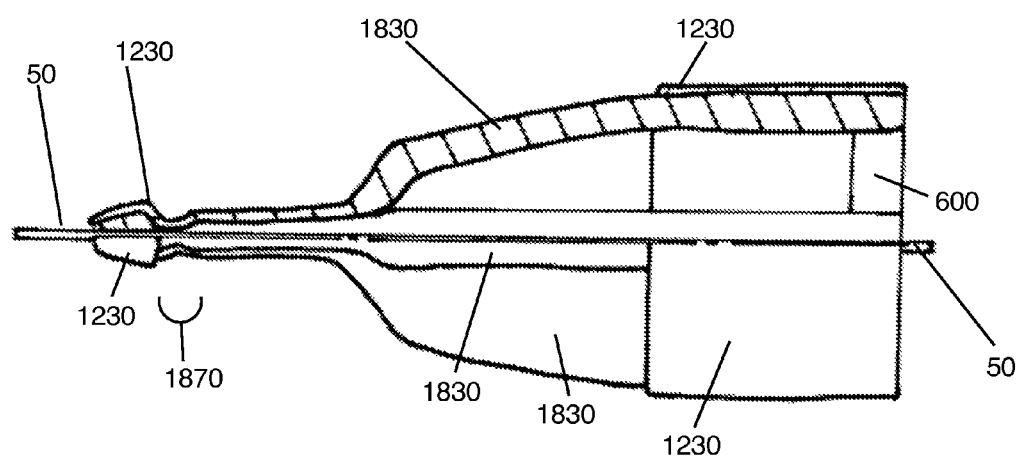
FIG. 31 is a partial section side view, showing slider arm limbs of a spreader arm assembly; 'over-molded' with an elastomeric sleeve ahead of the circumferential tactile detent feature, carrying a 'flexible metal guide'. (50, 1830)
Figure 32:
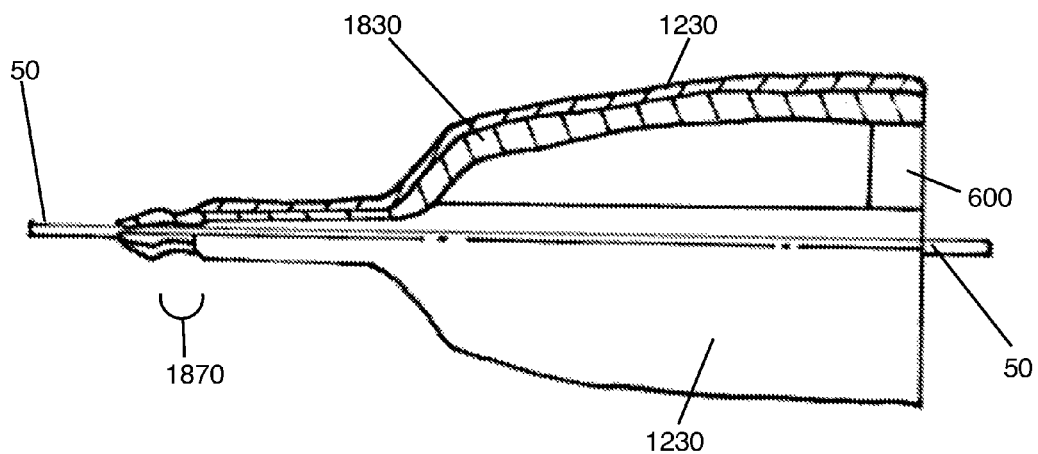
FIG. 32 is a partial section side view, showing slider arm limbs of a spreader arm assembly; 'over-molded' with an elastomeric sleeve after the circumferential tactile detent feature, carrying a 'flexible metal guide'. (50,1830)
Figure 33:
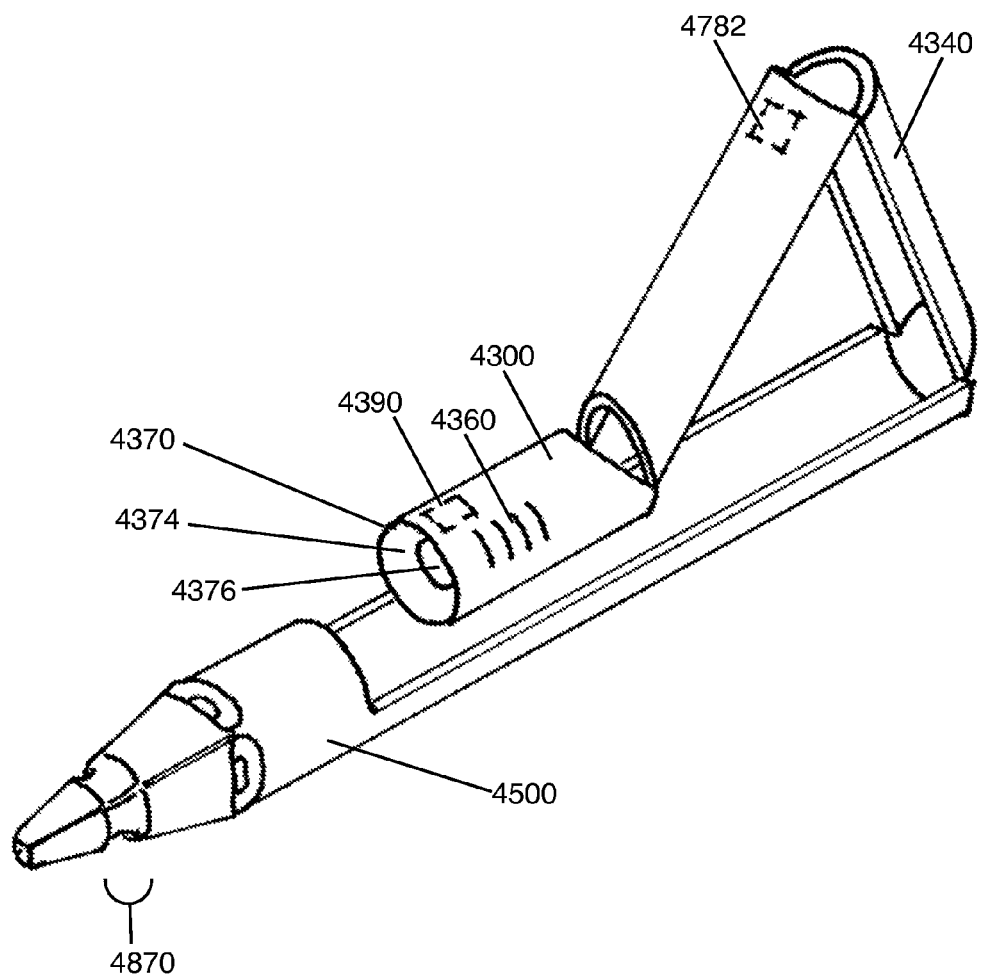
FIG. 33 is an isometric side view of major elements for a dilator constructed from a single piece, flexible housing, with an end mounted handle. (100, 4300,4500,4800)
Figure 35A:
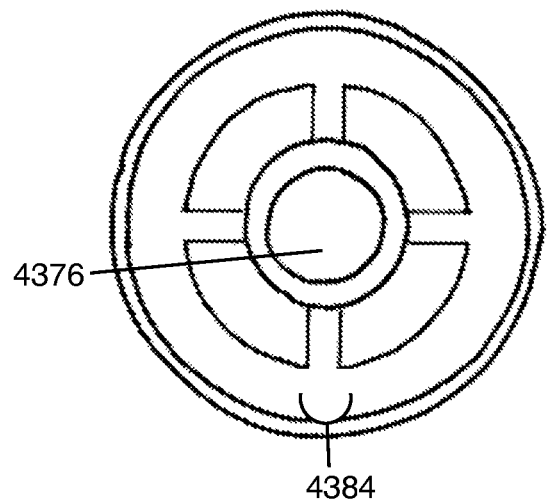
FIG. 35A is an end view of an inner slider rod segment with keying features for spreader arm limbs and an outer slider tube segment. (4300)
Figure 35B:
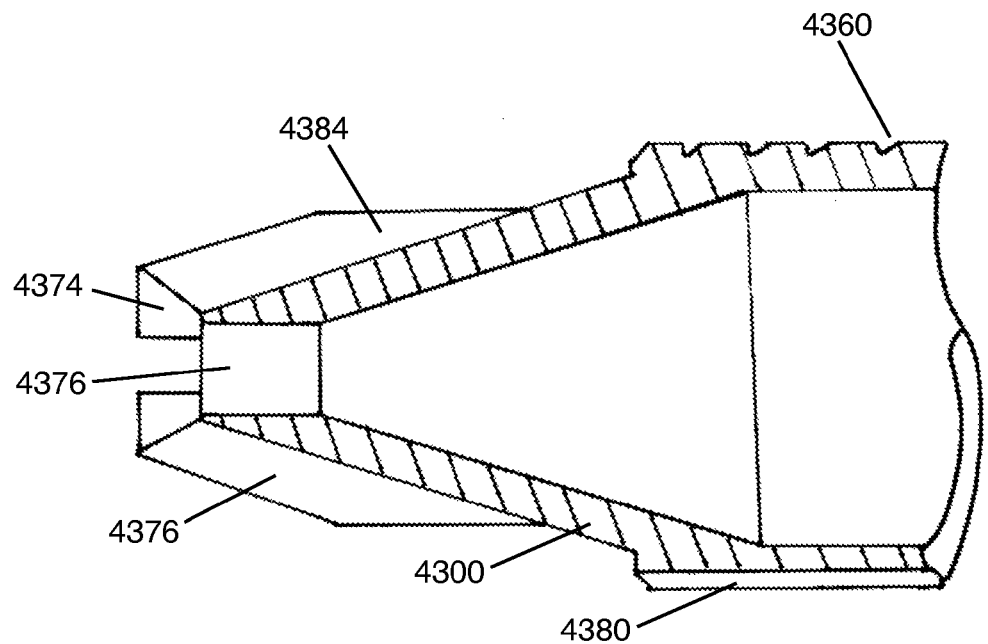
FIG. 35B is a section view of an inner slider rod segment with keying features for spreader arm limbs and an outer slider tube segment. (4300)
Figure 36A:
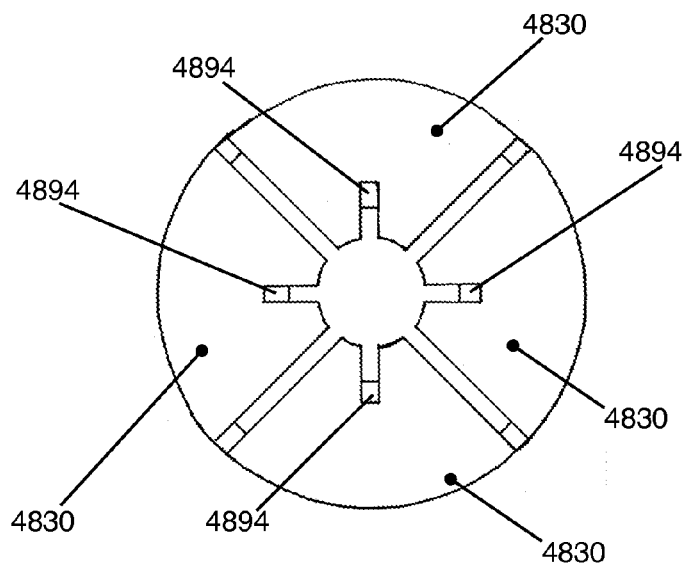
FIG. 36A is an end view of a spreader arm assembly segment showing keying features for an intermediate sleeve. (4800)
Figure 36B:
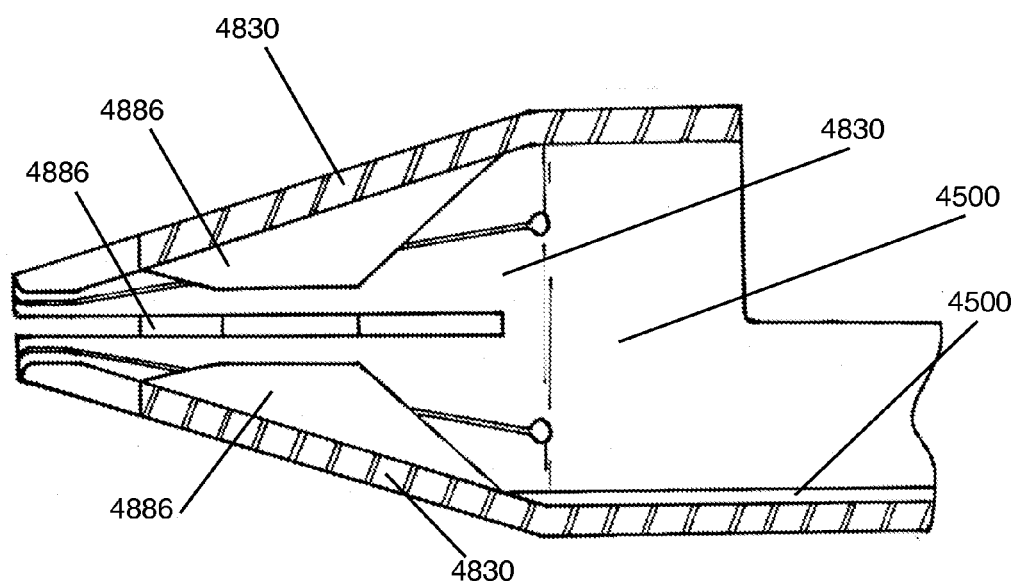
FIG. 36B is a section view of a spreader arm assembly segment with keying features for an inner slider rod segment. (4800)
Figure 37:
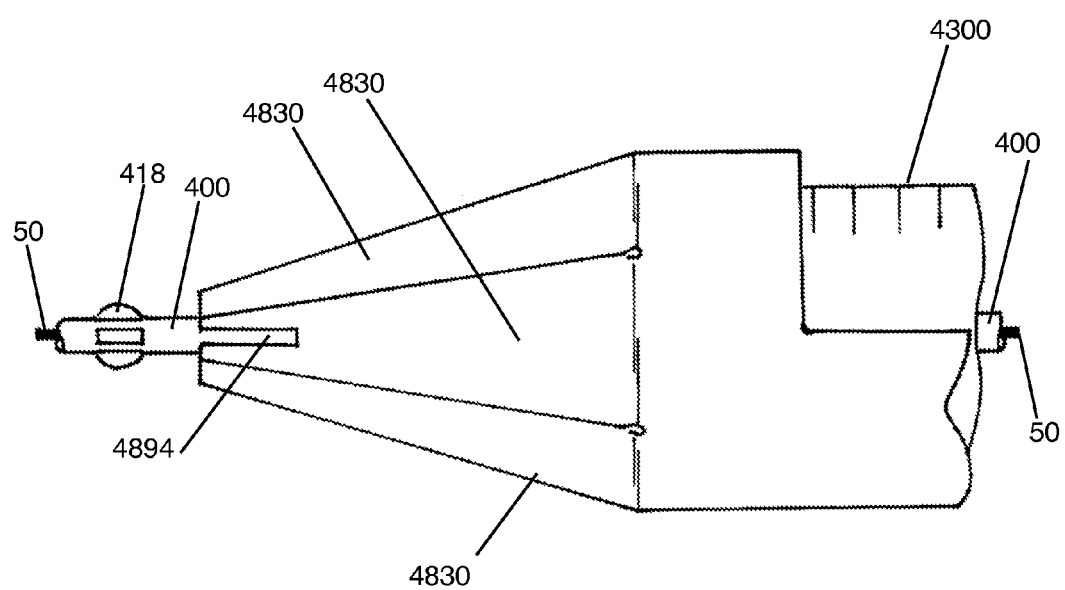
FIG. 37 is a side view of inner slider rod segment, assembled to outer slider tube segment and integral spreader arm segment, with intermediate sleeve inserted. (4300,4500, 4800)

As shown in FIGS. 20, 21 and 23, in the preferred embodiment of the present invention generally, the actuation means (200) are provided by an actuator mechanism which is comprised of at least the first link lever handle (340, FIG. 21) which is pivotally attached (511—handle mount position) to the outer slider tube first end (510, FIG. 21) (positioned near the dilator's middle section). Movement of the first link lever handle (340) drives a second (intermediate) link (350, FIG. 21) that is pivotally attached between the lever handle (340) and the inner slider rod first end (310).

The actuation means (200) provides a mechanical advantage to the operator of the dilator where movement of the lever handle (340) imparts force to the inner slider rod (300).

An outer surface (342, FIG. 21) of the first link handle (340) and an outer surface (560, add to FIG. 21) of the outer slider tube (500) (which contact the operator's hand), are textured to provide gripping means.

In the preferred embodiment, the location of the handle near the middle of the dilator (100) at the handle mount position (511, FIG. 21), which is positioned near the outer slider tube first end (510), affords substantial ergonomic advantages to the operator in terms of gripping, guiding, manipulating and actuating the dilator device with a single hand. Further positioning lever handle (340) at the handle mount position (511) presents optimum mechanical advantage to the operator of the dilator during single hand usage.

The spreader means (700) of the preferred embodiment constitutes a spreader arm assembly generally comprised of a plurality of spreader arm limbs (1830) which are pivotally attached (1820) to slider ring pins (610) mounted in a slider ring (600). This spreader arm assembly is attached to the first end (510) of the outer slider tube (500).

As is shown in (FIGS. P7A, P7B P7C SM5A, SM5B and SM5C need to annotate,) the spreader arm limbs (1830) are driven outward by the translation of the inner slider rod (300) through the outer slider tube (500) as it presses against inner surfaces (1842, 1844) of the spreader arm limbs (1830). The spreader arm limbs (1830) are elastically retained against the inner slider rod (300) by retaining ring (1201) positioned with a ring seat (1865) provided on at least one of the spreader arm limbs (1830), see FIG. 25A.

The retaining means of the preferred embodiment is generally comprised of circumferential tactile detent depression features (1870 see FIGS. 20, 22, 25A, 25B, P1, P2, P5, P7A-C, P8A and P8C need to annotate) which are aligned in parallel across the plurality of adjacent spreader arm limbs (1830). The incorporation of a keyed or curved tipped (430—see FIGS. 25A, P8A and P8C need to annotate), intermediate sleeve (400) can further enhance the retention of the dilator within the workpiece orifice during use.

The slider rod to slider tube keying means of the preferred embodiment of the present invention are comprised of a keyway (550 shown in Figure) within the outer slider tube (500). The keyway (550) relates to a key (380 shown in FIG. P3) on the outer surface of the inner slider rod (300).

The slider tube to spreader arm keying means of the preferred embodiment of the present invention include wherein the outer slider tube (500) has a keying feature (514 shown in FIGS. P1 and P5 need) complimentary to a mating keying feature (606 shown in FIGS. P1 and P5) on the slider ring (600) of the spreader arm assembly.

The slider rod to spreader arm keying means of the preferred embodiment of the present invention include wherein the inner slider rod (300) shown (in FIG. 9), has peripheral external keyways (384) to engage the sides of the spreader arm limbs (1830).

The spreader arm to intermediate sleeve keying means of the preferred embodiment of the present invention include wherein the straight spreader arm limb tips (1890—see FIGS. P8A-P8C need to annotate 25B) in this preferred embodiment of the present invention, are keyed (1894—see FIGS. P8A-P8C need to annotate 30A, 30B, KMnn's) to corresponding bridging tabs (418—see FIGS. P8A-P8C need to annotate 30B, 30C, KMnn's) near the first end (410) of the intermediate sleeve (400).

Figure 14A:
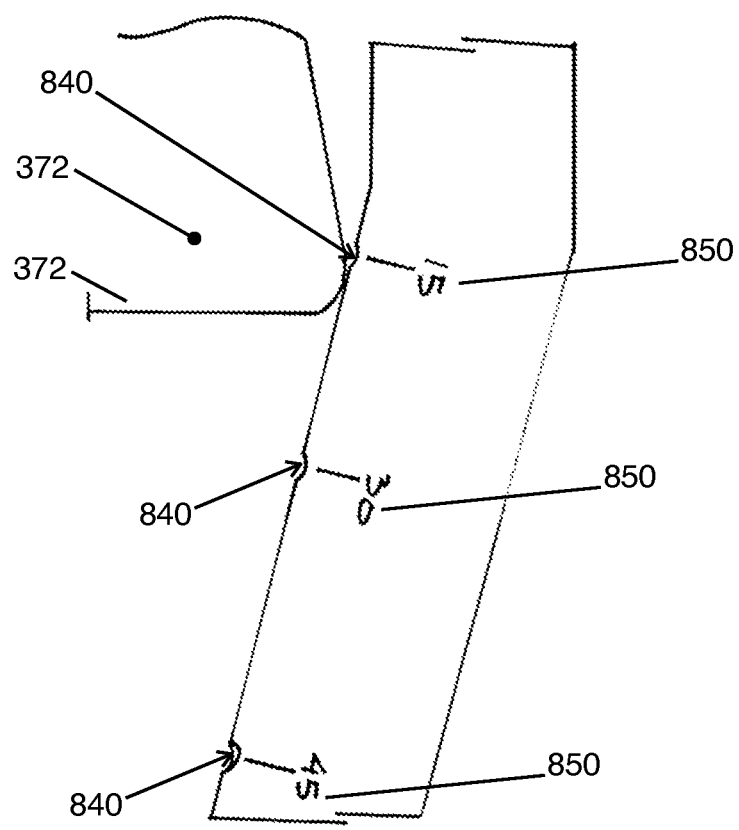
FIG. 14A is a side view of a slider arm and contacting inner slider rod, showing tactile detent contact surfaces and visual markings at their interface. (300, 800)
Figure 14B:
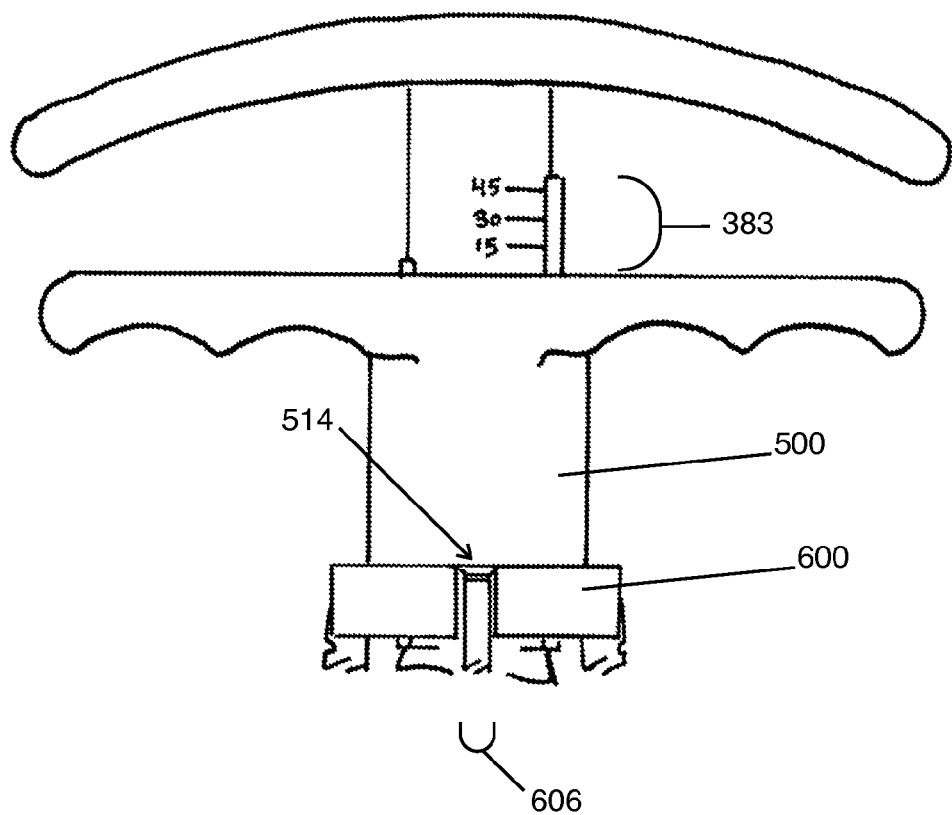
FIG. 14B is a side view of an inner slider rod, showing markings on surfaces proximate to the outer slider tube at their interface, for visual feedback. (300, 800)
Figure 15A:
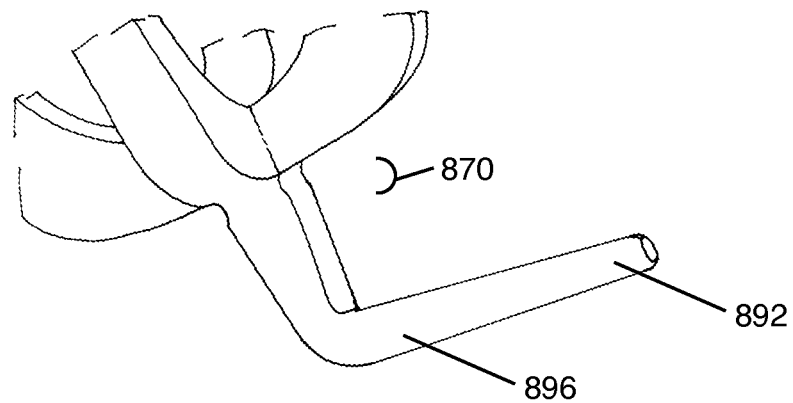
FIG. 15A is an isometric view showing an 'un-actuated' slider arm group. (800)
Figure 15B:
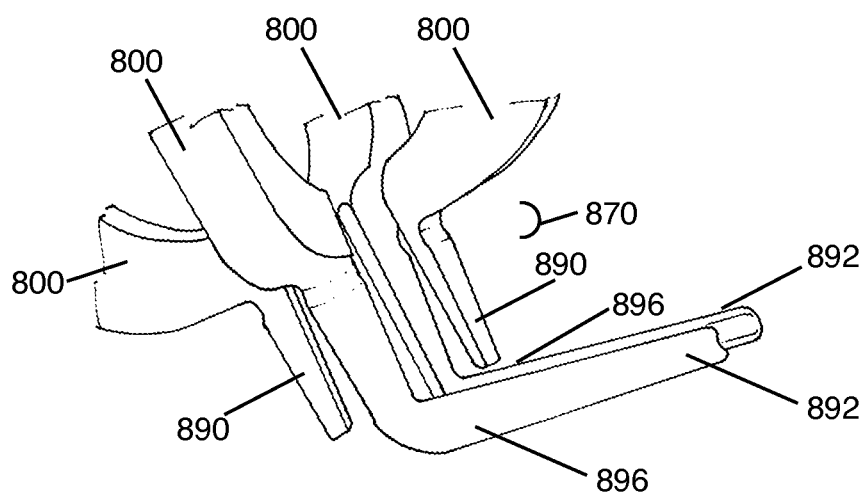
FIG. 15B is an isometric view showing an 'actuated' slider arm group. (800)
Figure 15C:
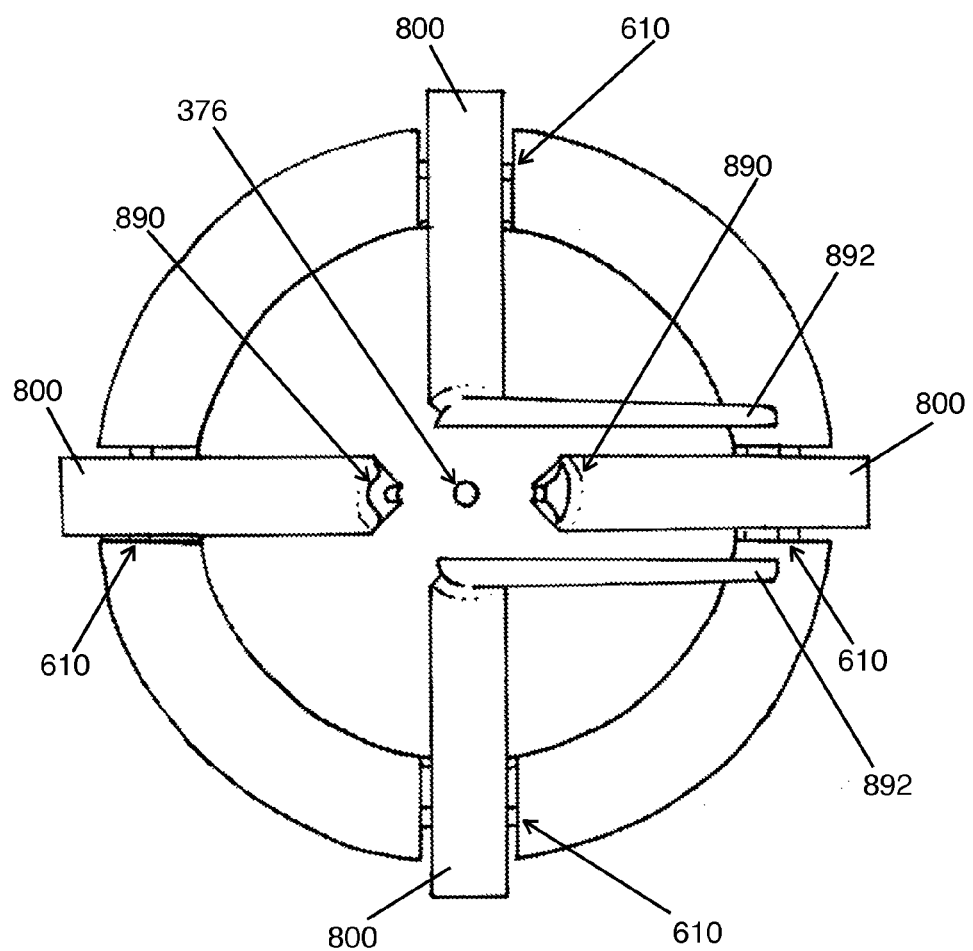
FIG. 15C is an end view showing two pairs of 'actuated' slider arms traveling equidistantly to create a round orifice of maximum predetermined diameter. (800)
Figure 16:
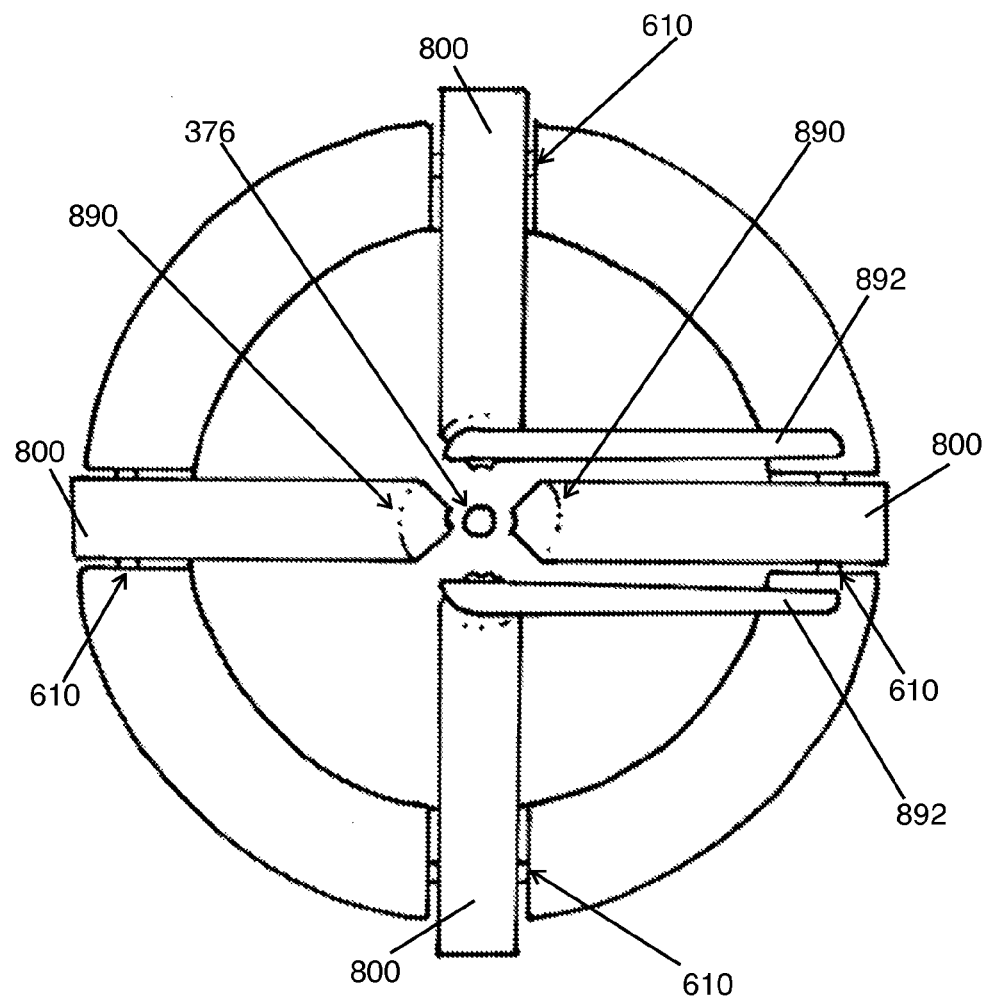
FIG. 16 is an end view showing two pairs of 'actuated' slider arms traveling non-equidistantly to create an elliptical orifice of maximum predetermined diameters, comparable to FIG. 17 (300, 600, 800)
Figure 17:
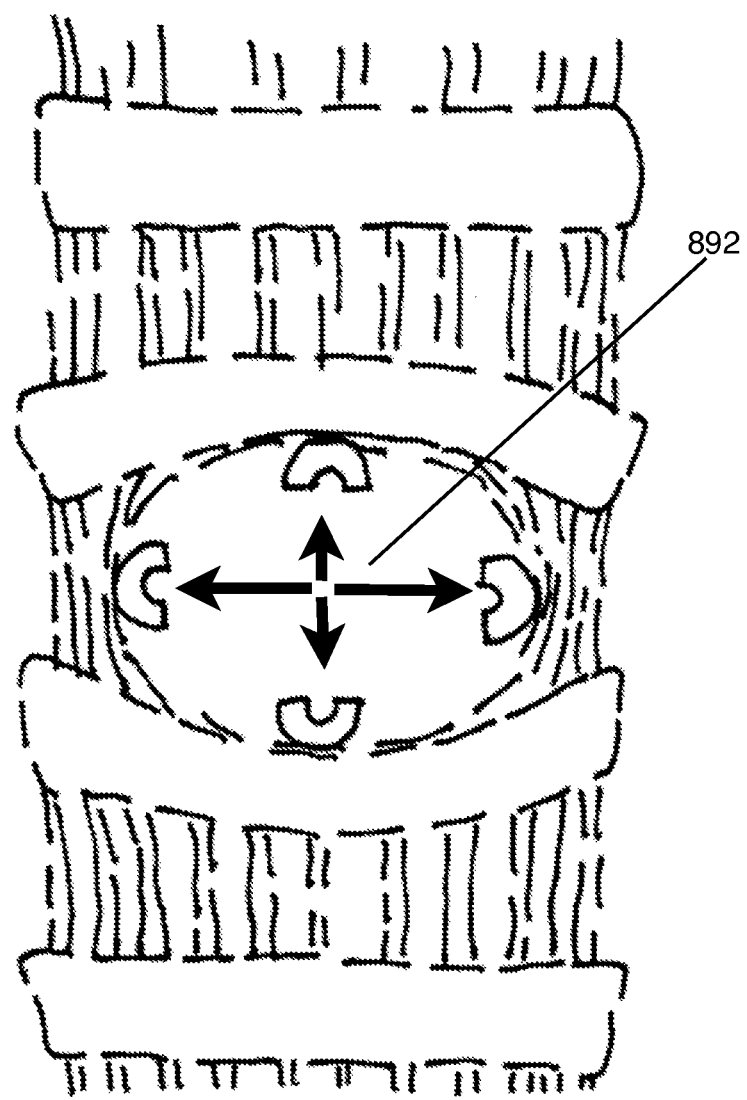
FIG. 17 is a diagram of an elliptical opening created in tissue between cartilages. (ref FIG. 1)
Figure 18A:
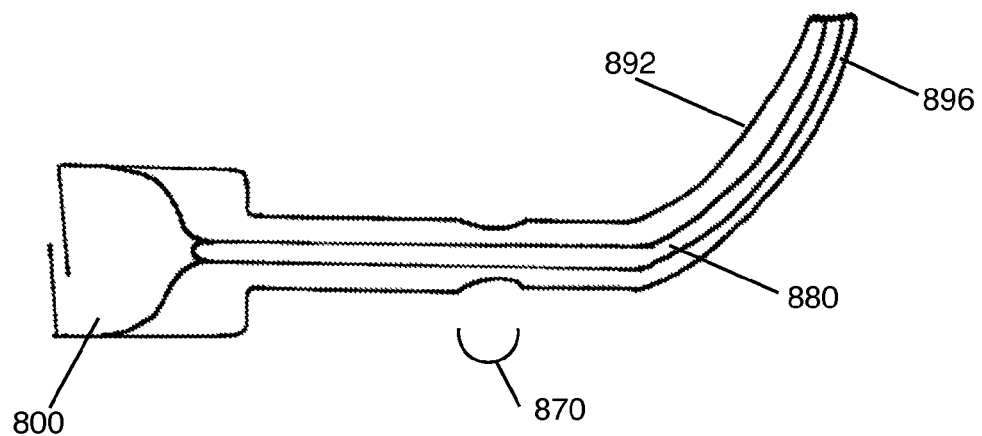
FIG. 18A is an inside view of a slider arm curved tip with a circumferential dilation detent segment, and relief for intermediate sleeve or flexible guide. (800)
Figure 18B:
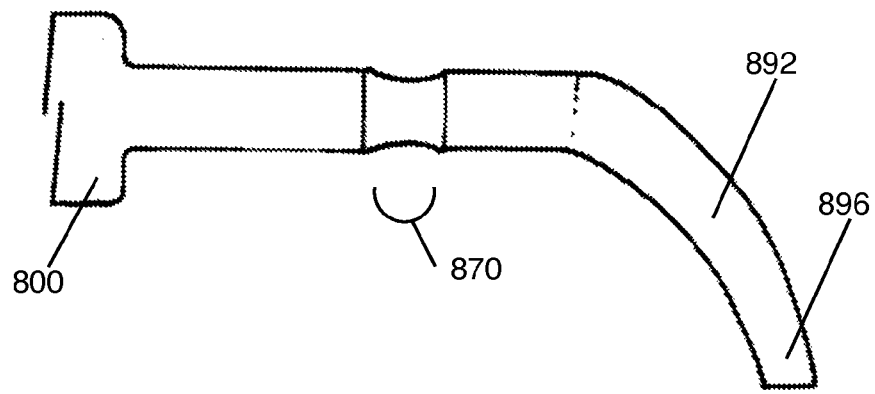
FIG. 18B is an outside view of a slider arm curved tip with a circumferential dilation detent segment. (800)

As is shown in FIGS. FM1A and P7D, the feedback means of the preferred embodiment of the present invention are generally comprised of the tactile interaction of notches (840—FIGS. 14A and FM1) on the inside surface (1840) of at least one spreader arm limb (1830) and the second end of the inner slider rod (372) where it engages the notches (840) of the spreader arm limb (1830).

The feedback means of the preferred embodiment of the present invention further includes visual feedback provided by markings (1850—FIGS. FM1B and P7E) on the side of at least one spreader arm limb (1830) to indicate the proximity of the second end of the inner slider rod (360).

Additional feedback means of the present invention are provided by colored tips (1896—see FIGS. 20 P1, P5, P7A-C, P8A,B, P9 and P10, FMnn's) on the spreader arm limbs (1830). Portions of the spreader arm limb colored tips (1896) which are outside of the workpiece (such as the trachea) are visible and provide an indication of the depth of the insertion of the dilator into the orifice of the workpiece. Further, the spreader arm limb colored tips (1896) may be made of a material which when illuminated with a broncheoscope or light source enhances visibility of the position of the dilator with respect to the orifice of the workpiece.

The communication means of the preferred embodiment are generally comprised of Radio Frequency Identification Devices (such as RFID chips) mounted in at least one actuator means component, such as the outer slider tube, (782, FIGS. 24, PE2, CM01) and in at least one spreader means component such as the slider ring. (781, FIGS. 24, PE2, CM01)

Degradable material such as PVA or PLA polymer which deteriorates after exposure to various cleaning regimens, substances, or conditions, when used as part of the dilators components (such as the actuator means (200), spreader arm assembly (1800), or intermediate sleeve (400)) also constitute communication means in that the condition of the degradable material communicates status information of the dilator. For example a dilator with pristine components would communicate that the dilator is most likely new and unused, whereas a dilator in a less than pristine condition would communicate that the dilator has been used or improperly stored. Further, the state of the condition of the material of the dilator components can communicate important information such as the time period over which the dilator has been used or the time period over which the dilator has been exposed to degrading substances or conditions.

Markings (783 FIGS. 24, CM01), including barcodes, glyphs, serial numbers and other identification or indicia recognizable by the user and by enterprise resource management systems also constitute communication means.

The illumination means of the preferred embodiment is generally comprised of a source of light (390 FIGS. 24, IM01) provided on or within the inner slider rod (300). The illumination means projects or diffuses light onto the spreader arm limb tips (1890 FIGS. 24, IM01) and stoma or hole in the workpiece or trachea. The illumination means interacts with the material of the intermediate sleeve (400), the actuation means (200), the gripping means, the spreader means (700), the retaining means, all keying means, the feedback means, the communications means, the inner slider rod (300), and the outer slider tube (500), as selected, enabling these components to function as a light pipe.

Alternate Embodiment 1

A first alternate embodiment of the present invention includes actuation means (200), spreader means (700), retaining means (870), keying means, feedback means, gripping means, illumination means, and communication means.

Specifically, the first alternate embodiment of the present invention, as shown in at least FIG. 2, FIG. 3, FIG. 4, FIG. 5, FIG. 6, FIG. 7, FIGS. 8A and 8B, FIG. 9, FIGS. 10A, 10B and 10C, FIG. 11, FIG. 12, FIGS. 13A, 13B and 13C, FIGS. 14A and 14B, FIGS. 15A, 15B and 15C, FIG. 16, and FIGS. 18A and 18B; presents a dilator device (100) consisting at least of an outer slider tube (500) with a slider ring (600) attached to it at an outer slider tube first end (510), an inner slider rod (300) concentrically disposed within the outer slider tube (500), the inner slider rod (300) including a keying element (380) preventing the inner slider rod (300) from rotating within the outer slider tube (500); the outer slider tube (500) including a keying element (550) preventing the inner slider rod (300) from rotating within it. A handle (320) is disposed at a first end (310) of the inner slider rod (300). This handle (320) pushes the inner slider rod through the outer slider tube (500). An inner slider rod end face (370) is disposed at a second end (360) of the inner slider rod (300) opposite the first end (310) of the inner slider rod (300). The inner slider rod (300) includes at least one keying feature (380) which aligns it to a mating keying feature (550) in the outer slider tube (500). The inner slider rod second end (360) includes keying features (384) which align slider arms (800). An inner slider rod passage way (376) is provided within the inner slider rod (300). The inner slider rod passage way (376) extends from the inner slider rod end face (370) towards the inner slider rod first end (310), wherein the inner slider rod passage way (376) exits the inner slider rod (300) at a location (378) off-set from a center (376). The inner slider rod end face (370) further includes tapered surfaces (374) extending into the inner slider rod passage way (376), wherein a metal guide (50), is threadable from the inner slider rod end face (370) through the inner slider rod passage way (376) and out the inner slider rod passage way exit (378). A plurality of removable slider arms (800) are pivotally attached to the slider ring (600) at a slider arm first end (810), a retaining ring (1201) is positioned to constrain the plurality of slider arms (800) against the inner slider rod second end (360). The plurality of removable slider arms (800) can hold a metal guide (50) which can be threaded through them and subsequently into and through the inner slider rod passage way (376), when the dilator (100) is not actuated.

In this alternate embodiment of the present invention shown in FIG. 2 the actuation means (200) are provided by an actuator mechanism comprised of a handle (320) mounted directly to an inner slider rod (300), where it pushes the inner slider rod (300) through an outer slider tube (500). This handle arrangement provides certain mechanical advantage to the operator. The surfaces of the handle (322) and a handle element (532) on the outer slider tube (500), which contact the operator's hand, are heavily textured, providing gripping means. The location of the handle element pair affords substantial ergonomic advantages to the operator in terms of gripping, guiding and manipulating the device with a single hand.

Figure 13A:
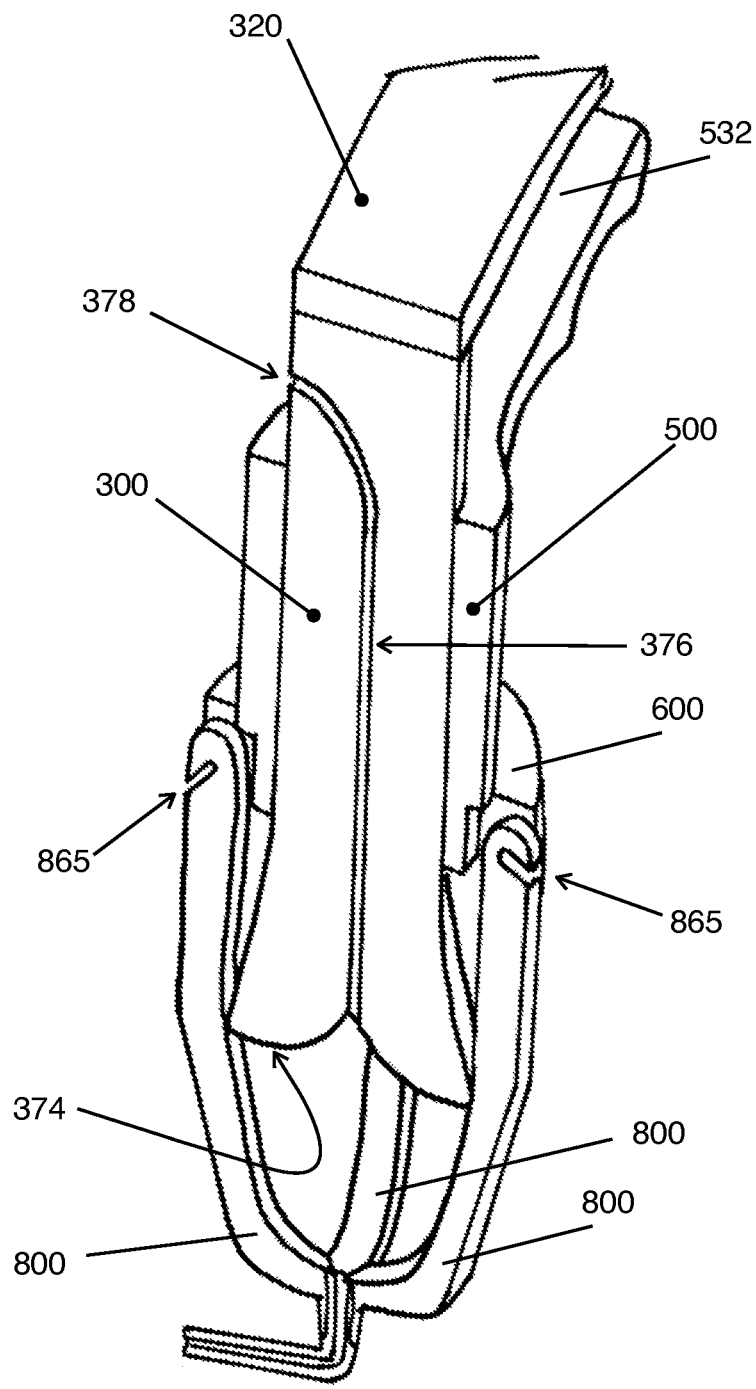
FIG. 13A is a section view of a dilator assembly showing an inner slider rod contacting the inside surfaces of slider arms at the beginning stage of actuation. (300, 500, 600, 800)
Figure 13B:
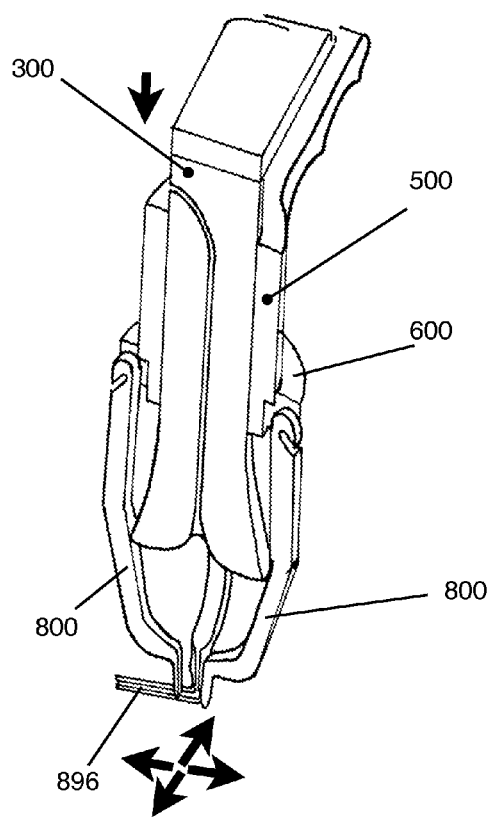
FIG. 13B is a section view of a dilator assembly showing an inner slider rod contacting the inside surfaces of slider arms in the midst of actuation. (300, 500, 600, 800)
Figure 13C:
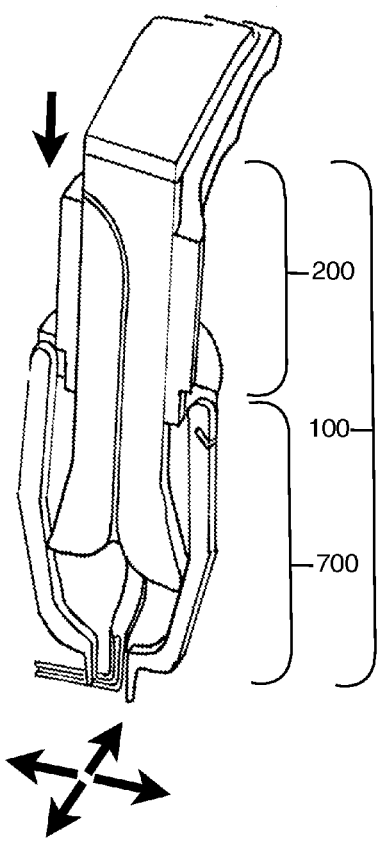
FIG. 13C is a section view of a dilator assembly showing an inner slider rod contacting the inside surfaces of slider arms at the limit of actuation. (100, 200, 700)

The spreader means (700) of this alternate embodiment of the present invention are generally comprised of slider arms (800) which are pivotally attached (820) to slider ring pins (610) mounted in a slider ring (600), which is attached to the first end (510) of the outer slider tube (500). As is shown in FIGS. 13A, 13B and 13C these slider arms (800) are driven outward by the translation of the inner slider rod (300) through the outer slider tube (500) against their inner surfaces (842,844). The slider arms (800) are retained against the inner slider rod (300) by a retaining ring (1201).

The retaining means of this alternate embodiment of the present invention are comprised of the circumferential tactile detent depression features (870) which continue from surface to surface of adjacent slider arms (800). The additional incorporation of at least one pair of slider arms (800) with curved tips (892, see FIGS. 5 and 6 need to annotate) can further enhance the retention of the dilator during use. Alternately (see FIGS. SM8A, SM8B and SM8C), the addition of straight tipped (890) slider arms (800) keyed (894) with a curved tipped (430) intermediate sleeve (400) can also further enhance retention of the dilator during use.

The keying means for this alternate embodiment of the present invention (see FIGS. 3, 4, KM9B and KM9D) is for the inner slider rod (300) to engage a slider arm (800), where the inner slider rod (300) has a raised key (386) which engages inside a recess in a contacting surface (895) of the slider arm (800). An extension of keying construction for this first alternate embodiment of the present invention (see FIGS. KM8A, KM8B and KM8C), would include keying features (894) on slider arm tips (890,892) which are keyed to corresponding bridging tabs (418) near the first end (410) of an intermediate sleeve (400). An alternative keying means for this first alternate embodiment of the present invention would be comprised of a keyway (550) inside the outer slider tube (500) which relates to a key (380) on the outer surface of the inner slider rod (300); the outer slider tube (500) is keyed (514) to the mounted slider arm ring (600) at (606); the slider ring is keyed to the slider arms (800) through pinned pivoting end mounting positions (810). In a further alternative keying means for this first alternate embodiment, shown in FIGS. 5, 6, KM9A and KM9C, the inner slider rod (300) has peripheral keyways (384) to engage lateral surfaces of the slider arms (800).

The feedback means of this alternate embodiment of the present invention (see FIGS. 14A and FM1A), are generally comprised of the tactile interaction of the second end (360) of the inner slider rod (300), where it engages notches on the inside surface (840) of at least one slider arm (800); as well as visual feedback provided by the proximity of the inner slider rod second end (360) and markings (850) on the side of at least one slider arm (800).

Additional feedback means of this alternate embodiment of the present invention (see FIGS. 8A, 8B, AE1_8, AE1_9 FM2A and FM2B), is tactile feedback created within the actuator means by a surface on a spring element (520) in the outer slider tube (500) which engages a mating feature (382) on the surface of the inner slider rod. Translation of the inner slider rod with respect to the outer slider tube creates tactile feedback to the operator as the feature on the inner slider rod (382) engages with the mating surface element (520) of the outer slider tube.

Further additional feedback means of this alternate embodiment of the present invention (see FIGS. 14A and FM1B), are display markings (383) on the inner slider rod (300) to that inform the user through their relative position to a feature or edge near an end of the outer slider tube (500), or near a feature or edge of the slider ring (600) mounted to the outer slider tube (500).

Furthermore, additional feedback means are provided in this alternate embodiment of the present invention by colored tips (896) on the slider arms (800), which are visible from inside the trachea when illuminated with a broncheoscope.

The gripping means of this alternate embodiment of the present invention (see FIGS. 2 and 4), generally comprise heavily textured surfaces (322) on the outer surfaces of the handle (320), and at least an opposing surface (533) on the handle element (532) of the outer slider tube (500).

The illumination means of this alternate embodiment of the present invention (see FIGS. 2 and IM02), is generally comprised of a point source of light (390) contained in the inner slider rod (300), which projects onto the slider arm tips and stoma in the trachea. An extension of illumination means for this first alternate embodiment of the present invention, would include the use of an intermediate sleeve (400) made from the material enabling it to function as a light pipe.

The communication means of this alternate embodiment of the present invention (see FIGS. 2 and CM02), are generally comprised of RFID chips (782) in an actuator element and (781) in at least one slider arm element. Degradable material such as PVA or PLA polymer which deteriorates after exposure to various cleaning regimens, used for the actuator means (200), or slider arms (800), also constitute communication means. Markings (783), including barcodes, glyphs, serial numbers and other identification recognizable by the user and by enterprise resource management systems also constitute communication means.

Alternate Embodiment 2

A second alternate embodiment of the present invention includes actuation means (200), spreader means (700), retaining means, keying means, feedback means, gripping means, illumination means and communication means.

Specifically, the second alternate embodiment of the present invention, illustrated in at least FIGS. 19A, 19B, AE2_1 through AE2_9; is a dilator device (100) consisting at least of an outer slider tube (500) having a slider ring (600), an inner slider rod (300) concentrically disposed within the outer slider tube (500), the inner slider rod (300) including a keying element (380) preventing the inner slider rod (300) from rotating within the outer slider tube (500); the outer slider tube (500) including a keying element (550) preventing the inner slider rod (300) from rotating within it.

A first link inner slider rod handle (340) is pivotally connected to an extension (582) of the outer slider tube (500) via an outer slider tube pivot point (585) and a handle pivot pin (345,60). The extension (582) of the outer slider tube is connected to an outer slider tube end cap (580) which is positioned at a second end (570) of the outer slider tube (500). The outer slider tube end cap (580) may be threaded onto the second end (570) of the outer slider tube (500) or secured in other known fashions, such as via insertion into the second end (570) of the outer slider tube (500) or via bonding to the second end (570) of the outer slider tube (500). The first link (340) operates as an inner slider rod handle and is connected between the inner slider rod (300) and the outer slider tube (500) by a second link (350). An inner slider rod end face (370) is disposed at a second end (360) of the inner slider rod (300) opposite the first end (310) of the inner slider rod (300). The inner slider rod (300) includes at least one keying feature (380) which aligns it to a mating keying feature (550) in the outer slider tube (500). The inner slider rod second end (360) includes keying features (384) which align spreader means (700). An inner slider rod passage way (376) is provided within the inner slider rod (300). The inner slider rod passage way (376) extends from the inner slider rod end face (370) towards the inner slider rod first end (310), wherein the inner slider rod passage way (376) exits the inner slider rod (300) at a location (378) off-set from a center (376). The inner slider rod end face (370) further includes tapered surfaces (374) extending into the inner slider rod passage way (376), wherein an intermediate sleeve (400), is threadable from the inner slider rod end face (370) through the inner slider rod passage way (376) and out the inner slider rod passage way exit (378). Spreader means (700) are keyed (606) with, and removably attached to (514) at the outer slider tube first end (510).

In this alternate embodiment of the present invention, illustrated in FIGS. 19A, 19B, AE2_1 through AE2_9, the actuation means (200) are provided by an actuator mechanism which is comprised of a first link lever handle (340) that pivots near the dilator's end, driving a second intermediate link (350) that is attached from the handle first link to the inner slider rod (300), where the handle is attached to and pivots from near the second end of the outer slider tube (571). This handle arrangement with a linkage provides a mechanical advantage to the operator. The surfaces of the handle (322) and a handle element (532) on the outer slider tube (500), which contact the operator's hand, are heavily textured, providing gripping means. The location of the handle element pair affords substantial ergonomic advantages to the operator in terms of gripping, guiding and manipulating the device with a single hand.

In this alternate embodiment of the present invention spreader means (700) can be comprised of slider arms (800) which are pivotally attached (820) to slider ring pins (610) mounted in a slider ring (600), which is attached to the first end (510) of the outer slider tube (500). These slider arms (800) are driven outward by the translation of the inner slider rod (300) through the outer slider tube (500) against their inner surfaces (842,844). The slider arms (800) are retained against the inner slider rod (300) by a retaining ring (1201). Alternate spreader means (700) which can be utilized in this second alternate embodiment of the present invention include a plurality of spreader arm limbs (1830) which are pivotally attached (1820) to slider ring pins (610) mounted in a slider ring (600), constituting a spreader arm assembly. This spreader arm assembly is attached to the first end (510) of the outer slider tube (500). As is shown in FIGS. AE2_9A, AE2_9B and AE2_9C need to annotate these spreader arm limbs (1830) are driven outward by the translation of the inner slider rod (300) through the outer slider tube (500) against their inner surfaces (1842, 1844). The spreader arm limbs (1830) are retained against the inner slider rod (300) by a retaining ring (1201).

The retaining means of this alternate embodiment of the present invention, shown in FIGS. AE2_1, AE2_2, AE2_5, AE2_9A and AE2_9C need to annotate, are deployed in the respective spreading means (700). These spreading means may also hold and incorporate a keyed, curved tipped (430), intermediate sleeve (400) which can further enhance the retention of the dilator during use.

In this alternate embodiment of the present invention keying means, shown in FIGS. AE2_3, AE2_5, AE2_6, AE2_8A and AE2_8B need to annotate, are comprised of a keyway (550) inside the outer slider tube (500) which relates to a key (380) on the outer surface of the inner slider rod (300). The outer slider tube (500) is keyed (514) at its first end (510) shown in FIG. AE2_5 need to annotate, to the spreading means (700).

In this alternate embodiment of the present invention feedback means are tactile feedback created within the actuator means (see FIGS. AE2_8, AE2_9, FM2A, FM2B need to annotate), by a surface on a spring element (520) in the outer slider tube (500) which engages a mating feature (382) on the surface of the inner slider rod (300). Translation of the inner slider rod with respect to the outer slider tube creates tactile feedback to the operator as the feature (382) on the inner slider rod (300) passes the mating surface element (520) of the outer slider tube (500).

In this alternate embodiment of the present invention additional feedback means are comprised of the tactile interaction (see FIG. AE2_1 need to annotate), of the second end of the inner slider rod (315) where it engages mating features on the spreader means (700). These features operate similarly to those discussed in the preferred and first alternate embodiments, depending on the spreader means employed.

Further additional feedback means of this alternate embodiment of the present invention, are for the inner slider rod (300) to display markings (383) that inform the user through their relative position (see FIG. FM2), to a feature or edge near an end of the outer slider tube (500), or near a feature or edge of the slider ring (600) mounted to the outer slider tube (500).

Still further additional feedback means of this alternate embodiment of the present invention, are provided by colored tips on the spreader means (700) which are visible from inside the trachea when illuminated with a broncheoscope.

In this alternate embodiment of the present invention gripping means are provided (see FIG. AE2_1 need to annotate), by heavily textured surfaces (342, 560) of the first link handle (340) and outer slider tube (500) respectively, which contact the operator's hand. The location of the handle near the end of the dilator affords substantial ergonomic advantages to the operator in terms of gripping, guiding and manipulating the device with a single hand.

The illumination means of this alternate embodiment of the present invention (see FIGS. AE2_1 and AE2_3 need to annotate), is generally comprised of a point source of light (390) contained in the inner slider rod (300), which projects onto the spreader means (700) and stoma in the trachea. An extension of illumination means for this second alternate embodiment of the present invention would include the use spreader means (700) in conjunction with an intermediate sleeve (400) made from a material which enables it to function as a light pipe.

The communication means of this alternate embodiment of the present invention (see FIGS. AE2_2 and CM03 need to annotate), are comprised of RFID chips in an actuator element (782) as well as in (781,4781) the spreader means (700). Degradable material such as PVA or PLA polymer which deteriorates after exposure to various cleaning regimens, used for the actuator means (200), spreader arm assembly (1800), or intermediate sleeve (400) also constitute communication means. Markings (783), including barcodes, glyphs, serial numbers and other identification recognizable by the user and by enterprise resource management systems also constitute communication means.

Alternate Embodiment 3

A third alternate embodiment of the present invention includes actuation means (200), spreader means (700), retaining means, keying means, feedback means, gripping means, illumination means and communication means.

Specifically the third alternate embodiment of the present invention, as shown in at least FIG. 34, and FIGS. 35A, 35B and 35C, AE3_1, AE3_2A-AE3_2E, AE3_3, AE3_4, AE3_5, AE3_6 and AE3_7 uses a single molded polymer housing is to construct the dilator device (100) consisting at least of an outer slider tube segment (4500), an inner slider rod segment (4300) which when folded and inserted is concentrically disposed within the outer slider tube segment (4500), the inner slider rod segment (4300) including a keying element (4380) preventing the inner slider rod segment (4300) from rotating within the outer slider tube segment (4500); the outer slider tube segment (4500) including a keying element (4550) preventing the inner slider rod segment (4300) from rotating within it. A first link, inner slider rod handle segment (4340) is disposed at a second end (4570) of the outer slider tube segment (4500). The first link inner slider rod handle segment (4340) operates as an inner slider rod handle and is connected between the inner slider rod segment (4300) and the outer slider tube segment (4500) by a second link segment (4350). An inner slider rod end face (4370) is disposed at a second end (4360) of the inner slider rod segment (4300) opposite the first end (4310) of the inner slider rod segment (4300). The inner slider rod segment (4300) includes at least one keying feature (4380) which aligns it to a mating keying feature (4550) in the outer slider tube segment (4500). The inner slider rod segment second end (4360) includes keying features (4384) which align spreader arm limbs (4830). An inner slider rod passage way (4376) is provided within the inner slider rod segment (4300). The inner slider rod passage way (4376) extends from the inner slider rod segment end face (4370) towards the inner slider rod segment first end (4310), wherein the inner slider rod segment passage way (4376) exits the inner slider rod segment (4300) at a location (4378) off-set from a center (4376). The inner slider rod segment end face (4370) further includes tapered surfaces (4374) extending into the inner slider rod segment passage way (4376), wherein an intermediate sleeve (400), is threadable from the inner slider rod segment end face (4370) through the inner slider rod segment passage way (4376) and out the inner slider rod segment passage way exit (4378). A plurality of spreader arm limbs (4824) are pivotally (flexibly) attached to the outer slider tube segment first end (4510). A retaining ring (1201) can be positioned to constrain the plurality of spreader arm limbs (4824) against the inner slider rod segment second end (4360). The plurality of spreader arm limbs (4824) also holds the intermediate sleeve (400), through which a metal guide (50) can be threaded.

In this alternate embodiment of the present invention the actuation means (200) (shown in FIGS. 34, AE3_1, AE3_2 and AE3_3) are provided by an actuator mechanism which is comprised of a first link lever handle segment (4340) that pivots (flexes) near the dilator's end, driving a second intermediate link segment (4350) that is attached from the handle first link segment to the inner slider rod segment (4300), where the handle is attached to and pivots from the middle of the outer slider tube segment (4500). This handle arrangement with a linkage provides a mechanical advantage to the operator. The surfaces of the first link handle segment (4342) and outer slider tube segment (4500) which contact the operator's hand, are heavily textured, providing gripping means. The location of the handle near the end of the dilator affords substantial ergonomic advantages to the operator in terms of gripping, guiding and manipulating the device with a single hand.

The spreader means (700) in this alternate embodiment of the present invention (shown in FIGS. 34, AE3_1, AE3_2, AE3_3, AE3_4, AE3_5, AE3_6, and AE3_7) are generally comprised of spreader arm limbs (4830) which are commonly extending and pivotally (flexibly) attached (4826) to the first end (4510) of the outer slider tube segment (4500). These spreader arm limbs (4830) are driven outward by the translation of the inner slider rod segment (4300) through the outer slider tube segment (4500) against their inner surfaces (4842, 4844). The spreader arm limbs (4830) can be retained against the inner slider rod segment (4300) by a retaining ring (1201).

The retaining means in this alternate embodiment of the present invention are (shown in FIGS. 34, 35, AE3_1, AE3_2, AE3_3, AE3_5, AE3_6, and AE3_7) generally comprised of the circumferential tactile detent depression features (4870) which continue from surface to surface of adjacent spreader arm limbs (4830).

The keying means in this alternate embodiment of the present invention (shown in FIGS. AE3_4, AE3_5, KM4, and KM5), are generally comprised of a keyway (4550) inside the outer slider tube segment (4500) which relates to a key (4380) on the outer surface of the inner slider rod segment (4300). The outer slider tube segment (4500) is keyed to the pivoting ends (4826) of the spreader arm limbs (4824) by means of the dilator's unitary construction. The inner slider rod segment (4300) has peripheral keyways (4384) to engage the surfaces of the spreader arm limbs (4831). An extension of spreader means for this third alternate embodiment of the present invention, would include the spreader arm limb tips (4890) having keying features/bridging tabs (4894) at their second end (4811) which engage with keying features/bridging tabs (418) of an intermediate sleeve (400), when the dilator is used with an intermediate sleeve to carry the metal guide wire.

The feedback means in this alternate embodiment of the present invention (shown in FIGS. AE3_6, AE3_7 and FM_4), are generally comprised of the tactile interaction of the second end of the inner slider rod segment (4360) where it engages notches on the inside surface (4831) of at least one spreader arm limb (4830); as well as visual feedback provided by the spreading of spreader arm limbs (4824).

Additional feedback means in this alternate embodiment of the present invention are provided by colored tips on the spreader arm limbs, which are visible from inside the trachea when illuminated with a broncheoscope.

The gripping means in this alternate embodiment of the present invention (shown in FIGS. AE3_1 and AE_3) generally comprise heavily textured surfaces on the outer surface (4342) of the first link handle segment (4340), and at least the opposing surface (4533) of the outer slider tube segment (4500).

The illumination means in this alternate embodiment of the present invention (shown in FIGS. 34, AE3_3 and IM_4), are generally comprised of a point source of light (4390) contained in the inner slider rod segment (4300), which projects onto the spreader arm limb tips and stoma in the trachea. An extension of illumination means for this third alternate embodiment of the present invention would include the use of spreader means (700) in conjunction with an intermediate sleeve (400) made from a material which enables it to function as a light pipe.

The communication means of this alternate embodiment of the present invention are generally comprised of an RFID chip (4281) in an actuator element (shown in FIGS. 34, AE3_3, and CM_4), and degradable material and marking (4282) used for the unitary assembly (100) which deteriorates after exposure to various cleaning regimens.

Alternate Embodiment 4

Mid Handle not Adjustable

The fourth alternate embodiment of the present invention, as shown in at least FIG. 38, and FIGS. 39A, 39B, 39C, AE4_1, AE4_2, AE4_3, AE4_4, AE4_5, AE4_6 and AE4_7, uses a single molded polymer housing is to construct the dilator device (100) consisting at least of an outer slider tube segment (4500), an inner slider rod segment (4300) which when folded and inserted is concentrically disposed within the outer slider tube segment (4500), the inner slider rod segment (4300) including a keying element (4380) preventing the inner slider rod segment (4300) from rotating within the outer slider tube segment (4500); the outer slider tube segment (4500) including a keying element (4550) preventing the inner slider rod segment (4300) from rotating within it. A first link, inner slider rod handle segment (4340) is disposed near a first end (4510) of the outer slider tube segment (4500). The first link inner slider rod handle segment (4340) operates as an inner slider rod handle and is connected between the inner slider rod segment (4300) and the outer slider tube segment (4500) by a second link segment (4350). An inner slider rod end face (4370) is disposed at a second end (4360) of the inner slider rod segment (4300) opposite the first end (4310) of the inner slider rod segment (4300). The inner slider rod segment (4300) includes at least one keying feature (4380) which aligns it to a mating keying feature (4550) in the outer slider tube segment (4500). The inner slider rod segment second end (4360) includes keying features (4831) which align spreader arm limbs (4830). An inner slider rod passage way (4376) is provided within the inner slider rod segment (4300). The inner slider rod passage way (4376) extends from the inner slider rod segment end face (4370) towards the inner slider rod segment first end (4310), wherein the inner slider rod segment passage way (4376) exits the inner slider rod segment (4300) at a location (4378) off-set from a center (4376). The inner slider rod segment end face (4370) further includes tapered surfaces (4374) extending into the inner slider rod segment passage way (4376), wherein an intermediate sleeve (400), is threadable from the inner slider rod segment end face (4370) through the inner slider rod segment passage way (4376) and out the inner slider rod segment passage way exit (4378). A plurality of spreader arm limbs (4824) are pivotally (flexibly) attached to the outer slider tube segment first end (4510). A retaining ring (1201) can be positioned to constrain the plurality of spreader arm limbs (4824) against the inner slider rod segment second end (4360). The plurality of spreader arm limbs (4824) also holds the intermediate sleeve (400), through which a metal guide (50) can be threaded.

In this alternate embodiment of the present invention the actuation means (200) (Shown in at least FIG. 38, and FIGS. 39A, 39B, 39C, AE4_1, AE4_2, AE4_3) are provided by an actuator mechanism which is comprised of a first link lever handle segment (4340) that pivots (flexes) near the dilator's middle, driving a second intermediate link segment (4550) that is attached from the handle first link segment to the inner slider rod segment (4300), where the handle is attached to and pivots from the middle of the outer slider tube segment (4500). This handle arrangement with a linkage provides a mechanical advantage to the operator. The surfaces of the first link handle segment (4342) and outer slider tube segment (4500) which contact the operator's hand, are heavily textured, providing gripping means. The location of the handle near the middle of the dilator affords substantial ergonomic advantages to the operator in terms of gripping, guiding and manipulating the device with a single hand.

The spreader means (700) of this alternate embodiment of the present invention (Shown in at least FIG. 38, and FIGS. 39A, 39B, 39C, AE4_1, AE4_2, AE4_3, AE4_4, AE4_5, AE4_6 and AE4_7) are generally comprised of spreader arm limbs (4830) which are commonly extending and pivotally (flexibly) attached (4826) to the first end (4510) of the outer slider tube segment (4500). These spreader arm limbs (4830) are driven outward by the translation of the inner slider rod segment (4300) through the outer slider tube segment (4500) against their inner surfaces (4842,4844). The spreader arm limbs (4830) can be retained against the inner slider rod segment (4300) by a retaining ring (1201).

The retaining means in this alternate embodiment of the present invention are generally comprised of the circumferential tactile detent depression features (4870) which continue from surface to surface of adjacent (un-)actuated spreader arm limbs (4830).

The keying means of this alternate embodiment (shown in FIGS. AE4_4, AE4_5, KM4, and KM5) are generally comprised of a keyway (4550) inside the outer slider tube segment (4500) which relates to a key (4380) on the outer surface of the inner slider rod segment (4300). The outer slider tube segment (4500) is keyed to the pivoting ends (4826) of the spreader arm limbs (4824) by means of the dilator's unitary construction. The inner slider rod segment (4300) has peripheral keyways (4384) to engage the surfaces of the spreader arm limbs (4831). The spreader arm limb tips (4890) have keying features/bridging tabs (4894) at their second end (4811) which engage with keying features/bridging tabs (418) of the intermediate sleeve (400).

The feedback means in this alternate embodiment of the present invention (shown in FIGS. AE4_6, AE4_7 and FM_4), are generally comprised of the tactile interaction of the second end of the inner slider rod segment (4360) where it engages notches on the inside surface (4831) of at least one spreader arm limb (4830); as well as visual feedback provided by the spreading of spreader arm limbs (4824).

Additional feedback means are provided by colored tips on the spreader arm limbs, which are visible from inside the trachea when illuminated with a broncheoscope.

The gripping means in this alternate embodiment of the present invention generally comprise heavily textured surfaces on the outer surface (4342) of the first link handle segment (4340), and at least the opposing surface (4533) of the outer slider tube segment (4500).

The illumination means in this alternate embodiment of the present invention (shown in FIGS. 34, AE4_3 and IM_4), is generally comprised of a point source of light contained in the inner slider rod segment (4300), which projects onto the spreader arm limb tips and stoma in the trachea. An extension of illumination means for this fifth alternate embodiment of the present invention would include the use spreader means (700) in conjunction with an intermediate sleeve (400) made from a material which enables it to function as a light pipe.

The communication means of this alternate embodiment of the present invention are generally comprised of an RFID chip (4281) in an actuator element, and degradable material and marking (4282) used for the unitary assembly (100) which deteriorates after exposure to various cleaning regimens.

Alternate Embodiment 5

Mid Handle Adjustable

A fifth alternate embodiment of the present invention, as shown in at least FIG. 38, and FIGS. 39A, 39B and 39C, includes actuation means (200), spreader means (700), retaining means, keying means, feedback means, gripping means, illumination means and communication means.

In this alternate embodiment of the present invention the feedback means, illumination means, and communication means are substantially the same as in the preferred embodiment.

This fifth alternate embodiment of the dilator device (100) includes a single molded polymer housing as the outer slider tube segment (4500) and an inner slider rod segment (4300) which, when folded and inserted, is concentrically disposed within the outer slider tube segment (4500).

The inner slider rod segment (4300) including a keying element (4380) preventing the inner slider rod segment (4300) from rotating within the outer slider tube segment (4500).

The outer slider tube segment (4500) including a keying element (4550) preventing the inner slider rod segment (4300) from rotating within it.

A first link, inner slider rod handle segment (4340) is disposed at a first end (4510) of the outer slider tube segment (4500). A second link segment (4350) connects the first link inner slider rod handle segment (4340) to the inner slider rod segment (4300).

An inner slider rod end face (4370) is disposed at a second end (4360) of the inner slider rod segment (4300) opposite the first end (4310) of the inner slider rod segment (4300).

The inner slider rod segment at least one keying feature (4380) aligns and mates with the outer slider tube segment keying feature (4550).

A plurality of spreader arm limbs (4824) are pivotally (flexibly) attached to an outer slider tube segment first end (4510).

The inner slider rod segment second end (4360) includes keying features (4831) which align spreader arm limbs (4830).

An inner slider rod passage way (4376) is provided within the inner slider rod segment (4300). The inner slider rod passage way (4376) extends from the inner slider rod segment end face (4370) towards the inner slider rod segment first end (4310).

The inner slider rod segment passage way (4376) exits the inner slider rod segment (4300) at a location (4378) off-set from a center of the inner slider rod segment first end (4310).

The inner slider rod segment end face (4370) further includes tapered surfaces (4374) extending into the inner slider rod segment passage way (4376).

An intermediate sleeve (400), is threadable from the inner slider rod segment end face (4370) through the inner slider rod segment passage way (4376) and out the inner slider rod segment passage way exit (4378).

A retaining ring (1201) can be positioned to constrain the plurality of spreader arm limbs (4824) against the inner slider rod segment second end (4360). The plurality of spreader arm limbs (4824) also holds the intermediate sleeve (400), through which a metal guide (50) can be threaded.

In this alternate embodiment of the present invention the actuation means (200) are provided by an actuator mechanism which is comprised of a first link lever handle segment (4340) that pivots (flexes) near the dilator's proximal end. The first link lever handle segment (4340) is pivotally and contiguous connected to a second intermediate link segment (4350) which is pivotally attached to the inner slider rod segment (4300).

Movement of the first link lever handle segment (4340) drives the second intermediate link segment (4350) which in turn drives the inner slider rod segment (4300) in and out of the outer slider tube segment (4500).

This handle arrangement provides a force magnifying mechanical advantage to the operator (describe in more specific detail).

The surfaces of the first link handle segment (4342) and outer slider tube segment (4500) which contact the operator's hand, are heavily textured, providing gripping means. The location of the handle near the middle of the dilator affords substantial ergonomic advantages to the operator in terms of gripping, guiding and manipulating the device with a single hand. The gripping means further include at least the opposing surface (4533) of the outer slider tube segment (4500).

The spreader means (700) in this alternate embodiment of the present invention are generally comprised of spreader arm limbs (4830) which are commonly extending and pivotally (flexibly) attached (4826) to the first end (4510) of the outer slider tube segment (4500).

These spreader arm limbs (4830) are driven outward by the translation of the inner slider rod segment (4300) through the outer slider tube segment (4500) against their inner surfaces (4842,4844). The spreader arm limbs (4830) can be retained against the inner slider rod segment (4300) by a retaining ring (1201).

The retaining means in this alternate embodiment of the present invention are generally comprised of the circumferential tactile detent depression features (4870) which continue from surface to surface of adjacent spreader arm limbs (4830) (need to be sure this language is consistent with other embodiments).

The keying means in this alternate embodiment of the present invention are generally comprised of a keyway (4550) inside the outer slider tube segment (4500) which relates to a key (4380) on the outer surface of the inner slider rod segment (4300). The outer slider tube segment (4500) is keyed to the pivoting ends (4826) of the spreader arm limbs (4824) by means of the dilator's unitary construction. The inner slider rod segment (4300) has peripheral keyways (4384) to engage the surfaces of the spreader arm limbs (4831). The spreader arm limb tips (4890) have keying features/bridging tabs (4894) at their second end (4811) which engage with keying features/bridging tabs (418) of the intermediate sleeve (400).

The feedback means in this alternate embodiment of the present invention are generally comprised of the tactile interaction of the second end of the inner slider rod segment (4360) where it engages notches on the inside surface (4831) of at least one spreader arm limb (4830); as well as visual feedback provided by the spreading of spreader arm limbs (4824).

Additional feedback means in this alternate embodiment of the present invention are provided by colored tips on the spreader arm limbs, which are visible from inside the trachea when illuminated with a broncheoscope.

The illumination means in this alternate embodiment of the present invention are generally comprised of a point source of light (4390) contained in the inner slider rod segment (4300), which projects onto the spreader arm limb tips and stoma in the trachea. An extension of illumination means for this third alternate embodiment of the present invention, would include the use spreader means (700) in conjunction with an intermediate sleeve (400) made from a material which enables it to function as a light pipe.

The communication means of this alternate embodiment of the present invention are generally comprised of an RFID chip (4281) in an actuator element, and degradable material and marking (4282) used for the unitary assembly (100) which deteriorates after exposure to various cleaning regimens.

What is claimed is:

1. A dilating device, for performing a percutaneous tracheotomy using a threadable metal guide, the device dilating an orifice in the antero-tracheal wall, through which the device threads the metal guide, the dilating device comprising:
    an outer slider tube having a slider ring attached at its first end;
    an inner slider rod concentrically disposed within the outer slider tube, the inner slider rod including:
    a keying element preventing the inner slider rod from rotating within the outer slider tube,
    an inner slider rod handle disposed at a first end of the inner slider rod,
    a slider rod end face disposed at a second end of the inner slider rod opposite the first end of the inner slider rod,
    an inner slider rod passage way within the inner slider rod, the slider rod passage way extending from the slider rod end face towards the inner slider rod first end,
    wherein the slider rod passage way exits the inner slider rod at a location off-set from a center of the inner slider rod handle,
    the inner slider rod end face further including tapered surfaces extending into the slider rod passage way,
    wherein the metal guide is threadable from the inner slider rod end face through the slider rod passage way and out the inner slider rod passage way exit;
    a plurality of removable slider arms pivotally attached to the slider ring,
    a retaining ring positioned to constrain the plurality of slider arms against the inner slider rod.

2. The dilating device of claim 1 further including:
    wherein the plurality of slider arms are grouped into pairs, and
    further wherein each slider arm of at least one pair of slider arms terminates with curved tips opposite the slider arm first end.

3. The dilating device of claim 2 further including:
    wherein at least one of the plurality of slider arms further includes a dilation detent depression positioned away from the slider arm first end.

4. The dilating device of claim 1 further including:
    tactile detent means having a detent contact surface provided on the inner slider rod and a mating detent contact surface provided on either the outer slider tube or at least one slider arm.

5. The dilating device of claim 1 further including:
    wherein the travel of the slider arms is provided by the force of the interference between an outer contacting surface of the inner slider rod and a surface of each slider arm as the inner slider rod is driven against the slider arms by the pressing of the inner slider rod handle,
    wherein a diameter of the opening in anterotracheal wall formed during dilation is determined by the range of travel of the slider arms in conjunction with the outer contacting surface of the inner slider rod.

6. The dilating device of claim 5 further including:
    wherein the slider arms and the inner slider rod are selected to provide a maximum predetermined diameter of the opening in the anterotracheal wall, and
    tactile detent means having a detent contact surface provided on the inner slider rod and a mating detent contact surface provided on either the outer slider tube or at least one slider arm,
    wherein the diameter of the opening in the anterotracheal wall corresponds to feedback from the tactile detent means.

7. The dilating device of claim 5 further including:
    wherein the slider arms and the inner slider rod are selected to provide a maximum predetermined diameter of the opening in the anterotracheal wall, and
    visual markings on the outer slider tube of at least one slider arm indicative of the diameter of the opening in the anterotracheal wall formed by the travel of the slider arms in conjunction with the outer contacting surface of the inner slider rod during dilation.

8. The dilating device of claim 1 wherein the inner slider rod handle further includes mechanical linkage means connecting the inner slider rod to the outer slider tube to provide an amplification of force as the inner slider rod is driven against the slider arms by pressing on the mechanical linkage.

9. The dilating device of claim 8 wherein the mechanical linkage means includes a first link pivotally attached to the inner slider rod, a second link pivotally attached to the outer slider tube, and an adjustable pivot connecting the first link and second link.

10. A dilating device for percutaneous tracheotomy which dilates an orifice in the anterotracheal wall, through which device it is possible to thread a metal guide, the dilating device comprising:

an outer slider tube, an inner slider rod concentrically disposed within the outer slider tube, the inner slider rod includes:

a keying element preventing the inner slider rod from rotating within the outer slider tube, an inner slider rod handle disposed at a first end of the inner slider rod, a slider rod end face disposed at a second end of the inner slider rod opposite the first end of the inner slider rod, a inner slider rod passage way within the inner slider rod, the slider rod passage way extending from the slider rod end face towards the inner slider rod first end, wherein the slider rod passage way exits the inner slider rod at a location off-set from a center of the inner slider rod handle, the inner slider rod end face further including tapered surfaces extending into the slider rod passage way, wherein the metal guide is threadable from the inner slider rod end face through the slider rod passage way and out the inner slider rod passage way exit;

a spreader arm assembly including a slider ring removably attached to the outer slider tube at a spreader arm assembly first end, the spreader arm assembly further including a plurality of spreader arm limbs commonly extending from the spreader arm assembly first end, each spreader arm limb includes a tip positioned opposite the spreader arm assembly first end;

a retaining structure positioned to constrain the plurality of spreader arms limbs against the inner slider rod.

11. The dilating device of claim 10 further including:

an intermediate sleeve positioned between the spreader arm assembly and the inner slider rod.

12. The dilating device of claim 10 wherein the intermediate sleeve further includes a first end having tapered surfaces where a central passage way in the intermediate sleeve is axially aligned with the inner slider rod passage way, wherein the metal guide is successively threadable through the intermediate sleeve central passage way and the inner slider rod passage way, whereby the intermediate sleeve precedes the spreader arm assembly when inserted into the orifice as the dilator device is moved along the metal guide.

13. The dilating device of claim 10 wherein the inner slider rod handle further includes mechanical linkage means connecting the inner slider rod to the outer slider tube to provide an amplification of force as the inner slider rod is driven against the slider arms by pressing on the mechanical linkage.

14. The dilating device of claim 13 wherein the mechanical linkage means includes a first link pivotally attached to the inner slider rod, a second link pivotally attached to the outer slider tube, and an adjustable pivot connecting the first link and second link.

15. The dilating device of claim 10 further including:

tactile detent means having a detent contact surface provided on the inner slider rod and a mating detent contact surface provided on either the outer slider tube or at least one spreader arms limb.

16. A dilating device that dilates an orifice comprising:

an outer slider tube segment having a slider ring segment;

an inner slider rod segment concentrically disposed within the outer slider tube segment, the inner slider rod segment includes:

a keying element preventing the inner slider rod segment from rotating within the outer slider tube segment, an inner slider rod handle integrally disposed at a first end of the inner slider rod segment, a slider rod end face disposed at a second end of the inner slider rod segment opposite the first end of the inner slider rod segment, an inner slider rod passage way within the inner slider rod segment, the slider rod passage way extending from the slider rod end face towards the inner slider rod first end, wherein the slider rod passage way exits the inner slider rod segment at a location off-set from a center of the inner slider rod handle segment, the inner slider rod end face further including tapered surfaces extending into the slider rod passage way, wherein a guide is threadable from the inner slider rod segment end face through the slider rod passage way and out the inner slider rod segment passage way exit;

a spreader arm assembly segment integrally attached to the slider ring segment at a spreader arm assembly segment first end, the spreader arm assembly segment including a plurality of spreader arm limbs commonly extending from the spreader arm assembly segment first end, each spreader arm limb includes a tip positioned opposite the spreader arm assembly segment first end;

a retaining structure positioned to constrain the plurality of spreader arms limbs against the inner slider rod segment.

17. The dilating device of claim 16 further including:

an intermediate sleeve with a centrally positioned passage way;

the intermediate sleeve positioned within the spreader arm assembly segment;

wherein the intermediate sleeve can be threaded with the threadable guide.

18. The device of claim 16 wherein the inner slider rod segment further includes mechanical linkage means connecting the inner slider rod segment to the outer slider tube segment to provide an amplification of force as the inner slider rod segment is driven against the spreader arm limbs by pressing on the mechanical linkage.

19. The dilating device of claim 18 wherein the mechanical linkage means includes a first link segment pivotally attached to the inner slider rod segment, a second link segment pivotally attached to the outer slider tube segment.

20. The dilating device of claim 16 further including:

tactile detent means having a detent contact surface provided on the inner slider rod segment and a mating detent contact surface provided on either the outer slider tube segment or at least one spreader arm limb.

* * * * *